US012232751B2

(12) United States Patent
Thio et al.

(10) Patent No.: US 12,232,751 B2
(45) Date of Patent: *Feb. 25, 2025

(54) ASPIRATION THROMBECTOMY SYSTEM AND METHODS FOR DYNAMIC SYSTEM STATE DETECTION

(71) Applicant: Penumbra, Inc., Alameda, CA (US)

(72) Inventors: Cheng Yong Timothy Thio, Davis, CA (US); Lincoln Herbert Davidson, Fargo, ND (US); Scott Teigen, West Fargo, ND (US); Corey Teigen, Rosholt, SD (US)

(73) Assignee: Penumbra, Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/365,127

(22) Filed: Aug. 3, 2023

(65) Prior Publication Data
US 2024/0164800 A1    May 23, 2024

Related U.S. Application Data

(63) Continuation of application No. 17/991,536, filed on Nov. 21, 2022, now Pat. No. 11,730,499.
(Continued)

(51) Int. Cl.
*A61B 17/22* (2006.01)
*A61B 17/00* (2006.01)
*A61M 1/00* (2006.01)

(52) U.S. Cl.
CPC .............. *A61B 17/22* (2013.01); *A61M 1/77* (2021.05); *A61B 2017/00292* (2013.01); *A61B 2017/22079* (2013.01); *A61M 2205/3331* (2013.01)

(58) Field of Classification Search
CPC ......... A61B 17/22; A61B 2017/22079; A61M 1/77; A61M 2205/3331
See application file for complete search history.

(56) References Cited

U.S. PATENT DOCUMENTS

| 10,485,952 B2 | 11/2019 | Garrison |
| 2009/0048607 A1 | 2/2009 | Rockley |

(Continued)

FOREIGN PATENT DOCUMENTS

| JP | 2021181858 A | 11/2021 |
| JP | 2021532850 A | 12/2021 |

(Continued)

*Primary Examiner* — Bradley J Osinski
(74) *Attorney, Agent, or Firm* — Baker Botts L.L.P.

(57) ABSTRACT

An aspiration thrombectomy system for use with a vacuum source and an aspiration catheter includes an aspiration catheter, connection tubing configured to act as a common conduit for fluid communication between the aspiration catheter and a vacuum source, controllable valves operable to selectively open and close to control fluid flow, pressure sensors associated with the aspiration catheter or the connection tubing, and an automatic controller configured to operate the valves in a first operational state to generate fluid pressure changes, detect pressure levels in the system, wherein changes in the detected pressure levels are correlated with the generated fluid pressure changes, determine system states based on system state scores determined based on the detected pressure levels, the system state scores indicating a measure of occlusion in the aspiration catheter or the connection tubing, and operate the valves in a second operational state based on the determined system states.

20 Claims, 69 Drawing Sheets

Related U.S. Application Data

(60) Provisional application No. 63/426,688, filed on Nov. 18, 2022.

(56) References Cited

U.S. PATENT DOCUMENTS

| | | |
|---|---|---|
| 2018/0207397 A1 | 7/2018 | Look |
| 2020/0367917 A1 | 11/2020 | Teigen |
| 2022/0160380 A1 | 5/2022 | Deville |
| 2022/0323096 A1 | 10/2022 | Naglreiter |

FOREIGN PATENT DOCUMENTS

| | | |
|---|---|---|
| JP | 2022018451 A | 1/2022 |
| WO | WO 2020023541 A1 | 1/2020 |

---

ASPIRATION THROMBECTOMY SYSTEM AND METHODS FOR DYNAMIC SYSTEM STATE DETECTION

PRIORITY

This application is a continuation under 35 U.S.C. § 120 of U.S. patent application Ser. No. 17/991,536, filed 21 Nov. 2022, which claims the benefit under 35 U.S.C. § 119(e) of U.S. Provisional Patent Application No. 63/426,688, filed 18 Nov. 2022, all of which are incorporated herein by reference.

TECHNICAL FIELD

The present disclosure relates generally to the field of medical devices and methods. More specifically, the particular embodiments described herein relate to devices and methods for controlling clot removal from a patient's vasculature by aspiration thrombectomy.

BACKGROUND

Stroke is a significant cause of disability and death, and a growing problem for global healthcare. More than 700,000 people in the United States alone suffer a stroke each year, and of these, more than 150,000 people die. Of those who survive a stroke, roughly 90% will suffer long term impairment of movement, sensation, memory, or reasoning, ranging from mild to severe. The total cost to the U.S. healthcare system is estimated to be over $50 billion per year.

Stroke may be caused by a blockage in a cerebral artery resulting from a thromboembolism (referred to as an "ischemic stroke"), or by a rupture of a cerebral artery (referred to as a "hemorrhagic stroke"). Hemorrhagic stroke results in bleeding within the skull, limiting blood supply to brain cells, and placing harmful pressure on delicate brain tissue. Blood loss, swelling, herniation of brain tissue, and pooling of blood that results in formation of clot mass inside the skull all rapidly destroy brain tissue. Hemorrhagic stroke is a life-threatening medical emergency with limited treatment options.

Aside from cerebral stroke, thromboembolism throughout the vasculature, in both arterial and venous circulation, is characteristic of numerous common, life-threatening conditions. Examples of potentially fatal diseases resulting from thrombotic occlusion include pulmonary embolism, deep vein thrombosis, and acute limb ischemia. Acute pulmonary embolism is a significant cause of death in the United States, with roughly 300,000 patients dying each year. Pulmonary embolism may be a complication from deep vein thrombosis, which has an annual incidence of 1% in patients 60 years and older. All of the aforementioned diseases are examples of conditions in which treatment may include aspiration or evacuation of clot and/or blood.

Of particular interest, the Penumbra System® mechanical thrombectomy system is a fully-integrated system designed specifically for mechanical thrombectomy by aspiration. It is intended for revascularization of patients with acute ischemic stroke secondary to intracranial large vessel occlusion. A comparable system designed for the peripheral and coronary vasculature, the Indigo® System is also a mechanical thrombectomy aspiration system, designed for revascularization of patients with thrombotic occlusion of the peripheral vasculature. Both the Penumbra System and the Indigo System are commercially available at the time of filing the present provisional patent application and include aspiration or reperfusion catheters, aspiration tubing, other accessories, and an aspiration pump (sold under the tradename: Pump MAX™ aspiration pump or Penumbra Engine™ aspiration pump) for connection to the aspiration tubing and aspiration catheters. As illustrated in FIG. 1, the Pump MAX™ aspiration pump 10 includes a base unit 12 which encloses a vacuum pump (not illustrated) which operates off line voltage. The base unit has an on-off switch 14 and a separate knob 16 for adjusting the level of vacuum provided by the pump. The vacuum level may be read on a pressure gauge 18. Blood and clot are drawn into a collection canister 20 from an aspiration tube 22 (illustrated in broken line) which is connected to a reperfusion catheter (not illustrated) which has been introduced to the vasculature of a patient to aspirate clot. The blood and clot are drawn into the collection canister by a partial vacuum which is provided by a vacuum connector 28 on the base unit 12 which is connected to the vacuum pump, not illustrated. The vacuum from vacuum connector 28 is applied to a vacuum port 24 on a removable lid 26. The vacuum connector 28 is connected to the vacuum port 24 by an external vacuum tube 30.

Although very effective, clot aspiration using the Indigo System mechanical thrombectomy apparatus or other similar vacuum-assisted thrombectomy systems must sometimes be terminated due to the risk of excessive blood loss by the patient, especially when using large aspiration catheters. During aspiration thrombectomy, when the catheter tip falls out of contact with the thrombus or other occlusive material, the tip is exposed to healthy blood and full flow ensues. Under such conditions, the blood loss rate is excessive, and in some cases, may result in premature termination of the procedure. In particular embodiments, during a procedure when the catheter enters healthy blood and full flow ensues, the blood loss rate is in the range of 20-25 cc per second with an 8 French size catheter. With a maximum tolerable blood loss of 300-1000 mL, the catheter may not run in unrestricted mode for more than approximately 20 to 50 seconds. When a physician operates the system manually, the aggregate blood loss may reach an unacceptable level before sufficient clot is removed. In addition, reliably identifying whether the tip of the catheter is in contact with clot or is undesirably aspirating healthy, clot-free blood is a significant problem, and such manual control is not optimum.

During other procedures using the Penumbra System, such as, for example, neurovascular procedures for treatment of ischemic stroke, excessive removal of blood may be less of a risk, and the primary focus of the procedure may be maximization of removal of occlusive material. Optimizing both technique and aspiration control are of upmost importance for successful removal of occlusive material.

Therefore, it would be desirable to provide improved methods and apparatus for controlling the aspiration of thrombus and clot using aspiration catheters in combination with pumping consoles. It would be particularly useful to provide systems and methods which limit blood loss during such aspiration procedures such as by automatically stopping aspiration while the aspiration catheter is not in contact with clot or thrombus. Additionally, it would be desirable to provide systems and methods which optimize system performance, and procedures for removal of occlusive material. At least some of these objectives will be met by the particular embodiments described herein below.

The Penumbra System® as it is commercially available at the time of filing this provisional patent application is described in a brochure entitled "Science of Aspiration: The Penumbra System® Approach." Relevant patents and patent publications include: U.S. Pat. Nos. 4,574,812; 5,624,394; 6,019,728; 6,283,719; 6,358,225; 6,599,277; 6,689,089;

6,719,717; 6,830,577; 8,246,580; 8,398,582; 8,465,467; 8,668,665; 9,248,221; US2003/0050619; US2010/094201; US2014/323906; US2014/276920; US2016/0220741; US2017/0238950; US2017/049470; WO2014/151209; and WO2010/045178.

SUMMARY OF PARTICULAR EMBODIMENTS

Particular embodiments described herein provide systems and methods that improve catheter aspiration by enabling a longer procedure, by enhancing the ingestion of occlusive material, or both. In particular embodiments, the amount of fluid flowing through an aspiration catheter under vacuum aspiration is monitored to determine whether the flow is unrestricted, restricted, or clogged. Depending on the determined flow state, particular embodiments may employ different techniques and methods to improve catheter aspiration. In particular embodiments, unrestricted flow is detected, and aspiration is automatically and temporarily restricted for blood saving purposes. This may beneficially prolong the time available to perform the procedure and thereby allow more complete removal of occlusive material. In another embodiment, restricted flow is detected, and full vacuum aspiration is automatically applied. In yet another particular embodiment, a clogged catheter is detected, and pulsed aspiration is automatically applied. This may beneficially enhance the ingestion of large, tough, or otherwise troublesome occlusions. Alternatively, pulsed aspiration, full aspiration, or restricted aspiration may be applied on demand by a user of particular embodiments.

In one particular embodiment, the systems and methods described address the problem of excessive blood loss through dynamic aspiration cycling. The nature and flowability of the material being withdrawn by the aspiration catheter is monitored so that the system may either allow continuous aspiration when in clot, or sampling of extraction rate to determine whether the tip of the catheter is in contact with clot, in order to reduce the risk of excess blood loss. While determining and monitoring of blood flow rate is disclosed in the exemplary embodiments below, other measurements of the flowability and/or structural composition of the aspiration effluent, such as monitoring the collection chamber's volume, monitoring the collection chamber's fill rate, visually monitoring the aspiration tubing (clot is darker than fresh blood), or placing a strain gauge on aspiration tubing, could also be used.

The systems and methods of particular embodiments may respond to variations in flow rate, pressure, differential pressure, or other indicators of the composition of the material inside or adjacent to an aspiration catheter in a sub-second time frame to limit the unnecessary aspiration of blood during a thrombectomy procedure. Particular embodiments may be useful with any thrombectomy, embolectomy, atherectomy, or other catheter or probe system where blood and clot are withdrawn wholly or partially by application of a vacuum to the proximal end of any reperfusion, aspiration catheter or probe for the purpose of clot extraction.

Particular embodiments provide a vacuum aspiration control system for use with a vacuum source and an aspiration catheter. The system comprises a flexible connection tubing, an on-off valve, a sensing unit, and a controller. The connection tubing is linear in an unconstrained configuration and is configured to connect the vacuum source to an aspiration lumen in the aspiration catheter. The on-off valve is configured to be operatively connected to the connection tubing, and the sensing unit is configured to determine flow rate within the connection tubing and to produce a signal representative of such flow, typically as either unrestricted flow, restricted flow, or clogged. The controller is connected to receive the signal representative of flow through the connection tubing and to open and close one or more on-off valve(s) in response to the signal. In one particular embodiment, the controller is configured to automatically close the on-off valve to stop flow through the connection tubing when the signal indicates unrestricted flow, e.g. that primarily healthy blood or blood free of vessel-obstructing clot is flowing through the connection tubing and/or that the catheter is substantially free from contact with clot or other occlusive material. In another particular embodiment, the controller is configured to initiate pulsed aspiration when the signal indicates a clog, which may be caused by some occlusive material in or adjacent to the catheter or connecting tubing.

The controller is typically further configured to automatically open the on-off valve at a predetermined interval to sample effluent material through the connection tubing and the valve will typically only remain open if the signal indicates a return to clot. The controller algorithm is capable of deciphering the difference between healthy blood and clot independent of aspiration source and the inner diameter of the attached catheter.

The sensing unit may comprise any one or more of a variety of sensors, including differential pressure sensors, acoustic (including ultrasonic) flow sensors, optical flow sensors, thermal flow sensors, magnetic flow sensors, sensors which detect circumferential expansion of the connection tubing, and the like. While differential pressures are described in more detail below, it will be appreciated that any sensing unit capable of detecting when flow or extraction rate through the connection tubing is excessive and/or clogged, would be suitable for use in particular embodiments.

In exemplary embodiments, the sensing unit comprises a pair of pressure sensors at spaced-apart locations along the connection tubing to measure differential pressure. The controller may calculate flow based on the differential pressure and, from this, determine whether the calculated flow rate indicates unrestricted flow, restricted flow, or a clog.

In another embodiment, the sensing unit uses optical sensors that measure transmission, absorption, or both of light to characterize the contents flowing through the connection tubing. In particular embodiments, visible light is used determine whether flow contains clot or is primarily clot-free. Typically, flow with clot is darker, which is detectable by optical sensors. Alternatively, the optical sensors may infrared, ultraviolet, visible light, or some such combination to analyze contents within the connecting tubing.

In other particular embodiments, the sensing unit uses circumferential expansion sensors to determine the contents flowing through the connection tubing. The internal pressure of the connecting tubing and the contents flowing through it effect the circumference of the connecting tubing. Under strong vacuum, such as during a clog, the tubing may maximally contract. During high flow of primarily clot-free blood, the tubing may contract only slightly. During restricted flow, the clots and blood may cause a relative expansion of the connecting tubing.

The on-off valve may also take a variety of specific forms. Typically, regardless of form, the on-off valve will comprise an actuator, such as a solenoid actuator, that is powered to open the valve. The valve itself may take a variety of forms, including a pinch valve, an angle valve, or any one of a variety of other valves that provide actuation. Alternatively, the manual on-off valve may be provided that allows a user to initiate and/or terminate functions and features of particular embodiments.

In further exemplary embodiments, the controller may be configured to open the valve and hold the valve open until a flow pattern which indicates unrestricted flow is detected whereupon the controller closes the valve. The controller may be further configured to automatically re-open the on-off valve. In particular embodiments, in what may be referred to as "sampling mode", the controller may be further configured to periodically sample, or test flow to re-characterize flow and determine if it is safe to recommence aspiration. For example, in particular embodiments, the controller may periodically test flow by opening the on-off valve for a fixed time interval, in one embodiment 150 milliseconds, to establish a "test" flow. The test flow is characterized and, if it so indicates, the on-off valve may be reopened into a "treatment" mode to allow continued aspiration treatment. If the system characterizes the flow as unrestricted, e.g. excessive, then the system will dwell in a closed configuration for a fixed time interval, in one embodiment between a quarter second and two seconds, before an additional pressure differential sample is taken.

In other embodiments, however, the controller may not be configured to automatically reestablish flow when safe conditions have been reached. For example, in particular embodiments, the controller may be configured to allow a user to reposition the aspiration catheter and, after repositioning, manually open the on-off valve (typically by actuating a switch which causes the controller to open the on-off valve) to resume aspiration treatment. In such instances, the controller may immediately return to the "sampling mode," however, and if the reestablished flow is characterized as unrestricted flow, the controller will again close the on-off valve, and the user may again reposition the aspiration catheter in order to engage clot and manually resume aspiration. Such systems will typically provide a manual switch which allows the user to manually open the on-off valve.

The controller may be configured to control two or more valves. In particular embodiments, the controller controls a first on-off valve between an aspiration catheter and a vacuum source and a second on-off valve between an aspiration catheter and a pressure source with a pressure at least above that of the vacuum source. The controller may alternate between opening the first on-off valve and the second on-off valve to generate pressure variations within an aspiration catheter or tubing adjacent to such a catheter. The controller may sample flow while the first on-off valve is opened to determine whether an attached catheter is still positioned in clot or otherwise occluded. The controller may hold the first on-off valve open and the second on-off valve closed if no occlusions or clogs are detected.

In specific embodiments, the vacuum aspiration systems comprise a base unit which incorporates at least one on-off valve and the controller. The base unit will typically be configured to be mounted directly on or near a vacuum pump or console and will usually include a connecting cable in order to receive power from the vacuum console or line and optionally exchange information with the controller and the vacuum console. The connection tubing typically has a proximal end configured to connect the vacuum source and distal end configured to connect to the aspiration catheter. In such instances, the vacuum aspiration system will typically further comprise an external unit configured to be secured to the connection tubing at a location between the distal end and the proximal end thereof. Exemplary external units comprise at least a portion of the sensing unit. For example, in particular embodiments, the sensing unit may comprise a first pressure sensor in the base unit and a second pressure sensor in the external unit. In those instances, the controller will typically be configured to determine if a differential pressure exists based on the signals from the first and the second pressure sensor.

In a second aspect, particular embodiments provide a vacuum aspiration method. The vacuum aspiration method comprises engaging a distal end of an aspiration catheter against an occlusion in the blood vessel. A vacuum is applied through an aspiration lumen of the aspiration catheter using a vacuum source coupled to a proximal end of the aspiration lumen by a connection tubing. In this way, portions of clot and other occlusive material may be drawn into the aspiration lumen, through the connection tubing, and into a collection receptacle by the vacuum source. Flow through the connection tubing is sensed, and a valve is automatically closed to stop flow through the connection tubing when the sensed flow exceeds a determined value while the vacuum source remains on. Flow through the connection tubing will be later reestablished by opening the valve, and the steps are repeated until a desired amount of clot has been aspirated.

In a third aspect, particular embodiments provide an assembly for generating pressure differentials that may result in pressure pulses to execute an extraction cycle. The assembly may include a fluid injection apparatus, a mechanical displacement apparatus, gravity induced pressure head, or a combination thereof. A fluid injection apparatus may provide a source of relative positive pressure for a catheter currently or previously under vacuum aspiration. For instance, the fluid may be at a pressure above that of the vacuum aspiration system, between full vacuum pressure and ambient pressure, at ambient pressure, between ambient pressure and systolic pressure, at systolic pressure, or above systolic pressure. The fluid injection apparatus may utilize an aperture, a valve, a pump, a pressure chamber, or some such combination. A mechanical displacement apparatus may physically displace the volume of a catheter system to provide relative increases and decreases of pressure depending on the direction of displacement. In particular embodiments, a mechanical displacement assembly assists vacuum recovery after a catheter has had its pressure increased above the pressure of the vacuum source.

In particular embodiments, the controller may include an algorithm that is used to interpret pressure sensor signals to determine whether the contents flowing through a catheter should be characterized as unrestricted, restricted, or clogged. Generally, unrestricted flow is a high flow that may be characterized as excessive and may be primarily or completely comprised of healthy blood, clot-free blood, or blood free of vessel-obstructing clot that is not helpful to aspirate, restricted flow may be comprised of a mix of healthy blood and clot or other occlusive material, and a clog may be caused by a clot or other occlusive material within an aspiration catheter, partially within an aspiration catheter, adjacent to an aspiration catheter, or in other connecting tubing attached to the aspiration catheter. In some examples, healthy blood may be blood with a low enough proportion of cross-linked fibrin such that it is not sufficiently integrated to cause ischemia or other similar vessel occlusions. When the algorithm detects unrestricted flow, it may cause the system to initiate a sampling mode. When the algorithm detects restricted flow, it may cause the system to enable full vacuum aspiration. When the algorithm detects a clog, it may cause the system to generate a variety of pressure pulses with an extraction cycle. The algorithm may be responsive and adaptable to changing circumstances, such as changing to a catheter of a different size mid-procedure. The algorithm may adjust sampling modes and pressure pulse magnitudes if the catheter state remains static, changes too quickly, changes to slowly, or improves as expected.

In specific aspects of the method, particular embodiments may remove clot and other occlusive material from a blood vessel that comprises a vein or an artery. Sensing of flow may comprise one or more of differential pressure measurement, acoustic flow measurement, optical flow measurement, thermal flow measurement, measurement of circumferential expansion of the connection tubing, and the like.

In preferred aspects of the method, sensing flow comprises measuring the differential pressure using a first sensor located proximate the vacuum source and a second sensor located on or adjacent the connection tubing between the vacuum source and the aspiration catheter.

In still further embodiments of the method, the resuming flow through the connection tubing comprises opening the valve for a sub-second interval, detecting when the sensed flow is characterized as acceptable, and automatically resuming flow. Automatically resuming flow typically comprises automatically detecting when the sensed flow may be characterized as acceptable and the valve remains open as long as the flow is so characterized. Alternatively, resuming flow may comprise manually opening the on-off valve.

In further embodiments of the method, pressure differentials are generated by closing a valve to a vacuum pump, opening a valve to a source of pressure, wherein the pressure is at least above that of the vacuum, and then re-opening the valve to the vacuum pump. Alternatively, or in combination, pressure differentials are generated by mechanical displacement, wherein a volume of a chamber is reduced to increase pressure within a catheter and a volume of the chamber is increased to decreases pressure within a catheter, whereby the actuation of the mechanical displacement chamber results in pressure differentials. The pressure differentials may be tailored to have a specific or dynamic amplitude and frequency that facilitates the removal of clot or other occlusive materials.

In particular embodiments, with respect to dynamic system state detection, the controller may generate pressure level changes in the connection tubing by operating the vacuum valve, such as by selectively opening and closing the vacuum valve. In a second step, the controller may detect pressure levels using the distal pressure sensor, where changes in the detected pressure levels are correlated with the generated pressure level changes. In a third step, the controller may determine one or more system states in the aspiration catheter or the connection tubing based on the detected pressure level changes. In a fourth step, the controller may operate the vacuum valve to take action based on the one or more determined system states.

In particular embodiments, system states may comprise flow states within the aspiration catheter and/or connection tubing. In particular embodiments, flow states may comprise an open flow state, an occluded flow state, and/or a partially occluded flow state. In specific aspects, system states may comprise the presence of specific fluids in the aspiration catheter and/or connection tubing.

In particular embodiments, the controller may be configured to detect the presence of saline liquid in the system based on dynamic system state detection, such as for priming, flushing, or repriming the system, or to detect loss of saline during pulsing. In particular embodiments, the controller may be configured to detect the presence of gas in the system, such as air bubbles, based on dynamic system state detection. In particular embodiments, the controller may be configured to detect the absence of a catheter attached to the system based on dynamic system state detection. In particular embodiments, the controller may be configured to detect clot engagement with the tip of the catheter based on dynamic system state detection.

In particular embodiments, dynamic system state detection may separately or additionally use pressure sources and/or valves other than vacuum valves. In particular embodiments, systems may use a vacuum valve, a pressure valve such as a saline vent valve, and/or multiple other pressure valves.

Particular embodiments of this dynamic system state detection methodology may separately or additionally use sensors other than the distal pressure sensor. In particular embodiments, systems may use one or more pressure sensors associated with the connection tubing and/or aspiration catheter, and other pressure sensors, such as a vacuum pressure sensor, and a saline pressure sensor. Sensors used in particular embodiments may not be limited to pressure sensors. In some embodiments, a variety of sensors may be used, for instance, sensors for detecting pressures, sonic energy, ultrasonic energy, and/or flow rates.

In particular embodiments, one or more system scores may be determined for determining system states, wherein each system score, independently or in combination with other system scores, may indicate a likelihood of specific system states in the aspiration catheter or the connection tubing. In this respect, system scores may function as metrics for quantifying the corresponding likelihood of specific system states.

In particular embodiments, system scores may be directly or indirectly derived from sensor data, such as pressure profiles. In particular embodiments, system score determination may be based on automatically identifying specific features from the detected pressure profiles, extracting pressure parameters based on values and trends derived from those specific features, and calculating one or more system scores based on the pressure parameters of those features. In particular embodiments, determining system scores based on pressure parameters may further comprise appropriate weighting of the parameters, and/or use of correction factors. In particular embodiments, the pressure parameters may comprise one or more of a starting pressure level, a differential in starting pressure levels, an ending pressure level, a differential in ending pressure levels, a peak pressure level, and a variance in pressure levels.

In particular embodiments, system scores may be determined based on machine learning. In particular embodiments, training data sets may be assembled from detected pressure profile data taken over a broad range of scenarios, incorporating statistical variations, and corresponding to system states of interest. Trained machine learning models may be then used to make predictions of system state for novel situations. In particular embodiments, machine learning algorithms may employ semi-supervised and unsupervised learning. The algorithms may employ clustering, dimensionality reduction, and reinforcement learning to further improve prediction accuracy. In particular embodiments, an algorithm that uses a combination of the above algorithmic flow analysis techniques may be employed.

In particular embodiments, one or more of the system state scores may be based on one or more geometric characteristics of the aspiration catheter, and wherein the one or more geometric characteristics of the aspiration catheter may be determined based on the one or more detected pressure levels. In particular embodiments, one or more of the system state scores may be based on one or more ambient environmental parameters of the aspiration thrombectomy system. In particular embodiments, one or more of the system state scores may be based on one or more material parameters associated with the aspiration thrombectomy system, and wherein the one or more material parameters may be determined based on the one or more detected pressure levels. In particular embodiments, one or more of the system state scores may be based on one or more thrombi parameters associated with one or more thrombi in the aspiration catheter or the connection tubing, wherein the one or more thrombi parameters may be determined based on the one or more detected pressure levels. In particular embodiments, one or more of the system state scores may be based on one or more fluid parameters associated with one or more fluids in the aspiration catheter or the connection tubing, wherein the one or more fluid parameters may be determined based on the one or more detected pressure levels.

In particular embodiments, an escalation feature may be used wherein an Escalate Count of consecutive determinations of identical system state is maintained by the controller, and specific action may be taken if the count exceeds a threshold. In particular embodiments, the count may be reset in the iteration following the threshold crossing iteration. In specific aspects, the action taken if the count exceeds a threshold may be generating a notification, such as a user notification. In particular embodiments, the action taken if the count exceeds a threshold may involve the operation of one or more valves by the controller.

The embodiments disclosed herein are only examples, and the scope of this disclosure is not limited to them. Particular embodiments may include all, some, or none of the components, elements, features, functions, operations, or steps of the embodiments disclosed herein. Embodiments according to the invention are in particular disclosed in the attached claims directed to a method and a system, wherein any feature mentioned in one claim category, e.g. method, can be claimed in another claim category, e.g. system, as well. The dependencies or references back in the attached claims are chosen for formal reasons only. However any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

DESCRIPTION OF EXAMPLE EMBODIMENTS

Aspiration Thrombectomy Systems

Particular embodiments are described below. For clarity, not all features of each actual implementation are described in this specification. In the development of an actual device, some modifications may be made that result in an embodiment that still falls within the scope of this disclosure.

Figure 1:
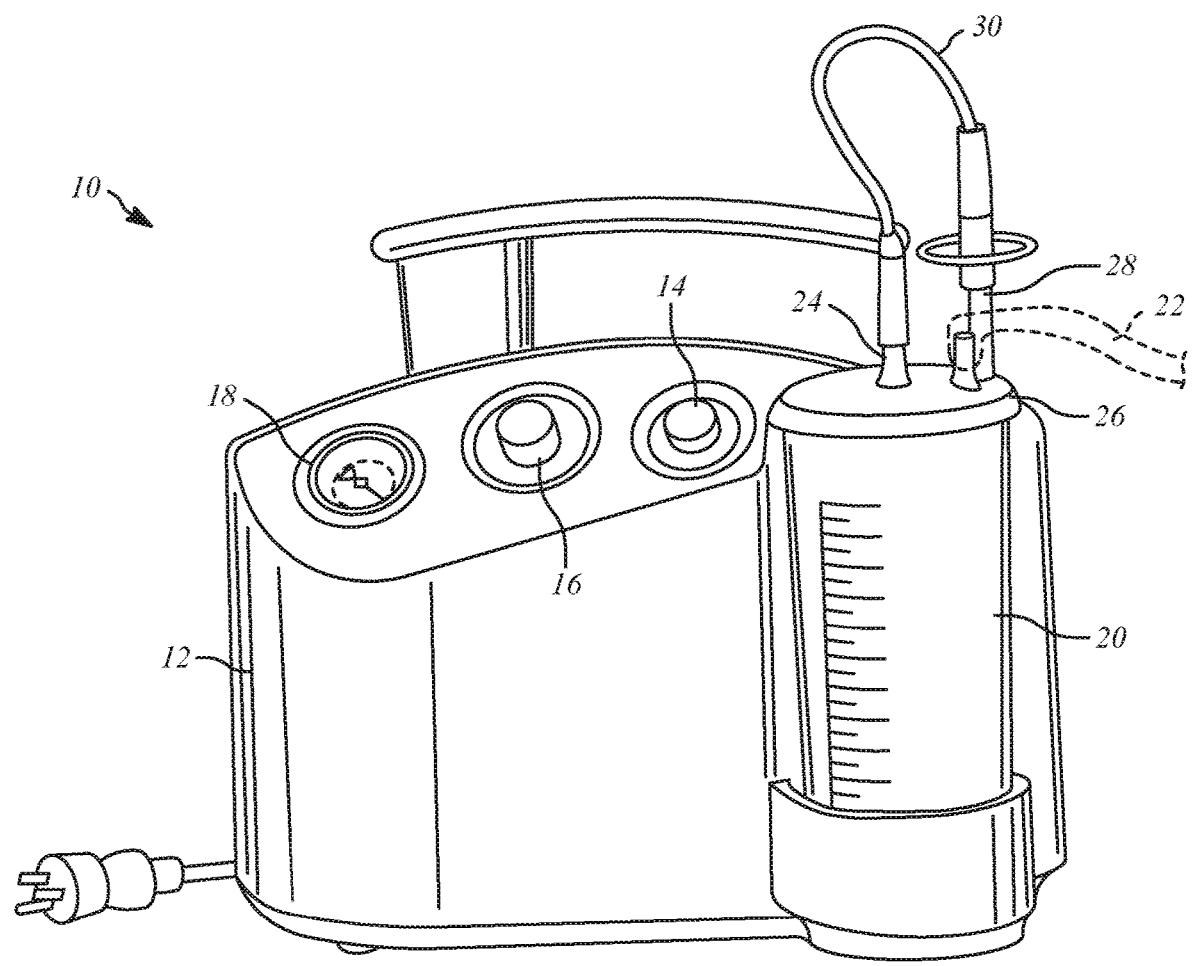
FIG. 1 illustrates the vacuum console and collection canister of the Penumbra System® mechanical thrombectomy system as described in detail in the Background.

FIG. 1 illustrates the vacuum console and collection canister of the Penumbra System® mechanical thrombectomy system as described in detail in the Background.

Figure 2:
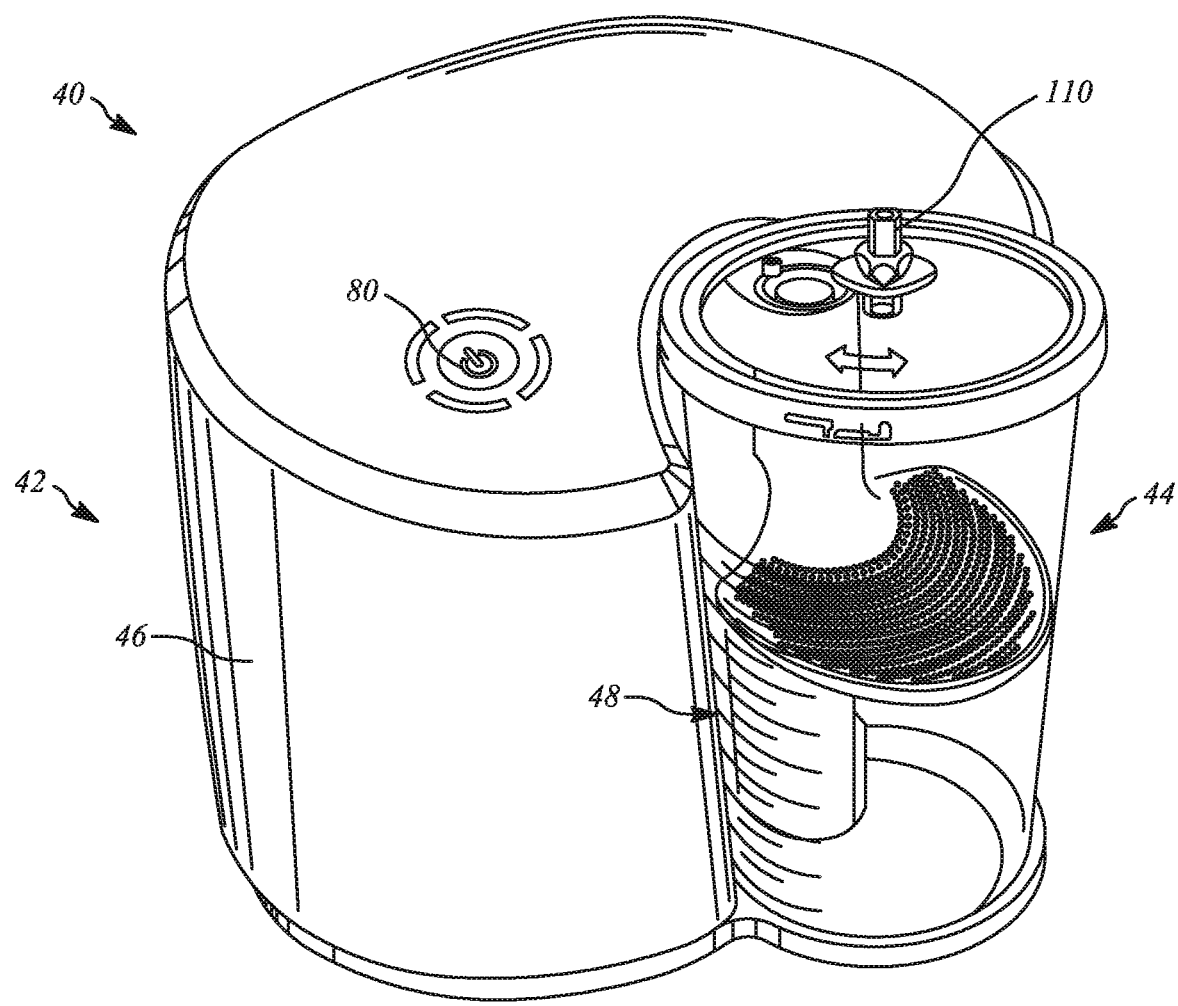
FIG. 2 is a perspective view of a vacuum console and a blood and clot collection canister with the collection canister received in a mounting region of the vacuum console.

Referring to FIGS. 2-6, particular embodiments of a vacuum system 40 of the type useful with the apparatus and methods for controlled clot aspiration will be described. FIG. 2 is a perspective view of a vacuum console and a blood and clot collection canister with the collection canister received in a mounting region of the vacuum console. The vacuum system 40 includes a vacuum console 42 and a blood/clot collection canister 44. The vacuum console 42 comprises an enclosure having a recess 48 which is shaped to removably receive the collection canister 44 as will be described in more detail below.

Figure 3A:
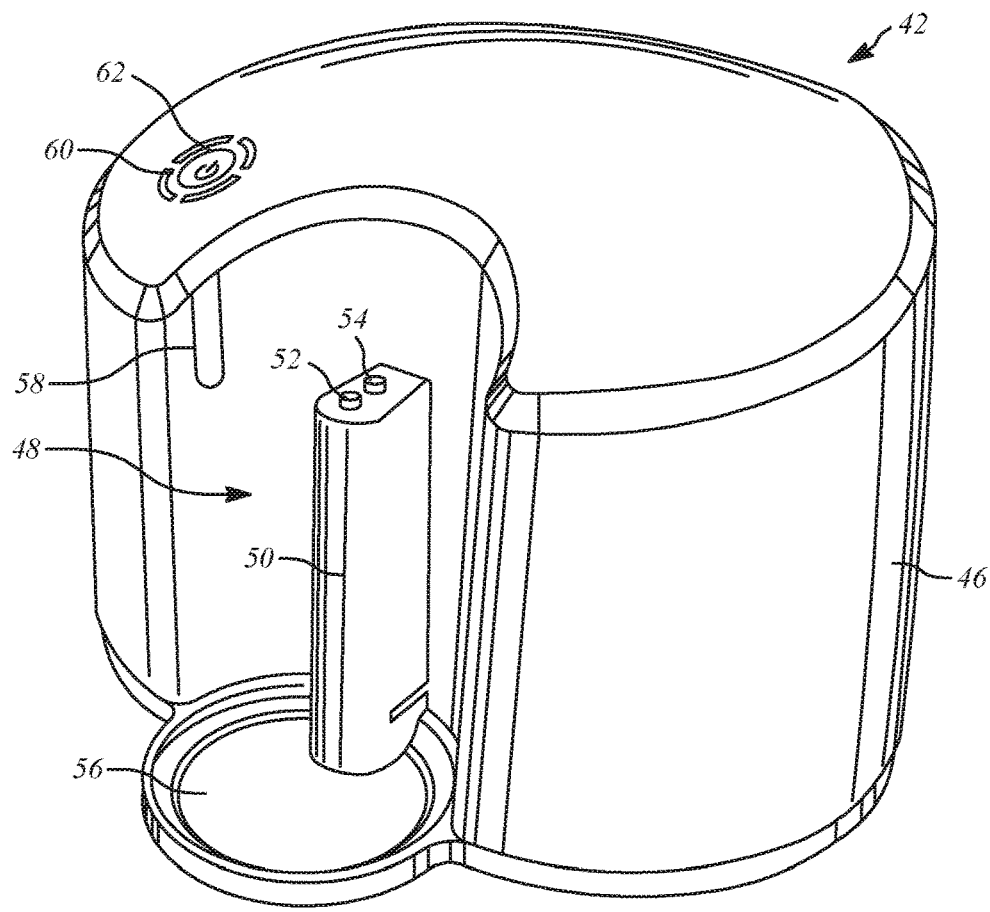
FIG. 3A is a view of the vacuum console of illustrated with the collection canister removed.
Figure 3B:
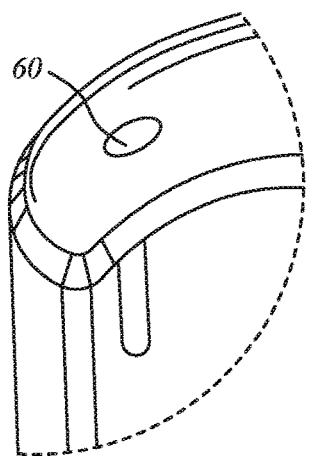
FIG. 3B is a detailed view of the on-off switch and a vacuum display region on a top surface of the vacuum console of FIG. 3, illustrated with the power off.
Figure 3C:
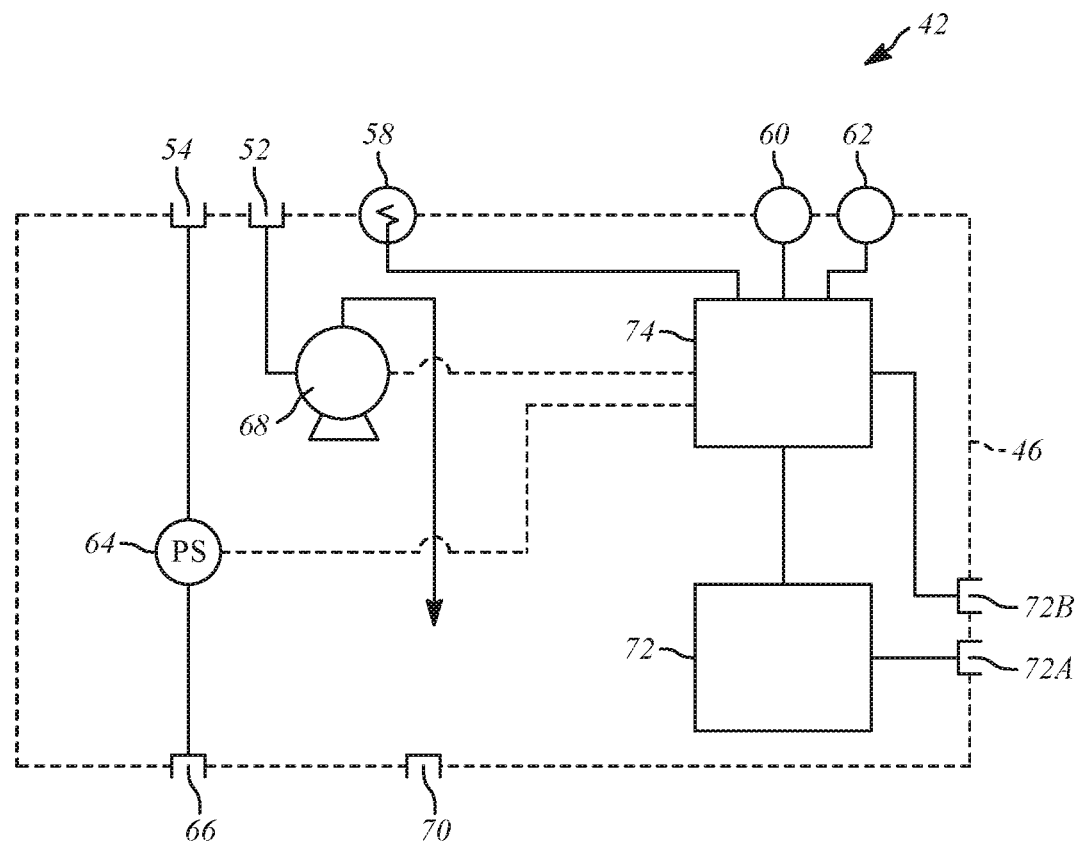
FIG. 3C is a schematic representation of the internal components of the vacuum console of FIGS. 1 to 3A.

Referring to FIGS. 3A-3C, particular embodiments of the vacuum console 42 are illustrated with the vacuum canister 44 removed. FIG. 3B is a detailed view of the on-off switch and a vacuum display region on a top surface of the vacuum console of FIG. 3, illustrated with the power off. FIG. 3C is a schematic representation of the internal components of the vacuum console of FIGS. 1 to 3A. A post 50 which forms a contiguous portion of the outer surface or wall of the enclosure 46 is formed within the recess 48 and extends upwardly from a bottom plate 56 which acts as a support for the collection canister 44 when it is received within the recess. A vacuum connector 52 and a pressure sensing connector 54 are formed in or on an upper surface of the post 50 and are located so that they will align with a pressure sensing port 104 and a vacuum port 102 (FIG. 5) on the vacuum canister 44 when it is received within the recess 48. One light 58 is located on a wall surface of the enclosure 44 within the recess 48 and is located so that it will illuminate the contents of the collection canister 44 when the system is in use. A second light (not visible in in FIG. 3A) is present on the opposite wall of the recess 48. The vacuum console 42 also has an on-off switch 60 on its upper surface. The on-off switch 60 illuminates when it is on (as illustrated in FIGS. 2 and 3A) and is not illuminated when the system is off (FIG. 3B). Additionally, a pressure display 62 is provided on the upper surface of the enclosure 46. As illustrated in FIGS. 2 and 3A, the display may be a circular light, e.g. having four segments which are sequentially illuminated as the vacuum level within the canister increases. Each quadrant represents the measured vacuum as a percentage of ambient pressure.

The internal components of the vacuum console 42 are schematically illustrated in FIG. 3C. The primary internal components of the vacuum console include a pressure sensor 64, a pump 68, a power supply 72, and a microprocessor controller 74. The pump 68 has an inlet connected to the vacuum connector 52 on the post 50 of the enclosure 46. Similarly, the pressure sensor 64 is connected to the pressure sensing connector 54 on the post 50. The pump can be turned on by the switch 60 and will draw vacuum through the connector 52 and release removed gas into an interior of the console. The console in turn is vented by a vent 70 on a bottom surface of the enclosure 46.

In particular embodiments, the functions of the pump will be controlled by the microprocessor controller 74, and the pressure output from sensor 64 will also go through the microprocessor controller 74. Each of the light 58, switch 60, and display 62 will be connected to the microprocessor controller 74 which is powered by the power supply 72. The power supply 72 is powered through line current connector 72A. The USB connector 72B is powered by microprocessor controller 74. The pump is plugged into an outlet via a power cord that is supplied with the pump. The power supply converts the AC current from the wall outlet to DC current which is what the microprocessor controller uses to power the pump, switch, lights, USB connector, etc.

In particular embodiments, pressure sensor 64 is connected to the microprocessor controller 74 and measures vacuum pressure in the canister through the pressure sensing connector 54. A second pressure sensor (not illustrated) is also connected to the microprocessor controller 74 and measures ambient pressure outside of the pump enclosure through an internal tube that is routed to a vent in the base of the pump. The microprocessor controller takes the vacuum pressure reading from the pressure sensor 64 and divides it by the ambient pressure reading from the second pressure sensor to calculate the vacuum pressure in the canister as a percent of ambient pressure.

Figure 4:
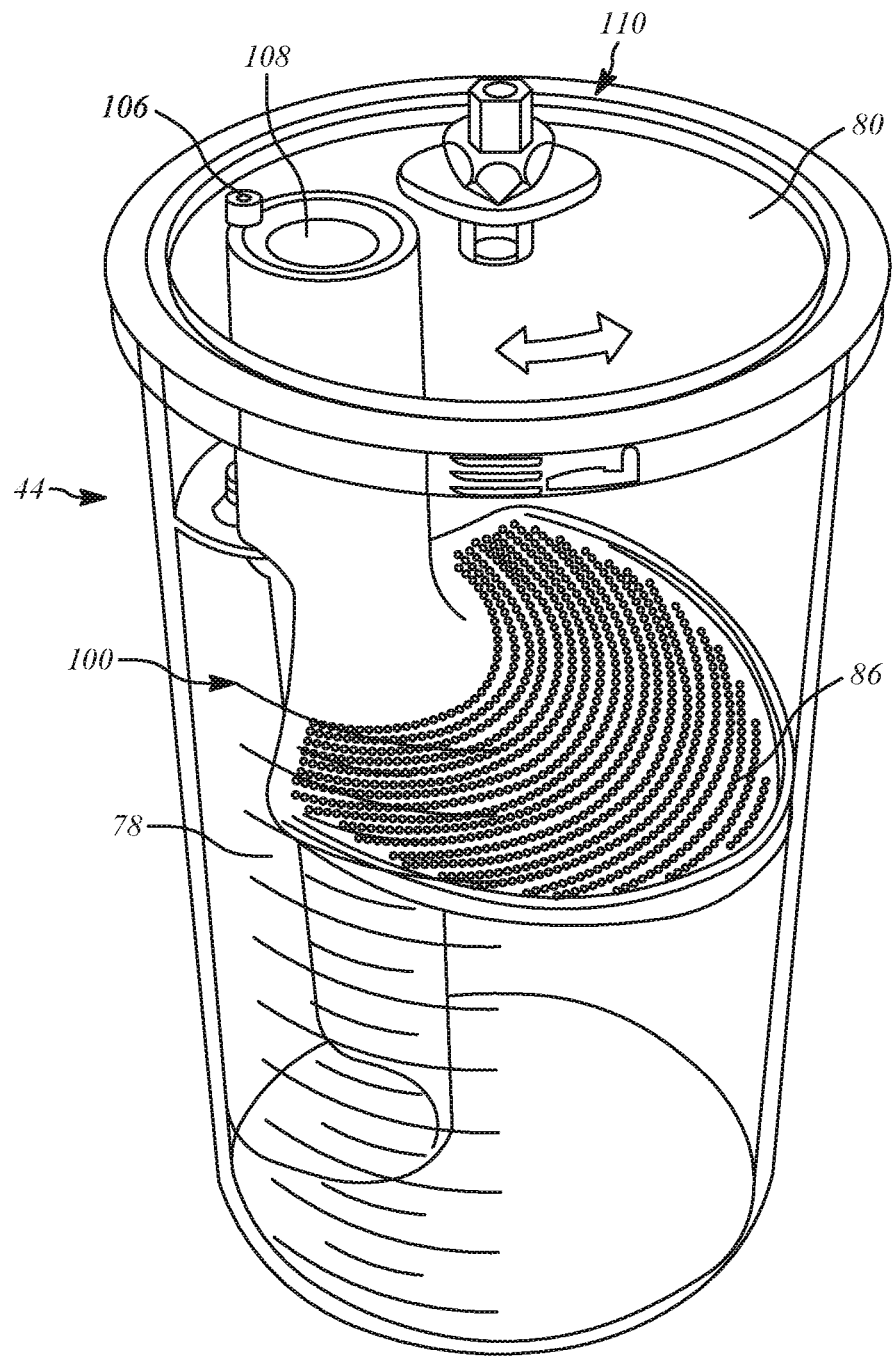
FIG. 4 illustrates a collection canister.
Figure 5:
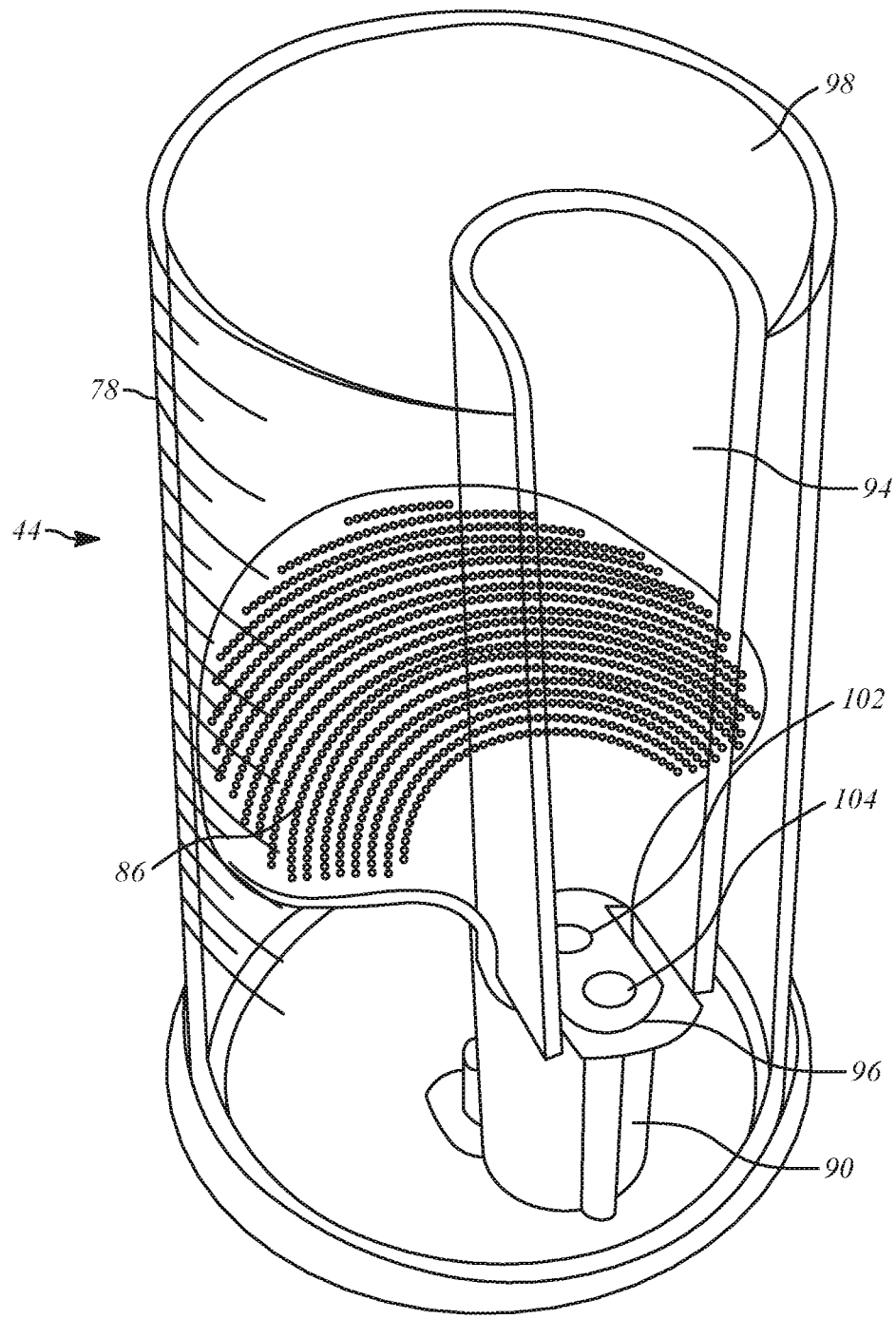
FIG. 5 illustrates an embodiment of the collection canister of FIG. 4, depicted in an inverted or "upside down" view.
Figure 6:
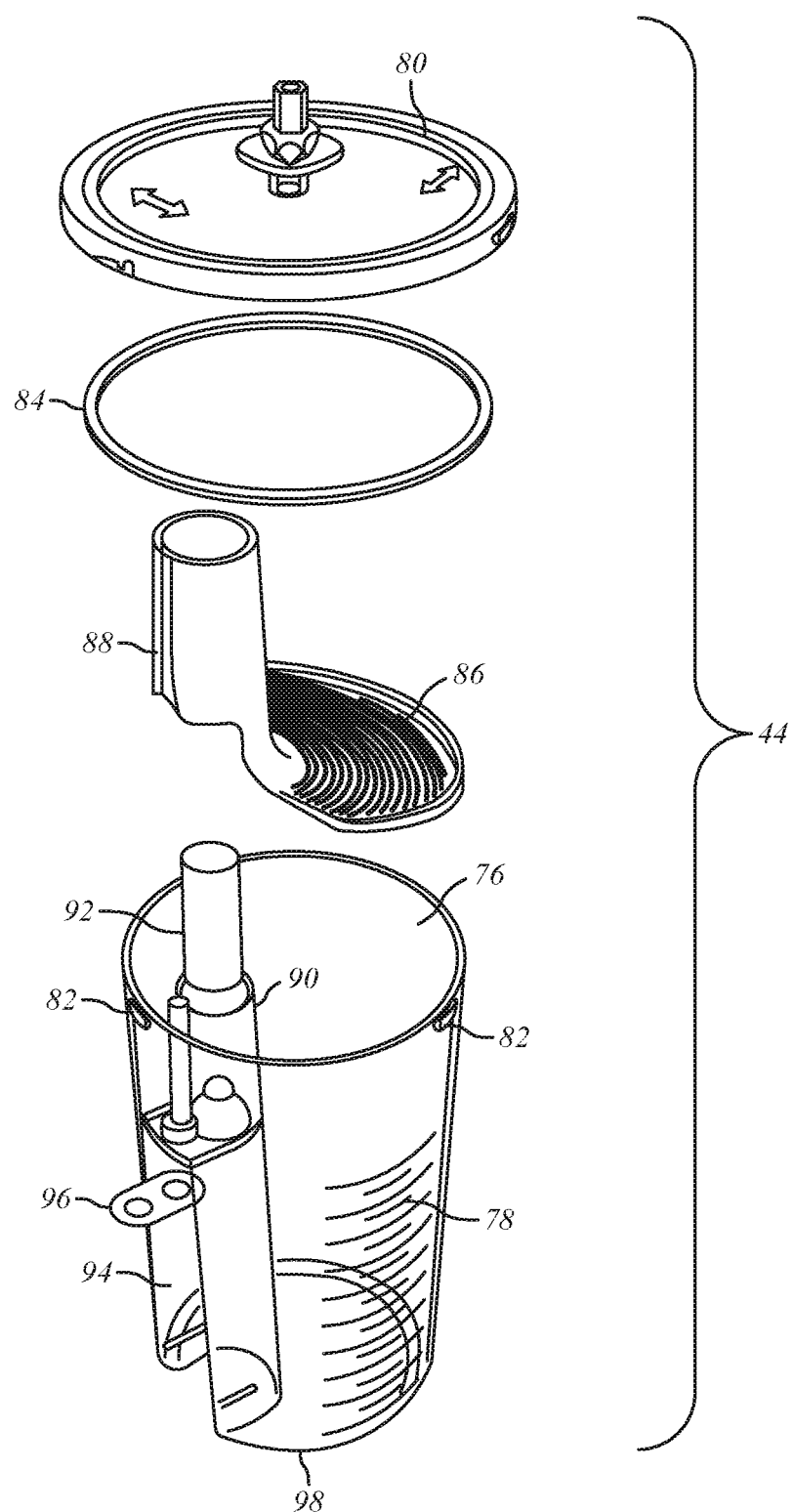
FIG. 6 is an exploded view of the vacuum canister of FIGS. 4 and 5.

Referring now to FIGS. 4-6, particular embodiments of the collection canister 44 has a main body 78 which is typically formed from a polished, clear plastic material which is molded into the illustrated shape. FIG. 4 illustrates a collection canister. FIG. 5 illustrates an embodiment of the collection canister of FIG. 4, depicted in an inverted or "upside down" view. FIG. 6 is an exploded view of the vacuum canister of FIGS. 4 and 5.

The main body 78 has an open upper end 76 which may be covered by a removable clear plastic lid 80. The clear plastic lid 80 is typically attached by a bayonet connector 82, and a form or other gasket 84 will seal the lid to the open end of the main body 78.

In particular embodiments, a groove 94 is formed in one side of the main body 78 and is shaped so that it may be placed over the post 50 in the recess 48 of the enclosure 46 of the vacuum console 42. As illustrated in FIG. 5, the pressure sensing port 104 and the vacuum port 102 are located at the upper end of the groove 94 so that they align and connect with the vacuum connector 52 and pressure sensing connector 54 on the post 50 when the canister 44 is in place in the recess 48.

In particular embodiments, the pressure sensing port 104 is connected to a tube or lumen which extends upwardly in the main body 48 of the canister 44 and terminates in an upper opening or aperture 106. Similarly, the vacuum port 102 extends upwardly through a much larger lumen or tube and terminates in an open aperture 108 at its upper end. The apertures 106 and 108 are located near the top of the interior of the main body 78 but will be below the bottom of the lid 80 when the lid is in place on the canister 44. Thus, both of the apertures 106 and 108 will be exposed to the interior of the canister 44 but will be maintained well above the mid-section and bottom where the clot and blood are collecting. In this way, the risk of contamination from blood and clot is minimized.

In particular embodiments, a filter plate 86, illustrated as a perforated screen but which could also be a woven screen or other separating member, is held in the mid-section of the interior of the main body 78 of the canister 44. The clot is drawn into the interior of the canister through a connector 110 which is attached to a proximal end of the catheter or other tubing. The clot and blood are drawn into the interior of the main body 78 by the vacuum which is drawn through the vacuum port 102 by the vacuum console 42, as previously described. As the clot and blood fall downwardly from connector 110 into the canister 44, the clot collects on the upper surface of the filter plate 86 while the blood flows through the perforations in the plate and collects in the bottom of the canister. As the plate is inclined downwardly from a sleeve 88 which is mounted on a post 90 in the interior of the canister, excess blood may flow over an open bypass region 100 (FIG. 4) which is formed on a backside of the plate and allows the blood to flow directly down to the bottom of the canister. Filter body 92 occupies the interior of post 90 and aperture 108 and prevents extracted material from contaminating the interior of enclosure 42. Filter body 92 occupies the interior of post 90 and extends to aperture 108. The filter body may thus prevent extracted material from contaminating the interior of enclosure 42. A groove 94 is formed on a side of the main body 78 of the canister 44 and is received over the post 50 in the recess 48 of the enclosure 46 in order to align the vacuum and pressure sensing connectors and vacuum ports. A gasket 96 is further provided at the seal between the vacuum ports and the vacuum connectors.

While the exemplary apparatus and methods for controlled clot aspiration for particular embodiments illustrated in FIGS. 7-19 may be used with the vacuum system 40, as just described, it will be appreciated that the particular embodiments described and claimed herein are not limited to use with any particular vacuum console and instead are useful with any clot or other vascular thrombectomy or aspiration system including a thrombectomy or other vascular aspiration catheter in combination with a vacuum pump or other source where there is a risk of excess blood aspiration, clogging, or both.

Figure 7A:
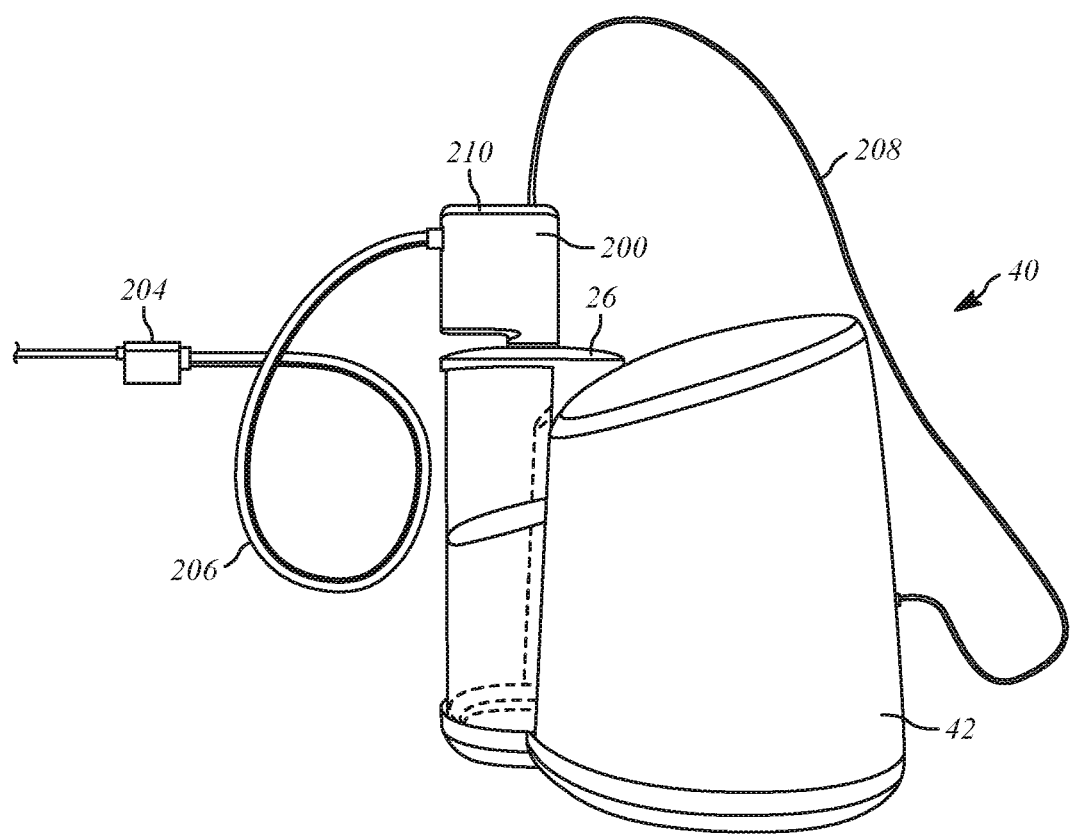
FIGS. 7A and 7B illustrate a vacuum console and collection canister, similar to those illustrated previously, having a vacuum aspiration control system attached thereto.
Figure 7B:
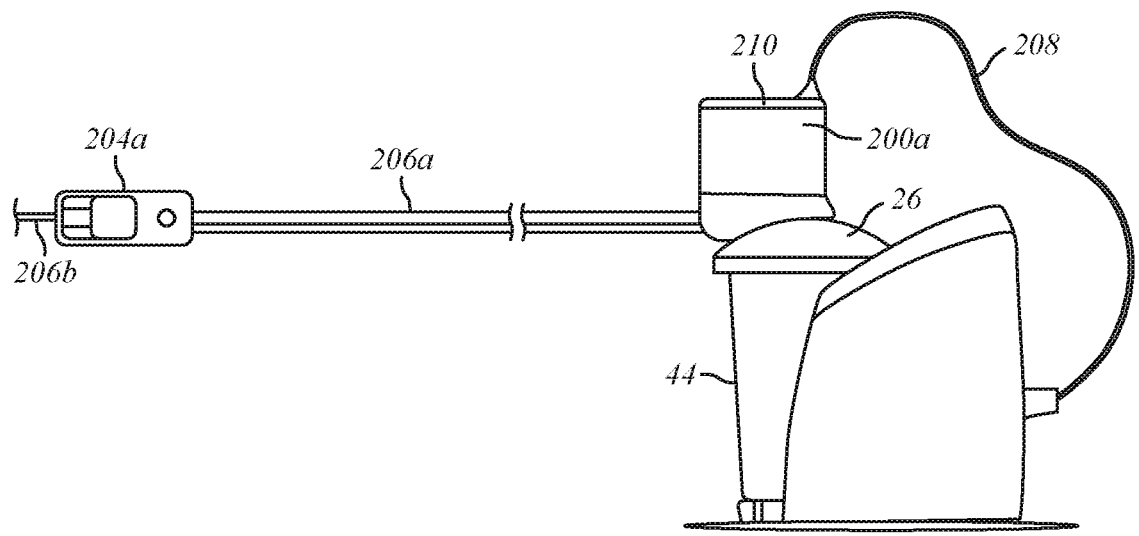

In particular embodiments, FIGS. 7A and 7B illustrate a vacuum console and collection canister, similar to those illustrated previously, having a vacuum aspiration control system attached thereto. They illustrate particular embodiments of an exemplary system 200 for performing controlled clot aspiration in accordance with the principles described, comprising a base unit 210 and an external unit 204. A proximal end of a connection tubing 206 is connected to the base unit 210, and the external unit is secured on or to the connection tubing at a location spaced apart from the proximal end, typically by some distance sufficient to make conclusions about flow. The external unit 204 may be configured to connect directly to a hub or other proximal end of an aspiration catheter or may be configured to be connected in the middle of the connection tubing. The connection tubing is linear in an unconstrained configuration and flexible along its length.

In particular embodiments, the base unit 210 may be configured to sit directly atop the lid 26 on the collection canister 44 of the previously described vacuum console 40. Typically, a communication cable extends from the base unit 210 through a portion of connecting tubing 206 to a connection receptacle on the vacuum console 40 so that the base unit may be powered by the vacuum console and optionally can communicate data with the controller within the vacuum console.

Figure 8A:
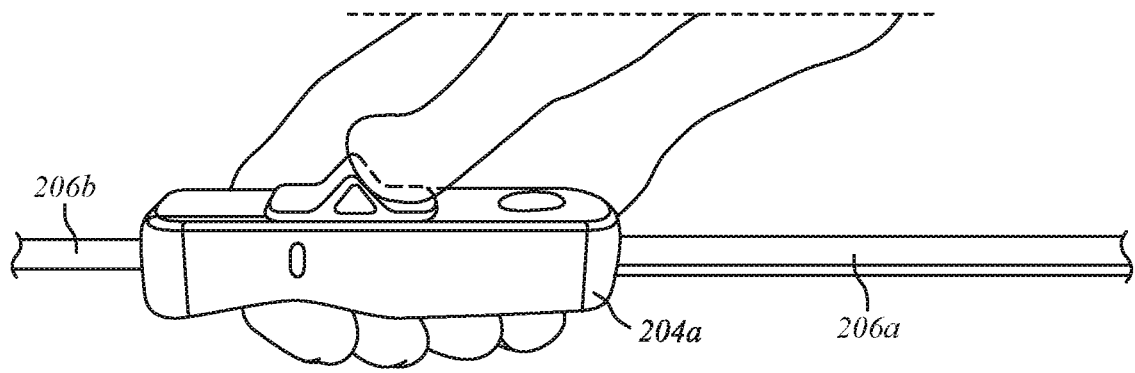
FIGS. 8A and 8B illustrate an external unit of the type suitable for use in particular embodiments.
Figure 8B:
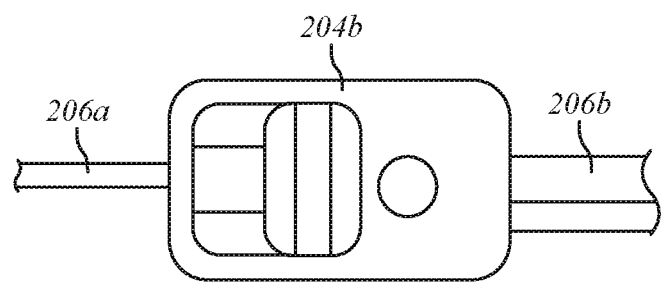

As illustrated in FIG. 7B, in particular embodiments, an external unit 204a may include a switch for initiating treatment using the vacuum console 40 and controlled clot aspiration system 200. The switch may also turn off the system, thereby providing a manual override of the algorithm that ensures the system is off with no flow. When the switch is on, the system may immediately enter an algorithm mode where it decides to remain open, enter a sampling mode, or initiate an extraction cycle in response to pressure sensor readings. Further details of the external unit 204a are illustrated in FIGS. 8A and 8B.

Figure 9:
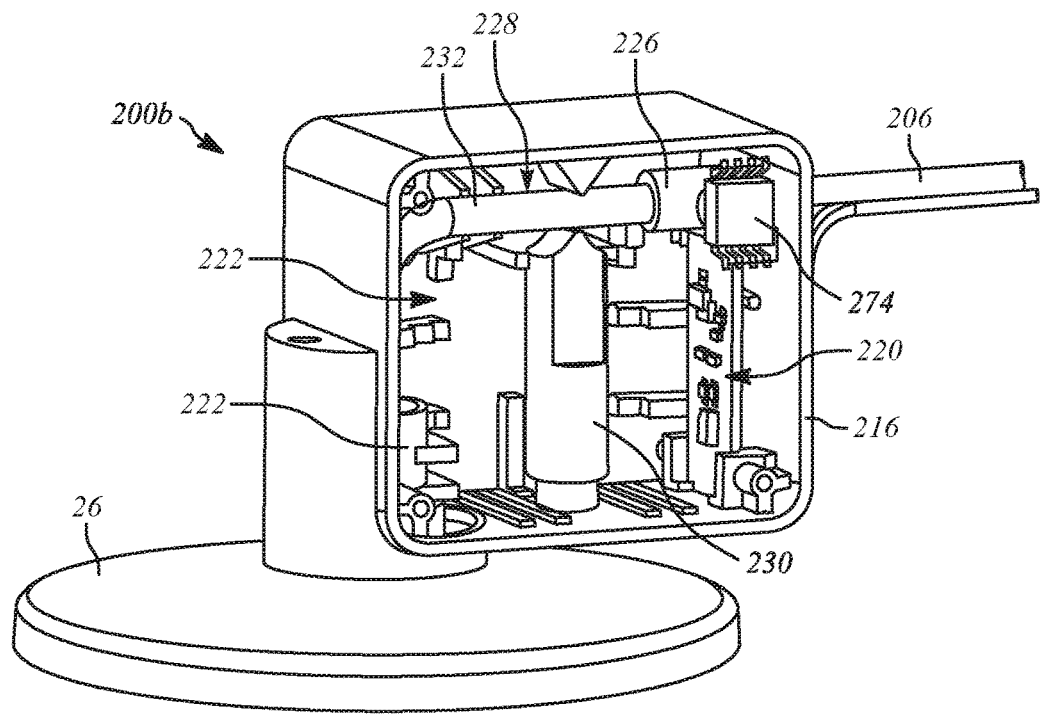
FIG. 9 illustrates an exemplary base unit enclosing an on-off valve and a controller of the type suitable for use in the vacuum aspiration control system, depicted in section.

FIG. 9 illustrates an exemplary base unit enclosing an on-off valve and a controller of the type suitable for use in the vacuum aspiration control system, depicted in section. In particular embodiments, an exemplary base unit 200b may comprise a base unit enclosure 216 having an open interior cavity 218 which receives a number of components. For example, a controller 220, typically including a microprocessor on a printed circuit board, may be mounted within the cavity 218 together with a pressure sensor 224 secured between a tube segment 228 and a proximal end on the connection tubing 206 by a pressure fitting 226. The tube segment 232 may be collapsible and positioned in a pinch valve 228 which is driven by a solenoid 230. Pinch valve 228 may be biased into a closed position by a compressive spring (not visible), unless it is opened by solenoid 230. The base unit 200b further includes a connecting fitting 222 which is configured to be removably secured to a vacuum fitting (not illustrated) on the lid 26 of the canister 44. The controller 220 is configured to open and close the pinch valve 228 to allow and prevent, respectively, the flow of clot and blood through the tubing segment 232 from the aspiration catheter into the collection canister. Optionally, base unit 200b may include a button (not pictured) in electronic communication with printed circuit board 220, for advanced user control of various parameters of the system. In particular embodiments, a base unit may house or be in communication with a pressure chamber, a fluid source, additional on-off valves, or some such combination.

In particular embodiments, an on-off valve and a controller of the type suitable for use in aspiration control systems may be used to apply mechanical forces on a clot, thrombus, or other occlusive material. During a maceration cycle, mechanical action by the on-off valve on the occlusive material may be used for cutting, shearing, chopping, dividing, softening, macerating, or otherwise modifying the form, consistency, and/or deformability of the occlusive material. Modifying the form or consistency of clots, thrombi, or other occlusive material by mechanical action may beneficially enable more effective aspiration of occlusive material through the aspiration catheter. For example, a large thrombus may be divided into smaller pieces for more effective aspiration. For example, a hard or dense thrombus may be mechanically softened or made more pliable by mechanical action to enable more effective aspiration. In particular embodiments, the pinch valve 228 may be used for applying mechanical forces and action on clots, thrombi, or other occlusive material. In particular embodiments, other types of valves, including but not limited to valves specifically designed for improved mechanical action on occlusive material, may be used. In particular embodiments, parameters for selective operation of the valve by the controller, including but not limited to timing, frequency, and/or duty cycle parameters, may be optimized to provide improved mechanical action by the valve on occlusive material.

Figure 10:
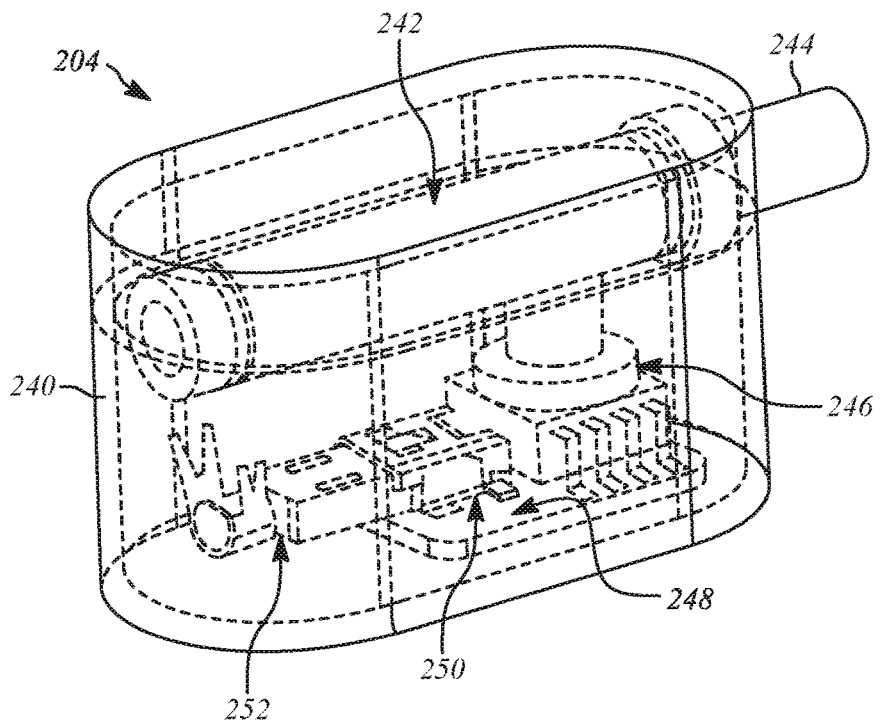
FIG. 10 illustrates an exemplary external unit depicting internal components including a fitting and a pressure sensor, depicted in phantom.

FIG. 10 illustrates an exemplary external unit depicting internal components including a fitting and a pressure sensor, depicted in phantom. In particular embodiments, an exemplary external unit 204 includes an external unit enclosure 240 having a flow fitting 242 in an interior cavity thereof. The flow fitting 242 may be connected to portions 206a and 206b of the connecting tubing 206, as illustrated for particular embodiments in FIGS. 7B, 8A and 8B. A second pressure sensor 246 may be mounted on a printed circuit board 248 and also within an internal cavity of the enclosure 240, and the output of the pressure sensor may be delivered to the controller 220 via a connective cable (not illustrated) which may be connected via a signal/power connector 250 and a mating signal-power connector 252, which may be a conventional USB port and plug. The connecting cable 206 may have dual lumens, as illustrated for particular embodiments in FIG. 9, where one of the lumens may be used to route a communications cable between the external unit and the base unit, while the other lumen accommodates fluid flow. In further embodiments, an external unit may house or be in communication with a pressure chamber, a fluid source, additional on-off valves, or some such combination.

By providing a first pressure sensor 224 in the base unit and a second, axially separated pressure sensor 246 in the external unit 240, the material flow rate through the connection tubing may be calculated in particular embodiments based upon measured differential pressure by the controller. The controller may analyze the pressure differentials and flow rate to determine the contents flowing through the aspiration catheter, connective tubing, or both.

In an exemplary embodiment, the controller characterizes the state of a catheter's contents as unrestricted flow, restricted flow, or clogged. In particular embodiments, a high pressure differential between spaced-apart pressure sensors indicates unrestricted flow that may be comprised of primarily healthy, clot-free blood, or blood free of vessel-obstructing clot. In some examples, healthy blood is blood with a low enough proportion of cross-linked fibrin such that it is not sufficiently integrated to cause ischemia or other similar vessel occlusions. Aspirating such healthy blood with full aspiration may result in excessive blood loss that may require the premature termination of the aspiration procedure. In another particular embodiment, a variable and intermediate or low pressure differential indicates restricted flow that may be comprised of clot, occlusive material, and blood. Such flow may benefit from full aspiration. In another particular embodiment, a small pressure differential or a pressure differential approaching zero may indicate a clog. Such flow, or lack thereof, may benefit from an extraction cycle. The use of differential pressure for detecting increased flow and occlusions, however, is exemplary and other flow measurement and material property measurement techniques may be available within the scope of particular embodiments.

Figure 11:
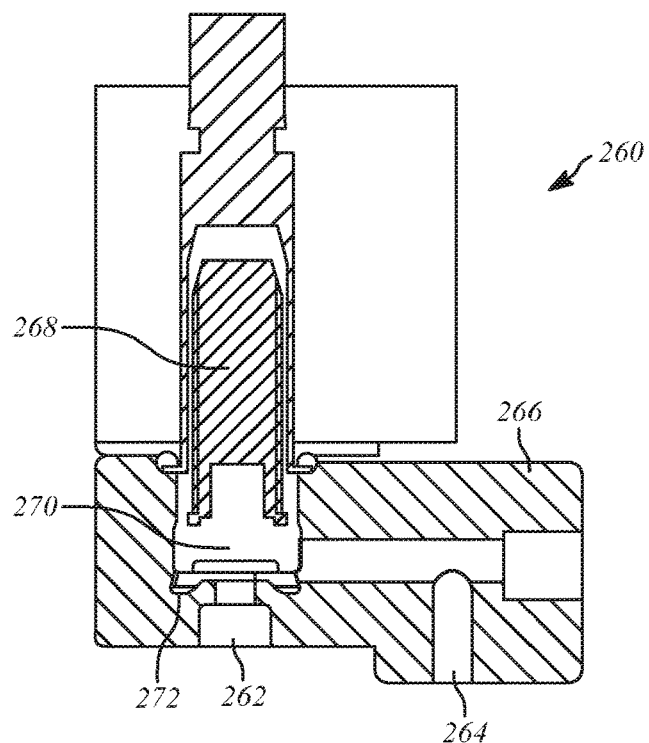
FIG. 11 illustrates an angle valve of the type which may be used as on-off valve in particular embodiments, depicted in section.

FIG. 11 illustrates an angle valve 260, depicted in section, of the type which may be used as on-off valve in particular embodiments instead of the pinch valve 228 illustrated in the base unit 200. The angle valve has a connector 262 for being secured to a connector on the vacuum canister (not illustrated) as well as a fitting 266 that may be connected to the connecting tubing 206 which is in turn connected to the aspiration catheter. A solenoid 268 is typically present to open and close valve stem 270 and valve seat 272. In particular embodiments, the valves may open to permit aspiration and close to block aspiration. Alternatively, the valves of particular embodiments may open to allow fluid to enter the aspiration tubing and/or aspiration catheter and close to block the fluid.

Figure 12:
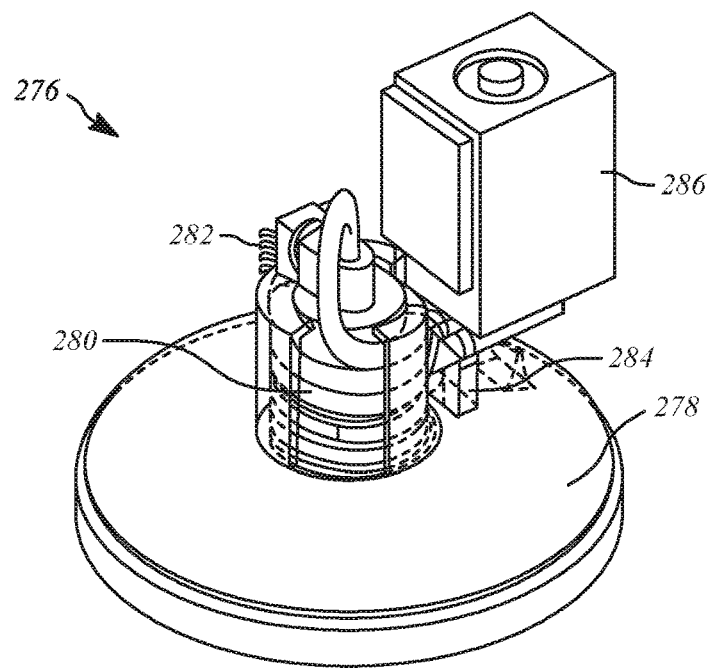
FIG. 12 is an isometric view of an angle valve connected to a coiled tube having pressure sensors at each end thereof mounted on a canister top.

FIG. 12 is an isometric view of an angle valve connected to a coiled tube having pressure sensors at each end thereof mounted on a canister top. In particular embodiments, the pressure sensors may be integrated into a single base unit 276 which may be fixedly attached to a canister cap 278. In this particular embodiment, a first pressure sensor 282 and a second pressure sensor 284 are attached to opposite ends of a coiled flow tube 280 so that differential pressure may be measured. An angled valve 286 may be secured directly to an outlet of the coiled flow tube 280 in order to provide for the desired on/off flow control.

In particular embodiments, the controller 220 in base unit 200 may implement an algorithm that receives and analyzes pressure sensor data to open and close the on-off valve, e.g. a pinch valve 228 (FIG. 9) or an angle valve 286 (FIG. 12) or 260 (FIG. 11). The algorithm receives and analyzes the pressure data input hundreds of times per second. The data are compiled to determine the diameter of the attached catheter, determine the contents flowing through the catheter and aspiration tubing, and to determine the flow rate.

In particular embodiments, the controller 220 implements an algorithm that uses pressure sensor data to analyze the contents flowing through an aspiration catheter and characterizes it as unrestricted flow, restricted flow, or clogged. A catheter with unrestricted flow is aspirating primarily healthy, clot-free blood, or blood free of vessel-obstructing clot. A catheter with mixed flow is aspirating a combination of clot, occlusive material, and blood. A catheter with little to no flow is clogged or occluded. If the algorithm determines that an excessive amount of blood is being aspirated, as is often the case for a catheter with unrestricted flow, it may restrict aspiration to reduce blood loss. If the algorithm determines that a catheter has restricted flow, it will typically allow full aspiration. If the algorithm determines that a catheter has little to no flow, it may initiate an extraction cycle to help remove any clogs or occlusions. As used herein, the term "clot" should be understood to encompass any occlusive material found in vasculature, such as thrombus, embolus, plaque, occlusive material, vessel blockage, or any other obstructive material. Clot references all such occlusive material for brevity's sake.

Figure 13:
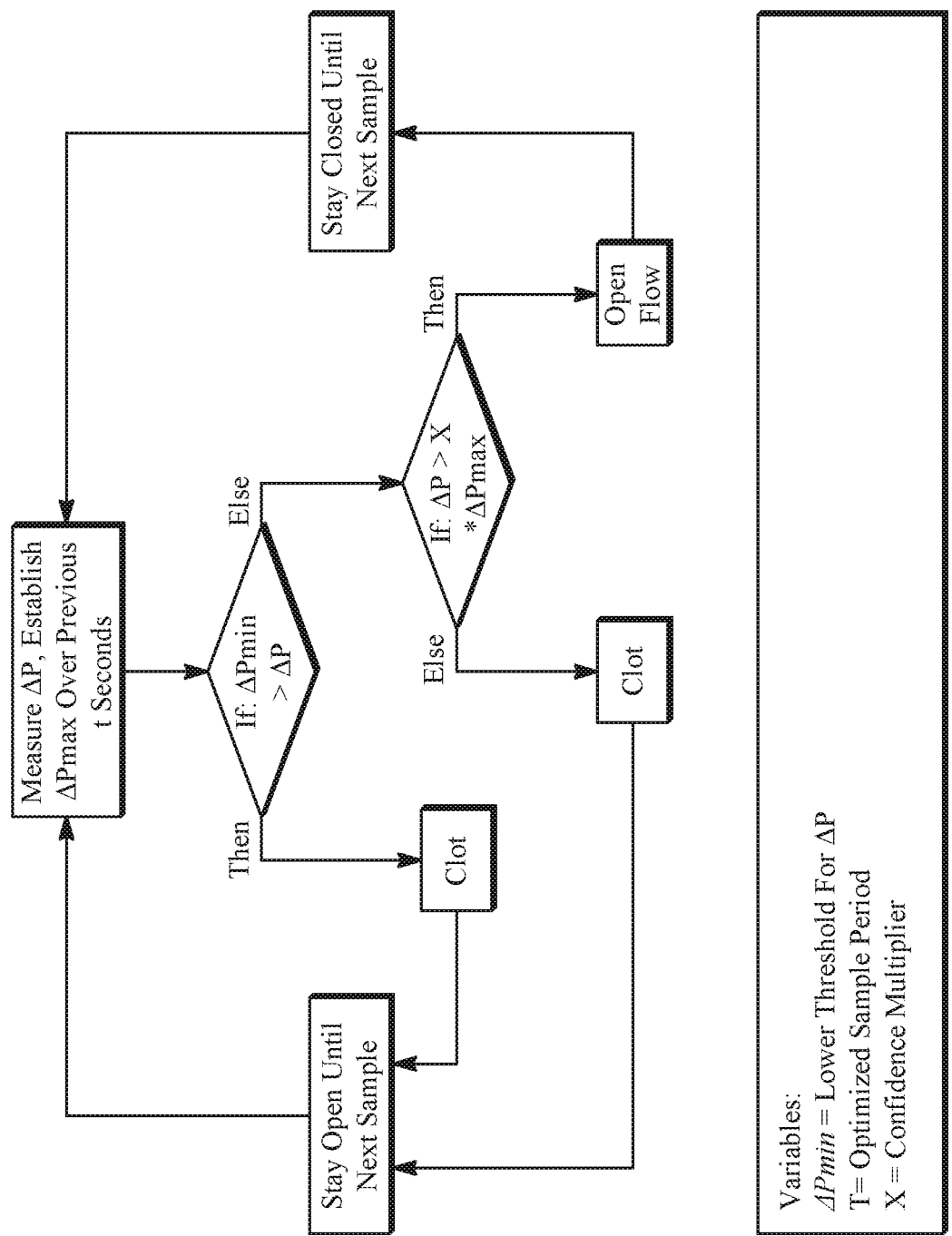
FIG. 13 illustrates an embodiment of an algorithm suitable for use with pressure differentials.

FIG. 13 illustrates an embodiment of an algorithm suitable for use with pressure differentials ("ΔP") to determine flowrate and, based on the determined flowrate, controls the on-off valves. In the illustrated algorithm logic tree, the first step is to measure max and minimum pressure differential windows over some assessment period and, after the assessment period, take an instantaneous pressure differential and compare it to these max and minimum pressure differential windows, which are incrementally updated. If the instantaneous pressure differential is lower than the minimum pressure differential of the assessment period, the algorithm determines that the system is in clot and instructs the system to continue full aspiration. On the other hand, if the instantaneous pressure differential is above the minimum pressure differential the algorithm determines whether the instantaneous pressure differential is above the product of the max pressure differential multiplied by a confidence interval, if it isn't the algorithm allows full aspiration, if it is the algorithm restricts aspiration to limit blood loss and enters a sampling state where aspiration is limited to brief surges to make new instantaneous pressure differential readings. In either case, whenever aspiration is allowed, the algorithm continually takes instantaneous pressure differential readings and compares them to the max and minimum pressure differentials collected throughout the procedure. In particular embodiments, when unrestricted flow (e.g. open flow) is detected the algorithm triggers a sampling state. In another particular embodiment, when a clot is detected the algorithm initiates full aspiration or initiates an extraction cycle with pulsed aspiration.

In particular embodiments, a correlation algorithm is utilized that determines whether a catheter has unrestricted flow, restricted flow, or is clogged, e.g. the catheter's state, based on a correlation between flow rate and such states. In particular embodiments, a windowing algorithm is utilized that analyzes discrete portions of pressure sensor data to establish local minimum and local maximum pressure sensor readings. These windowed minimums and maximums are compared to a global maximum and global minimum across the data set. Given a sudden large delta in pressure readings, the system preferentially makes determinations of a catheter's state according to local minimums and local maximums. Pressure readings below minimums and above maximums signify a change in catheter state, e.g. below a minimum indicates a clogged catheter and above a maximum indicates an unrestricted flow state.

In particular embodiments, an algorithm is utilized emphasizing an analysis of standard deviations across a discrete window of data points. The flow rate is compared to the average and mean flow rate. A small standard deviation indicates a catheter that is clogged or unrestricted, while a large standard deviation indicates a catheter that has restricted flow.

In particular embodiments, a learning algorithm is used to determine the contents flowing through an aspiration catheter. Training data is formed by collecting pressure readings along the length of catheter in a variety of states, e.g. unrestricted flow, restricted flow, or clogged. Numerous pressure readings are recorded for each catheter state, and the algorithm then references those data sets to interpret never seen pressure readings to predict what state the catheter is in.

In particular embodiments, an artificial neural network (ANN) is utilized that employs a multinomial logistic regression algorithm. The ANN is trained to predict answers by considering numerous training data sets. The training data includes both observed data as inputs and the actual outputs. The inputs are propagated across the ANN, which is comprised of layered nodes that each represent a linear transformation within the solution space. The ANN then "learns" by analyzing the difference between the ANN's calculated output and the actual output. This difference is translated into an error function. The error function is backpropagated across the ANN, whereby the weight of each node is modified according to its contribution to the error function. Weighting is a process of mathematical optimization that establishes which nodes optimally map inputs to their correct outputs. Numerous sets of training data are propagated across the ANN iteratively until the error function reaches convergence, i.e. some acceptable level of tolerance. Once the nodes have been properly weighted, in that the error function has reached convergence, the ANN may accurately predict the output of previously unseen input. Here, that means that the learned ANN may take novel pressure sensor data inputs and accurately predict catheter size and whether a catheter's contents should be classified as unrestricted, restricted, or clogged.

In particular embodiments, the algorithm employs semi-supervised and unsupervised learning to continually update node weights. The algorithm may employ clustering, dimensionality reduction, and reinforcement learning to further improve prediction accuracy. In preferred embodiments, the algorithm may accurately interpret pressure fluctuations associated with switching between catheters of different diameters and filter out pressure fluctuations generated by manual movements of a separator within the aspiration catheter by determining and accounting for the cadence of the movement. Additionally, particular embodiments may employ an algorithm that uses a combination of the above algorithmic flow analysis techniques.

In particular embodiments, the algorithm may initiate a sampling mode when unrestricted flow is detected. In exemplary embodiments, the algorithm may detect a change in flow indicating unrestricted flow within milliseconds. In one embodiment of the sampling mode, the algorithm will cycle off aspiration and then open and close the on-off valve at a predetermined frequency. The sampling state conducts an aspiration surge when the valve is briefly opened and makes an assessment of the pressure sensor readings. Based on this aspiration surge, the algorithm determines whether the system should revert to full aspiration, with the on-off valve in the open position or remain in the sampling state. These sampling surges occur over a millisecond order of magnitude and ensure that full aspiration occurs only when the system is engaging clot and thus minimizes blood loss.

In particular embodiments, the system is powered on and has a brief delay before the algorithm assesses flow in the aspiration tubing. If the sensors indicate unrestricted flow, then an appropriate delay of time is calculated for which the on-off valve remains shut. After this delay, the on-off valve opens to briefly allow aspiration and take a pressure reading sample in the aspiration tubing to assess whether the system still has unrestricted flow or if it has been positioned into clot or other occlusive material. If the sampling detects unrestricted flow, a new delay is calculated (in some instances, incrementally longer for each consecutive reading up to a threshold). If the sampling detects clot, e.g. restricted flow or a clog, an appropriate delay of time is calculated for which the valve remains open. While open, the system assesses pressure sensors readings at a regular frequency to determine whether the system has been positioned such to cause unrestricted flow. These processes repeat until the procedure is finished.

In particular embodiments, an extraction cycle may be useful to clear occlusions in an aspiration catheter or to facilitate the aspiration of clot that are large or otherwise hard to aspirate. An extraction cycle establishes pressure differentials between the aspiration catheter and the vacuum source to generate pressure pulses. In general, these pressure pulses may employ multiple mechanisms to facilitate thrombus ingestion into an aspiration catheter. In one mechanism, the pressure pulse introduces an acceleration component that facilitates the extraction of occlusive material. In another mechanism, the pressure pulse creates a force impulse that breaks static friction momentarily, allowing a lower dynamic friction to ingest thrombus. In yet another mechanism, the pressure pulse moves the thrombus away from the distal tip of the catheter and subsequently rapidly forces contact between the thrombus and the catheter, macerating the thrombus.

In particular embodiments, an extraction cycle may alternate between providing vacuum aspiration and relative positive pressure. An extraction cycle is typically initiated when an aspiration catheter is already under full vacuum. When an extraction cycle is initiated, the vacuum on-off valve between the catheter and the aspiration source is closed and the pressure in the aspiration catheter is increased, which may cause a positive pressure pulse and establish a pressure differential between the vacuum source and the catheter. When the on-off valve is then opened, the contents and the distal tip of the aspiration catheter experience the pressure differential as a negative pressure pulse that negatively impacts the structural integrity of any occlusions to a degree that a static force could only achieve with a greater supply of energy. The amplitude, or magnitude, of these pressure pulses are directly correlated to the pressure differential between an evacuated catheter and a pressure source (for positive pressure pulses) and a pressurized catheter and a vacuum source (for negative pressure pulses). The frequency with which the on-off valve opens and closes may be predetermined or responsive to pressure sensor data. An extraction cycle's pressure pulses may have an amplitude and frequency optimized to extract thrombus and similar occlusions from vasculature.

Pressure differentials in a catheter may be generated in a number of ways. In particular embodiments, pressure may be generated by closing off a catheter's access to the vacuum source. In particular embodiments, pressure may be generated by introducing fluid into the catheter, where the fluid is at a pressure between full vacuum and ambient pressure, at ambient pressure, at systolic pressure, or above systolic pressure (FIGS. 14-17). In particular embodiments, pressure differentials may be generated by mechanical displacement of a pressure chamber (FIG. 18).

In particular embodiments, an extraction cycle may be automatically initiated when an algorithm of the controller 220 detects a clogged catheter, an occluded catheter, or a catheter positioned in clot. A catheter may be identified as in clogged state when the pressure differentials approach zero. In particular embodiments, the controller automatically initiates an extraction cycle after the system has detected a clog lasting for more than 5 seconds. Alternatively, an extraction cycle is initiated, or terminated, on demand by a user. An extraction cycle may provide pressure pulses for a predetermined time period. Alternatively, in particular embodiments, an extraction cycle may assess pressure sensor data each time the on-off valve opens to assess flow and to determine whether the extraction cycle should continue or end. If an extraction cycle has trouble clearing a clog, it may vary the amplitude and frequency of the pressure pulses. In particular embodiments, an algorithm on the controller 220 consults a library of different pressure pulses and chooses from among the library. If a specific amplitude and frequency starts to clear the clog, the algorithm may continue to generate pressure pulses of that frequency and amplitude until the clog is cleared.

Figure 14:
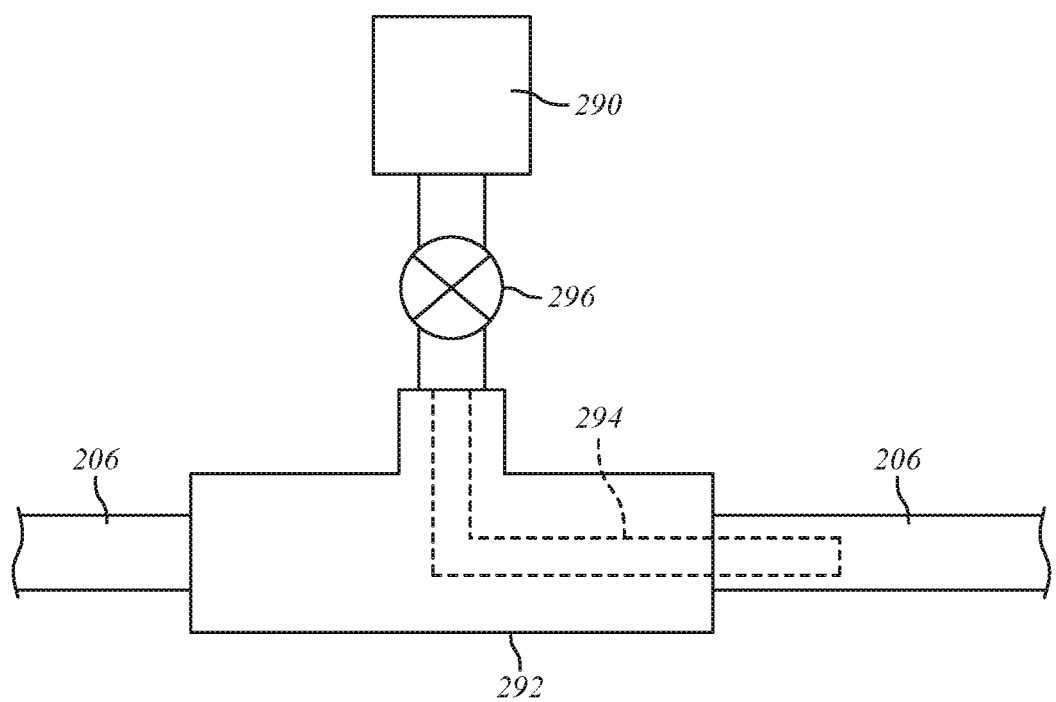
FIGS. 14-18 illustrate exemplary pulsed fluid injection assemblies suitable for use in particular embodiments.

FIGS. 14-18 illustrate exemplary pulsed fluid injection assemblies suitable for use in particular embodiments. FIG. 14 illustrates a fluid system that may be used in particular embodiments to generate pressure differentials, and thus pressure pulses. In this particular embodiment, a fluid introduction unit 290 is attached along a length of the connection tubing 206 with a three-point junction 292. The three-point junction 292 may be positioned between the base unit 210 and the external unit 204 or may be positioned distal to both the base unit 210 and the external unit 204—i.e. in close proximity to an attached aspiration catheter. A fluid injection on-off valve 296 controls the flow of fluid (either liquid or gas) to inject pulses of pressure into the clot flow path that may facilitate the extraction of clot or other occlusive substances. In particular embodiments, the flow of fluid is introduced directly into the connection tubing 206. In particular embodiments, the flow of fluid first traverses an injection tube 294 before entering the connection tubing 206. The injection tubing 294 may direct the pressure pulse towards the catheter, which may optimize the pressure pulse. In particular embodiments, the three-pint junction 292 has a T-joint structure as illustrated in FIG. 13. Alternatively, in particular embodiments, a three-point junction may have a Y-joint structure (not illustrated). The Y-joint may beneficially direct fluid from the fluid introduction unit towards the catheter, which may optimize the pressure pulse in a similar manner to the injection tubing of the prior example.

Figure 15:
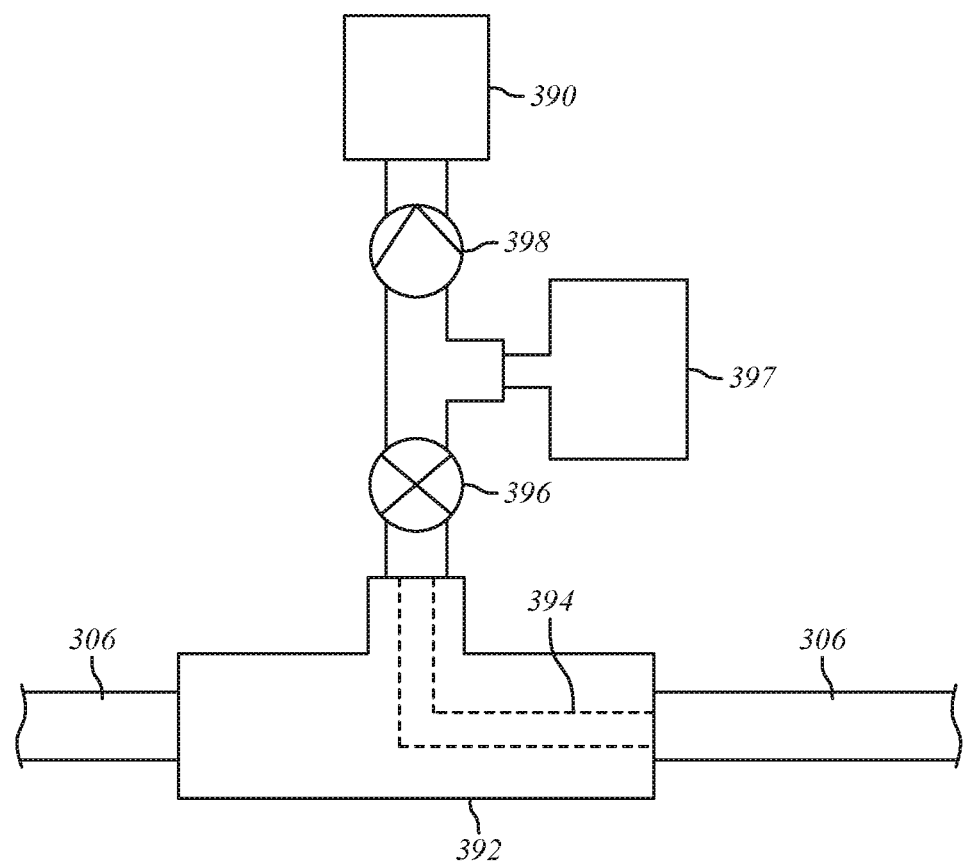

FIG. 15 illustrates an alternative fluid system that, in particular embodiments, uses a pump 398 that may be connected between a fluid reservoir 390 and an injection valve 396. In one embodiment, the pump 398 cycles on when the injection valve 396 opens. The pump provides work by forcefully injecting fluid from a fluid reservoir 390, through the injection on-off valve 396, into an injection tube 394 and/or connection tubing 306. In particular embodiments, the magnitude of the positive pulse of pressure is directly correlated to the throughput (e.g. size) of the pump 398. In particular embodiments, a pressure chamber 397 is positioned between the pump 398 and the injection valve 396. A pressure chamber 397 allows the pump 398 to provide work even when the injection valve 396 is closed. While the injection valve 396 is closed, the pump 398 forcefully injects fluid from the reservoir 390 into the pressure chamber 397, whereby the pressure chamber 397 becomes pressurized. When the injection valve 396 opens, pressure is released from the pressure chamber 397 into the injection tube 394 and/or connection tubing 306. In this embodiment, since the pump 396 may build up pressure over time, the magnitude of the positive pulse of pressure is not directly correlated to the throughput (e.g. size) of the pump 398, thus this embodiment allows for a smaller pump. To provide even greater control over the duration or magnitude of positive pressure pulses, in particular embodiments, the opening and closing of the injection valve may be throttled or manipulated to modulate rate of injection. In particular embodiments, a pressure sensor may be included in pressure chamber 297 to monitor and control the buildup of pressure.

Figure 16:
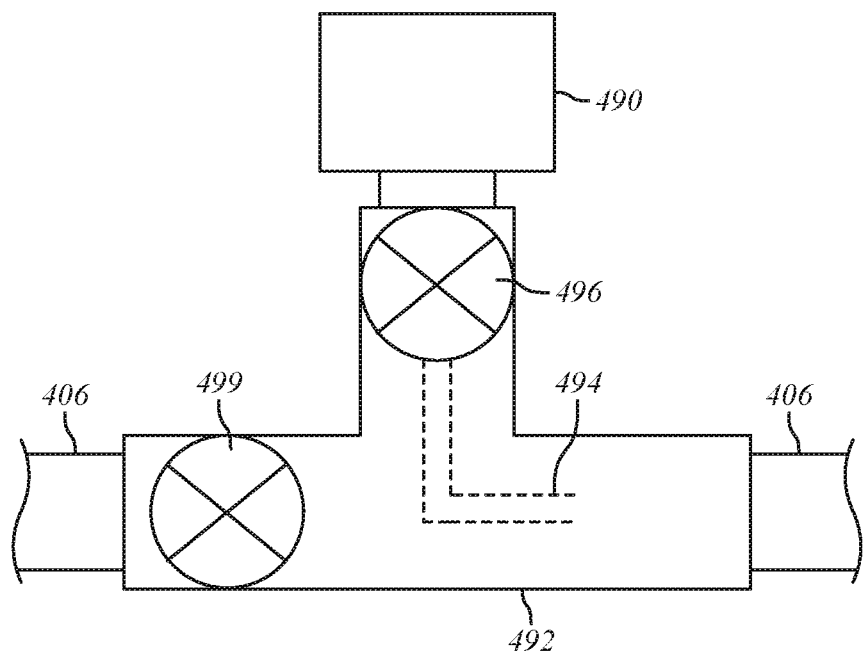

FIG. 16 illustrates another three-point junction 492 attached along connection tubing 406. In particular embodiments, the three-point junction 492 may be positioned between the base unit 210 and external unit 204 or may be positioned distal to both the base unit 210 and the external unit 204. A pressure valve 496 controls the generation of positive pulses of pressure from fluid chamber 490. Fluid from the fluid chamber 490 may flow directly into connection tubing 406 or may first traverse an injection tube 494 before entering the connection tubing 406. An aspiration valve 499 controls the application of vacuum aspiration from an attached vacuum source. In particular embodiments, the three-point junction 492 has valves to control both vacuum forces and positive pressure pulses. This allows the three-point junction 492 to alternate between applying vacuum aspiration and pulses of pressure, wherein the pressure is above that of the vacuum source. In particular embodiments, the aspiration valve 499 and the pressure valve 496 may be opened alternatively, simultaneously, with a delay, or in some overlapping sequence. In one overlapping sequence, one valve starts to open when the other valve is starting to close, whereby there is a brief period where both valves are at least partially open. In other overlapping sequences, sometimes both valves are open and both valves are closed for at least short periods of time.

In particular embodiments, an aspiration valve 499 is positioned between a catheter and an aspiration source to modulate aspiration and a pressure valve 496 is positioned between the catheter and fluid source to modulate fluid injection. In particular embodiments, both aspiration valve 499 and pressure valve 496 may be selectively opened and closed to create pressure differentials within the catheter and/or aspiration tubing that may result in pressure pulses of a desired amplitude and frequency.

Figure 17:
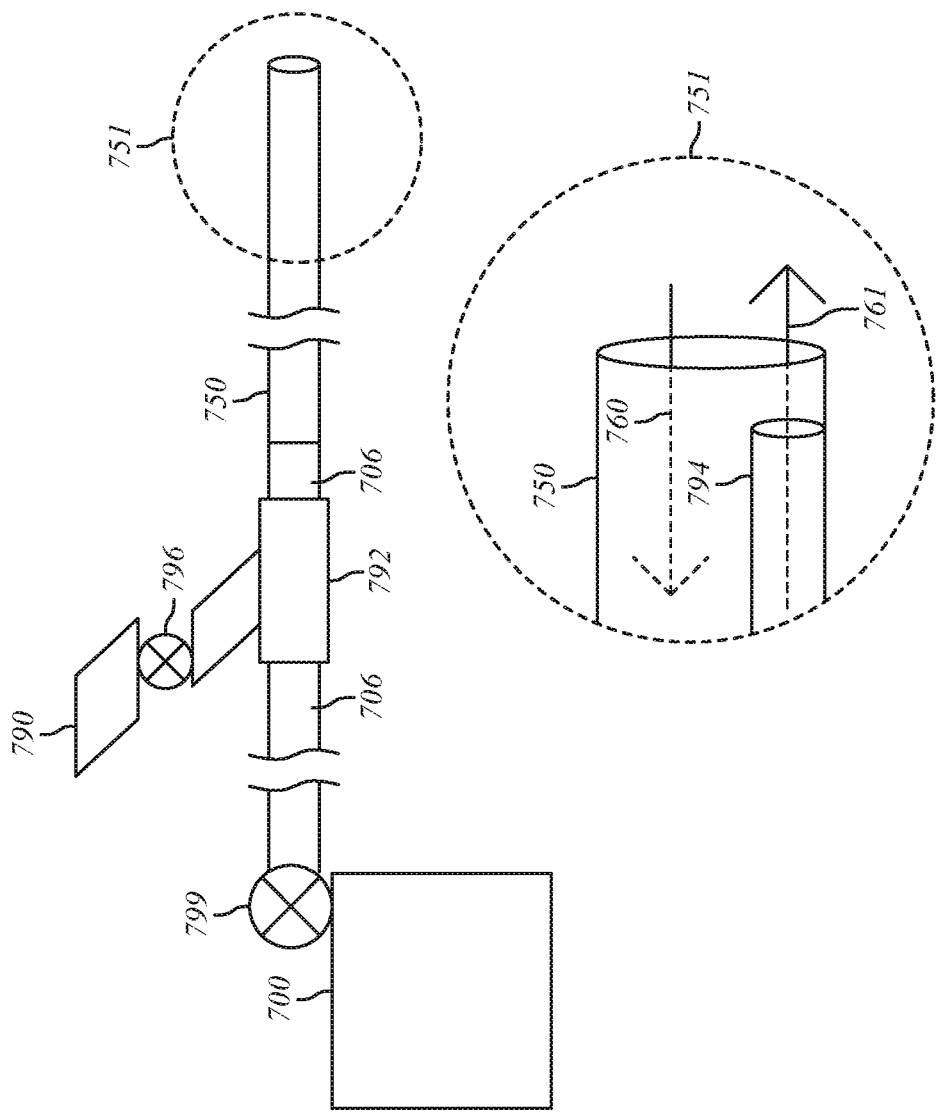
Figure 18:
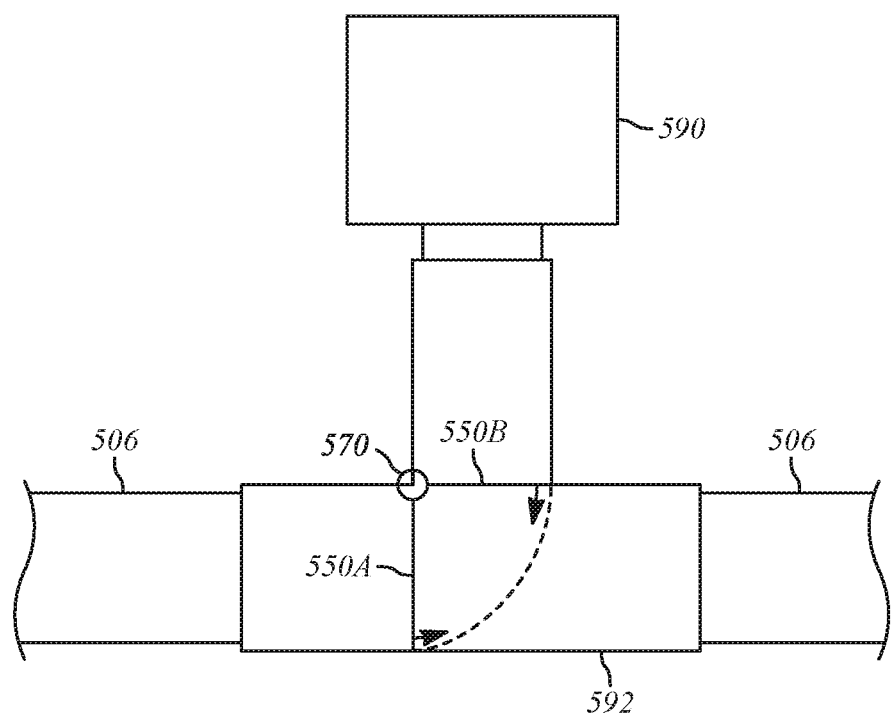

FIG. 17 provides a perspective view of a three-way joint and the components it connects. In particular embodiments, a connection tubing 706 acts as a common conduit between a vacuum source 700, a pressure source 790, and an aspiration catheter 750. The connection tubing 706 may have a first end configured to attach, or be placed in fluid communication with, the vacuum source and a second end configured to attach, or be placed in fluid communication with, the aspiration catheter. In particular embodiments, the second end is attached to the aspiration catheter with a rotating hemostasis valve. A three-way joint 792 may be positioned proximate to the second end to provide pulses of relative positive pressure near the aspiration catheter 750. In particular embodiments, the three-way joint 792 is an angled joint or Y-joint, whereby fluid from the pressure source is directed towards the aspiration catheter 750. In some particular embodiments, the three-way joint 792 includes injection tubing 794, which directs fluid from the pressure source towards the aspiration catheter 750. In particular embodiments, the injection tubing 794 extends from the three-way joint into the aspiration catheter, whereby fluid flows from the pressure source into the aspiration catheter 750. In another particular embodiment, the injection tubing 794 extends from the three-way joint to a position proximate a distal end of the aspiration catheter, as depicted in perspective 751, which provides a zoomed-in perspective of the distal end of the aspiration catheter 750. In particular embodiments, the pressure source may cause fluid to flow according to directional arrow 761 and the vacuum source may cause fluid to flow according to directional arrow 760. In particular embodiments, the controller may modulate a vacuum valve 799 and a pressure valve 796, whereby the closing of the vacuum valve 799 and the opening of the pressure valve 796 may result in a relative increase in pressure at a distal tip of an aspiration catheter.

Alternatively, in particular embodiments, the opening of the vacuum valve 799 and the closing of the pressure valve 796 may result in a relative decrease in pressure at the distal tip of the aspiration catheter 750. In particular embodiments, these changes in pressure are transmitted along a length of the aspiration catheter as a pressure pulse. In particular embodiments, a controller may close vacuum valve 799 and open pressure valve 796 for a small period of time, thus allowing a minimal volume of fluid from the pressure source 790 to be introduced into a proximal end of aspiration catheter 750 to increase the relative pressure at a distal end of the aspiration catheter 750 before reverting to vacuum by re-opening vacuum valve 799 and closing pressure valve 796.

Similarly, in particular embodiments, a controller may close vacuum valve 799 and open pressure valve 796 for a longer period of time, allowing a larger volume of fluid from the pressure source 790 to be introduced into the aspiration catheter 750 to facilitate movement of obstructive material away from the distal end of aspiration catheter 751 before reverting to vacuum by re-opening vacuum valve 799 and closing pressure valve 796. In particular embodiments, the connecting tubing 706 may have a dual lumen along a portion of its length, whereby one lumen accommodates fluid and a second lumen accommodates wiring, which enables the controller to modulate both the vacuum valve 799 and the pressure valve 796.

FIG. 18 illustrates a valve structure that controls both aspiration forces and positive pressure pulses. In particular embodiments, a three-point junction 592 attaches to connection tubing 506 and pressure chamber 590. A gate valve 550 translates at axis 570 to block aspiration in a 550A position and to block fluid introduction in a 550B position. The gate valve 550 may provide pulsed aspiration by oscillating back and forth at a predetermined or responsive frequency as controlled by an algorithm in the controller 220. In particular embodiments, the three-way gate valve exists at the juncture between the aspiration source, the pressure source, and the catheter. The gate valve 550 translates between blocking the aspiration source and blocking the pressure source to effect pressure pulses of a desired amplitude and frequency.

In particular embodiments, fluid injection does not occur at a three-point juncture, but rather occurs at a more distal region closer the catheter tip. The location of the relative pressure injection may be used to optimize the pressure pulse variation in order to facilitate clot removal. In one embodiment, a distal region of an aspiration catheter includes a valve that may be opened and closed, e.g. the distal valve. In particular embodiments, an aspiration valve is closed, and the distal valve is opened to allow blood to rush into the catheter, which increases the pressure in the catheter and amplifies the pressure differential between the catheter lumen and the vacuum source. Typically, the distal valve is then closed, and the aspiration valve is opened, wherein the pressure differential between the vacuum source and the catheter results in a pressure pulse. In another embodiment, fluid is transferred into an aspiration catheter from another adjacent catheter. For instance, an inner catheter may deliver fluid to an outer aspiration catheter. In particular embodiments, an outer catheter may deliver fluid to an inner aspiration catheter through a valve structure. In either case, the fluid is delivered along the length of the aspiration catheter, rather than through a proximal end. In a similar manner, in particular embodiments, an adjacent catheter may offer an additional connection to a vacuum source.

Figure 19:
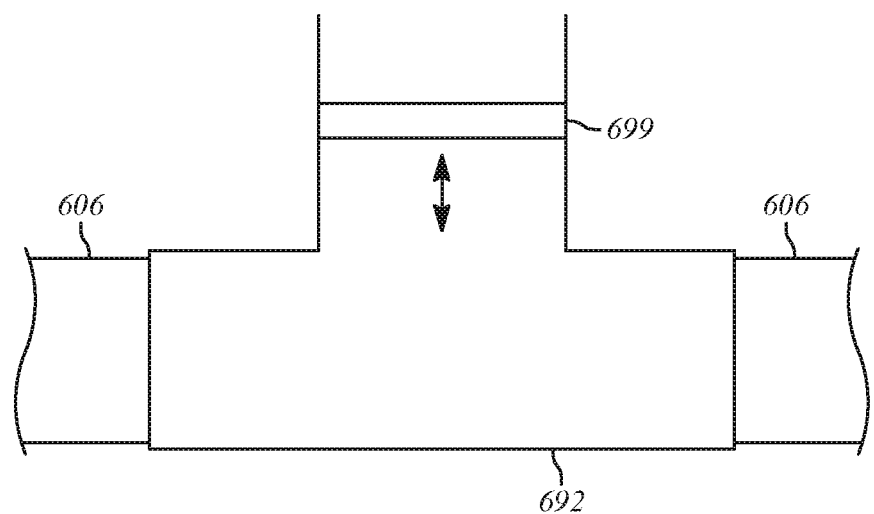
FIG. 19 illustrates a mechanical displacement assembly for manipulating pressure in particular embodiments.

FIG. 19 illustrates a mechanical displacement assembly for manipulating pressure. In particular embodiments, a mechanical piston 699 may replace the previous embodiment's injection valves, pressure chambers, pumps, and fluid reservoirs. The stroke of the piston 699 or alternative mechanical device may be controlled to adjust the volume of the catheter resulting in the generation of negative pressure on one stroke and the generation of positive pressure on the other stroke. In general, a mechanical actuation device actuates back and forth to increase and decrease the overall volume of the system. When the device actuates to increase volume, pressure decreases, and when the device actuates to decreases volume, pressure increase. These pressure changes may create, amplify, or assist pressure pulses of an extraction cycle. In particular embodiments, the piston 699 may be provided in a three-point juncture 692 that attaches to connection tubing 606. Other mechanical means of controlling volume, or pressure, of the catheter include linear motors, stepper/servo motors, cam follower actuators, solenoids, audio exciters, voice coil actuators, diaphragms, peristaltic pumps, rotary vanes, gears, screws, syringes etc. (not pictured).

In particular embodiments, high frequency pressure pulses may be enabled by a mechanical method, such as that illustrated in FIG. 19. To provide high frequency pressure pulses, a catheter must be rapidly pressurized and rapidly evacuated. In particular embodiments, the fluid injection systems of FIGS. 14-18 may readily provide a rapid influx of pressure; however, it may take a non-insignificant amount of time for the vacuum source to bring that catheter back to full vacuum. If the next influx of pressure occurs too early, the catheter will not have had time reach full vacuum, or near full vacuum. In this scenario, the pressure differential between the not-quite-evacuated catheter and the pressure source will be lower and the resulting pressure pulses will have a lower amplitude, which may be suboptimal in some scenarios. In particular embodiments, to avoid low amplitude pressure pulses caused by a high frequency, a vacuum recovery system may be utilized to reduce the time required to return a catheter to full vacuum after an influx of positive pressure. With a vacuum recovery system, pressure pulses may be enabled with both a high amplitude and a high frequency.

FIG. 19 additionally illustrates a device that may function as a vacuum recovery system by generating pressure differentials. In particular embodiments, a vacuum recovery system may utilize a syringe, an evacuated chamber, a second aspiration pump, or some combination of these options. A syringe is a piston actuated device that retracts to increase a system's volume (and thus decrease pressure) and advances to decreases a system's volume (and thus increase pressure). A syringe-like device may beneficially assist not only vacuum recovery but also positive pressure pulse generation. In particular embodiments, a syringe is used during an extraction cycle. In such an embodiment, a catheter starts at full vacuum. The vacuum source closes, the syringe advances (to reduce system volume), and, optionally, fluid is injected, which all facilitates the formation of a positive pressure pulse. Next, the vacuum source opens, and the syringe retracts (to increase system volume) to generate a negative pressure pulse, whereby the syringe speeds the catheter's return to near full vacuum. In particular embodiments, an aspiration pump is configured to selectively prime an evacuated chamber that is opened to the catheter, in addition to an aspiration pump, after each pressure pulse. Together, the aspiration pump and the evacuated chamber more rapidly return a catheter to full vacuum. While the aspiration pump is closed to the catheter, it may be opened to the evacuated chamber to further prime the evacuated chamber between pressure pulses. In particular embodiments, a secondary aspiration pump assists a primary aspiration pump to facilitate vacuum recovery after each pressure pulse.

Figure 20:
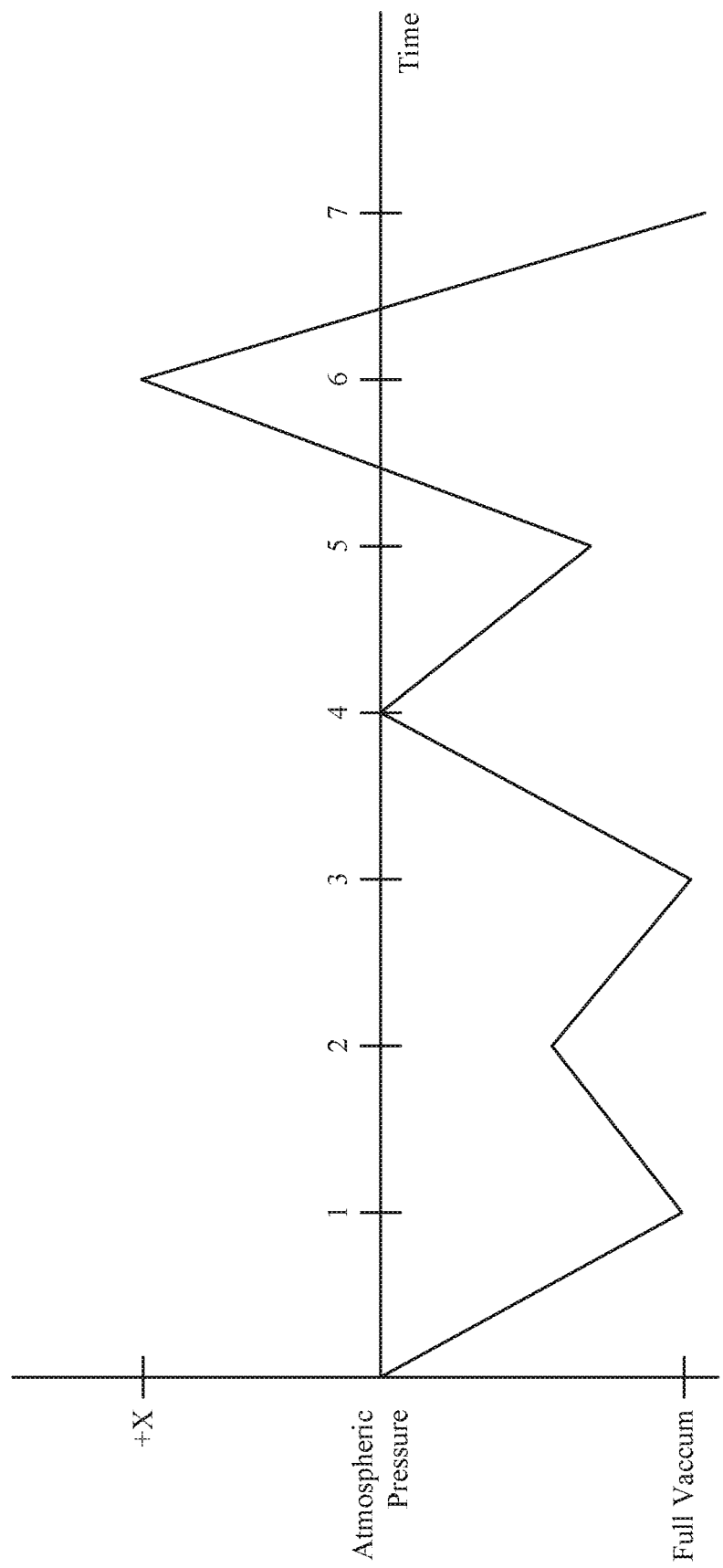
FIG. 20 illustrates a graphical representation of a particular embodiment of pulsed aspiration, where catheter internal pressure is varied over time.

FIG. 20 illustrates a graphical representation of a particular embodiment of pulsed aspiration, where catheter internal pressure is varied over time. An extraction cycle may use a pulsation protocol to systemically manipulate the amount of pressure within a catheter to facilitate the extraction of occlusive material. Pressure in a catheter may be manipulated by a variety of methods. For instance, vacuum aspiration may be used to reduce pressure within the catheter and the removal of vacuum suction and/or the introduction of fluid may be used to increase pressure within the catheter. In other instances, a mechanically actuating device may alternate between increasing and decreasing pressure within a catheter. In particular embodiments, illustrated by FIG. 20, at time 0, the catheter has not been subjected to any suction forces and is at atmospheric pressure. From time 0 to time 1, the catheter has lost pressure, lunging from atmospheric pressure to near full vacuum (i.e., near −29.9 inHg). From time 1 to time 2, the catheter has gained pressure, which decreases vacuum strength. From time 2 to 3, the catheter has lost pressure, which returned the catheter to near full vacuum. From time 3 to 4, the catheter has gained pressure and returned to ambient pressure. From time 4 to 5, the catheter has lost pressure, again lunging from atmospheric pressure to near full vacuum. From time 5 to 6, the catheter has gained pressure, which caused the pressure to surge from near full vacuum to above ambient pressure. From time 6 to 7, the catheter has lost pressure, lunging from a pressurized state above atmospheric pressure to near full vacuum.

A pulsation protocol of the nature illustrated in FIG. 20 may be executed once or may be repeated several times. In particular embodiments, the pulsation protocol may include additional time periods with additional pressure variations and pressure patterns. In general, the system's pressure may vary from between near vacuum to above average systolic pressure. The duration of the pulsation protocol may be predetermined or adaptive to pressure sensor readings. In particular embodiments, the controller may prolong or shorten a pulsation protocol based on pressure sensor readings. In some particular embodiments, the system may remain at a stable pressure state across one or more time periods. For instance, the controller may cause the system to dwell at near full vacuum. The dwell time in each pressure state and the frequency with which the system transitions between pressure states may be optimized to ingest different clot or occlusive material compositions. Although FIG. 20 illustrates a pulsation protocol with a stable and consistent frequency, in other particular embodiments the frequency of a pulsation protocol may be variable or some combination of partially stable and partially variable. High amplitude (or high magnitude) pressure pulses may be generated by generating large pressure differentials. For instance, FIG. 20 illustrates a high amplitude pressure pulse between times 5 and 7. In particular embodiments, lower magnitude pressure pulses may be generated by oscillating between less extreme high pressures and low pressures. For instance, the low end of the pressure pulse may not reach near full vacuum, the high end of the pressure pulse may not reach ambient pressure, or both, thereby resulting in a lower magnitude pressure pulse, which may be desirable in some scenarios. The time units of FIG. 20 may be in second, milliseconds, microseconds, or the like.

In some particular embodiments, an extraction cycle uses a predetermined series of pressure pulses with near full vacuum aspiration before the extraction cycle, between individual pulses of relative positive pressure, and after the extraction cycle. The pressure pulses may be selected from a library of pressure pulses having amplitudes and frequencies that facilitate the extraction of clot and other occlusive material. A series of pressure pulses may vary from one another in terms of frequency, amplitude, or both. For instance, a pulsation protocol may use a series of pressure pulses with a trend where one of the amplitude or frequency rises while the other diminishes, where both the amplitude and frequency rise or diminish, or where one of the amplitude or frequency rises or diminishes while the other remains constant.

In particular embodiments, an extraction cycle provides specific pressure pulses based on pressure sensor readings. One such responsive extraction cycle measures pressure within the catheter and then selects one or more pressure pulses optimized for a catheter with those pressure readings. In another responsive extraction cycle, the system may cycle through a library of pressure pulse protocols, with time periods of static or full aspiration and occlusion detection after each individual pressure pulse. After the library has been cycled, the system may repeat the pressure pulses that were measured to be most successful. The degree of success of a specific pressure pulse is typically commensurate with the amount of increased flow rate after the pressure pulse. The system may continue to cycle down until only a few pressure pulse protocols are in the loop. If the efficacy of the loop begins to diminish, the system may return to the full library and start a fresh cycle.

In particular embodiments, a responsive extraction cycle may have three modes: Cycling up, where successive pressure pulses are stronger in terms of amplitude and/or frequency, cycling down, where successive pressure pulses are weaker in terms of amplitude and/or frequency, and maintenance pressure pulses, where pressure pulses have a consistent frequency and amplitude. When the system detects a clogged state, it enters the cycling up mode. When the system detects restricted flow state, it enters the maintenance mode. When the system detects an unrestricted flow state, it enters the cycling down mode. In this way, the system trends towards pressure pulses with an amplitude and frequency that facilitates restricted flow, which is beneficially removing clot and other occlusive material.

In situations where maximizing the removal of occlusive material eclipses concerns of blood loss, such as in neurovascular stroke procedures, an alternative embodiment may be useful. Under these circumstances, in particular embodiments, an optimal technique may include positioning the distal end of a catheter in clot, applying full vacuum, and waiting a predetermined period of time before advancing to a next step. The objective may be complete or nearly complete catheter tip engagement of a mass of occlusive material, engagement which essentially clogs the distal end of the catheter and is sometimes referred to as "corking the catheter". If a clinician has successfully "corked the catheter", the catheter system may be removed from the vessel, withdrawing the mass of clot or occlusion with it. Alternatively, in particular embodiments, an extraction cycle may be used to draw an occlusion through the catheter lumen or cause the clot to become deeply latched, or corked, within the catheter. After the completion of the extraction cycle, in particular embodiments, the clot may be removed or corked in the attached catheter so that the catheter together with the clot may safely be removed from the patient.

In particular embodiments, an extraction cycle may automatically stop or be manually stopped when a clot or other occlusive material clogs a catheter and corks it. For instance, the clot or occlusive substance might be too large or tough to traverse an aspiration catheter, but nonetheless become partially entrained in the aspiration catheter. In particular embodiments, the system may transition to full aspiration to allow the user to remove the corked catheter while dragging the clot or occlusive material out with the catheter. In some instances, once an extraction cycle is initiated, the clot or occlusive material may still clog the catheter. In particular embodiments, the controller may then revert to full aspiration and notify the user of the corking event, whereby the system may prompt the user to remove the catheter. In particular embodiments, the user may manually turn off an extraction cycle, causing the system to return to full vacuum, and remove the catheter.

In particular embodiments, the system may transition to a maceration cycle to allow a valve, such as a pinch valve or a different type of valve, to apply mechanical forces on a clot or other occlusive material. Such mechanical action may be applied to sufficiently modify the form and/or consistency of a clot or other occlusive material to enable more effective aspiration.

To indicate that particular embodiments are doing work to remove clots or other occlusive material, one embodiment may include visual and/or auditory signals that indicate the progress of a given extraction cycle. In particular embodiments, the start of an extraction cycle is signaled by a flashing blue light, which flashes until the cycle is completed, and, at completion, the light turns to green to indicate completion. In particular embodiment, base unit 216 may include a light bar. The light bar fills up incrementally, whereby the light bar progressively "fills up" with light in proportion to the cycle's progress. Alternatively, base unit 216 may include a small screen for displaying images. The small screen may display an animation indicative of loading. Loading animations may execute a repetitive pattern (e.g. spinning circular object) or may execute a single cycle of a prolonged animation (e.g. slowly filling circle). Either in conjunction with visual progress indication or as an alternative to visual progress indication, the system may use auditory cues in particular embodiments to signify the extraction cycle's initiation, pulsating phase, and completion. Such auditory cues may include musical notes, beeps, and/or speech. Auditory cues may include updates (e.g. "extracting") or suggestions (e.g. "advance/retract the catheter").

In particular embodiments, an algorithm may also control a lighting mechanism, e.g. indicator light 210 (FIGS. 7A and 7B), to convey to the user whether the system is in a full aspiration state, an unrestricted flow state, a restricted flow state, a clogged state, a sampling state, or an extracting state. Specific lights may be illuminated to indicate bubbles or that the override switch has been triggered. In particular embodiments, the algorithm may control a piezo acoustic chip that conveys audible information to the physician regarding the state of the effluent and override switch. In one embodiment, the piezo is a surface mounted 4 kHz single tone at 65 dB at 10 cm. The signals may include sounds and phrases such as tone/pitch changes, beeping patterns, "clogged", "occluded", "clot", "blood", "open flow", etc. Particular embodiments utilize a dynamic beeping cadence, where a beeping pattern is steadily increased when an unrestricted flow state is increasing in duration. The speed of the beeps indicates the length of time the system has been in unrestricted flow, alerting the physician to the increasingly problematic nature of the system's positioning. In particular embodiments, the system may also include a multi-position switch or button to specifically activate different algorithms, mute audio cues, or to prime the system with fluid. Such a feature could be activated by inserting a pin in the base unit 210, which will activate this customizable feature.

In particular embodiments, the system may be manually powered on and conduct aspiration for a predetermined period of time. If the system detects unrestricted flow, then the on-off valve is turned off to stop flow. The attending physician then must reposition the catheter tip into clot and manually trigger a mechanism (such as a foot pedal or manual switch) to initiate further aspiration. This manual trigger may override the algorithm and allow aspiration to continue. Once the manual trigger is released, the algorithm may again monitor flow to allow aspiration so long as the flow is acceptable. In particular embodiments, if and when the system again detected unrestricted flow, the on-off valve may again be closed until the physician were to reposition the aspiration catheter and manually override the controller. This protocol may be repeated until the physician completes the procedure.

In particular embodiments, before an aspiration catheter can be used to remove clot and other occlusive material, it may need to be primed with an incompressible fluid. In particular embodiments, a catheter may be filled with saline fluid to remove all the air from the lumen of the catheter. In particular embodiments, a catheter is automatically primed, whereby the catheter is filled with fluid to expel all compressible fluids (e.g., air). In particular embodiments, the sensors may monitor catheter contents during use. If compressible fluids are detected (e.g., bubbles), the system may alert the user. In particular embodiments, the system may indicate that the procedure needs to stop so that the catheter may be again primed to remove the air bubbles.

Dynamic System State Detection

Figure 21:
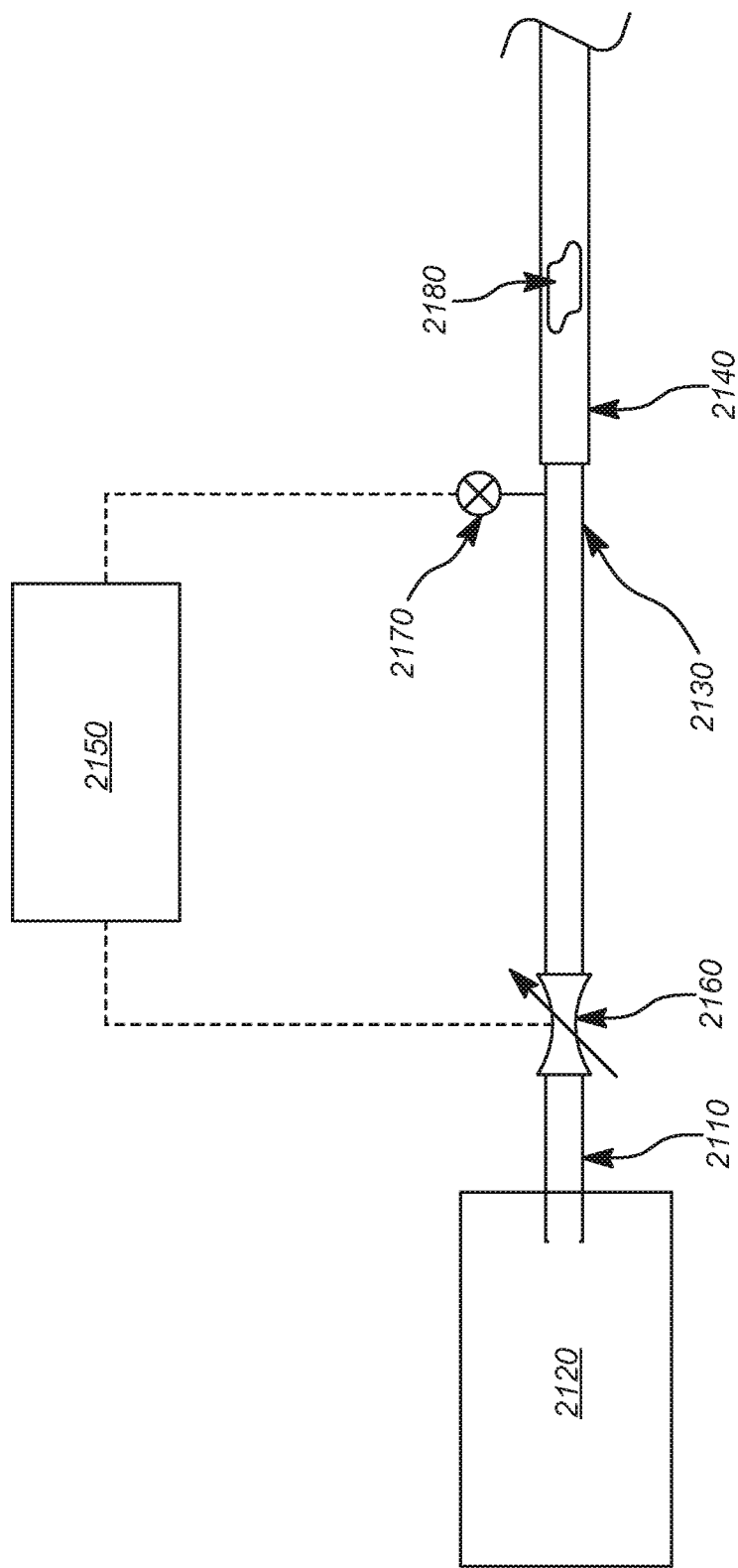
FIG. 21 is a schematic representation of a particular embodiment configured for dynamic system state detection.

FIG. 21 is a schematic representation of a particular embodiment configured for dynamic system state detection, illustrating an alternative approach for detecting one or more system states such as unrestricted flow or occluded flow in the aspiration catheter. The proximal end of connection tubing 2110 may be connected in fluid communication with a vacuum source 2120. The distal end 2130 of the connection tubing may be connected in fluid communication with the proximal end of aspiration catheter 2140. In FIG. 21, the distal end of the aspiration catheter is truncated, i.e., not illustrated in the schematic.

In particular embodiments, the controller 2150 may selectively open and close vacuum valve 2160 to control fluid communication or corresponding isolation of the connection tubing relative to the vacuum pressure of the vacuum source. Based on the parameters used for operating the vacuum valve, such as the number, sequence, frequencies, and/or duty cycles of triggering the open/closed valve states, many operational states of operating the vacuum valve are possible. A distal pressure sensor 2170 may be located proximate the distal end of the connection tubing. In particular embodiments, an external unit, such as a unit previously described and illustrated in FIGS. 8A, 8B, and 10, may be present as a connecting module between the distal end of the connection tubing and the proximal end of the aspirating catheter. In particular embodiments, the external unit may additionally comprise the distal pressure sensor.

In particular embodiments, the controller may operate the vacuum valve to generate one or more pressure level changes in the connection tubing, and thereby into the contents of the connection tubing and/or the aspiration catheter system. Further, the controller may detect pressure levels at the distal end of the connection tubing using the distal pressure sensor, wherein changes in the detected pressure levels are correlated with the pressure level changes generated by operating the vacuum valve.

In particular embodiments, based on the detected pressure profile, wherein a profile comprises a time-dependent sequence of detected pressure levels, the controller may dynamically determine one or more system states in the aspiration catheter and/or connection tubing. Based on the determination of one or more flow states, the controller may further initiate one or more actions.

The generalized approach of the specific implementation of FIG. 21 and as discussed above may be considered dynamic detection of system states. Some particular embodiments of this approach will be further discussed herein. It should be appreciated that specific implementations of dynamic detection of system states may vary across embodiments, and may be tailored based on particular configurations and applications.

Figure 22:
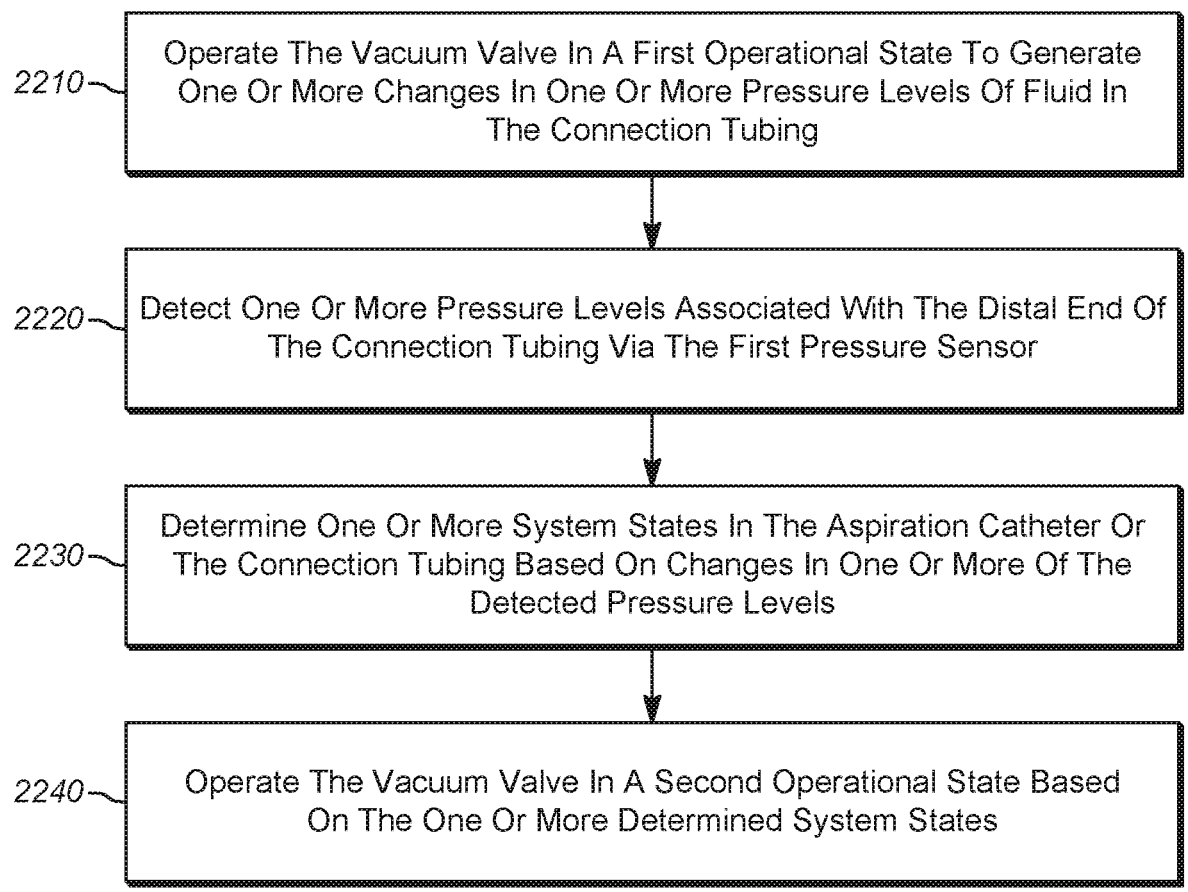
FIG. 22 illustrates a particular embodiment of an algorithm suitable for implementing dynamic system state detection in an embodiment.

FIG. 22 illustrates a particular embodiment of an algorithm suitable for implementing dynamic system state detection and detecting system states in the aspiration catheter or the connection tubing of an aspiration thrombectomy system. In a first step 2210 of the illustrated algorithm, the controller may generate one or more pressure level changes in the connection tubing by operating the vacuum valve in a first operational mode, such as by selectively opening and closing the vacuum valve. In a second step 2220, the controller may detect one or more pressure levels associated with the distal end of the connection tubing via the first pressure sensor. In a third step 2230, the controller may determine one or more system states in the aspiration catheter or the connection tubing based on changes in one or more of the detected pressure levels. In a fourth step 2240, the controller may operate the vacuum valve in a second operational state based on the one or more determined system states.

In particular embodiments or cases, based on the system state inferred to exist in the aspiration catheter or connection tubing based on the detected pressure profile, the controller may determine that no additional vacuum valve operation is immediately required. For instance, the controller may generate a pressure level change in the connection tubing by opening, and then closing, the vacuum valve. In particular embodiments, if the controller were to subsequently determine that presence of unrestricted or open flow in the aspiration catheter, it may continue to keep the vacuum valve closed, until the next action step is required.

System states may comprise qualitative and/or quantitative descriptions of flow states within the aspiration catheter and/or connection tubing. In particular embodiments, the flow state may be an unrestricted or open flow state, wherein the distal end or tip of the aspiration catheter may be in contact with healthy blood, and there may be little or no occlusive material in the catheter and/or connection tubing. In particular embodiments, an occluded flow state may exist in the aspiration catheter, such as due to a clot 2180 of FIG. 21. As will be further discussed, in particular embodiments, flow states may also include "in-between" states, such as partially occluded flow, which may require specific action(s) to follow determination of that system state.

System states may further comprise qualitative and/or quantitative descriptions of the presence of specific fluids and/or other materials in the aspiration catheter and/or connection tubing. In particular embodiments, the presence or absence of a flushing or priming fluid, such as saline, may define one or more system states. In particular embodiments, the presence or absence of gases, such as trapped air, may define one or more system states.

System states may still further comprise qualitative and/or quantitative descriptions that are related to the presence, absence and/or other characteristics of components of the aspiration thrombectomy system. In particular embodiments, as will be discussed further, the disclosed methodology may be used to detect when an aspiration catheter is not attached to the thrombectomy system. In particular embodiments, system states may also comprise qualitative and/or quantitative descriptions that are related to specific aspects of operational importance for the aspiration thrombectomy system. In particular embodiments, as will be discussed further, the disclosed methodology may be used to detect when a clot has been engaged by the distal end of the aspiration catheter. In particular embodiments, such a determination may be used to further automatically initiate modulated aspiration. In particular embodiments, such a determination may be used to further automatically initiate a maceration cycle.

The contents of the system comprising the connection tubing and/or aspiration catheter may include blood, including healthy blood, and clots and other occlusive material found in vasculature, such as thrombus, embolus, plaque, occlusive material, and/or vessel blockage material. Additionally, the contents of the system may include other fluids and materials used for preparing and for operating the aspiration thrombectomy system. In particular embodiments, a saline fluid may be used for flushing and/or priming the aspiration thrombectomy. In particular embodiments, gas bubbles, such as air bubbles, may be trapped in the connection tubing and/or aspiration catheter, and may be part of the contents of this system. In particular embodiments, the generation of pressure level changes via operating the vacuum valve may be considered the creation of a pressure wave in the system comprising the contents of the connection tubing and/or aspiration catheter.

Although this disclosure describes using particular sensors and/or valves for detecting particular system states in a particular manner, this disclosure contemplates providing any suitable sensors, actuators or methodologies for detecting system states or taking further action in any suitable manner.

Particular embodiments of a dynamic system state detection methodology may separately or additionally use pressure sources and/or valves other than the vacuum source and vacuum valve described above. In particular embodiments, as has been previously disclosed, a pressure source may be connected in fluid communication with the connection tubing via a controllable pressure valve, wherein a reference pressure level of a pressure source may vary from vacuum (i.e., a very low absolute pressure) to absolute pressures that are significantly higher than ambient pressures or systolic blood pressures. As an example and not by way of limitation, in particular embodiments, a saline supply system may be used as such a pressure source. These separate or additional pressure sources and/or pressure valves may be used in different combinations for generation of pressure level changes, and/or for initiating action as a consequence of determining specific system states.

Particular embodiments of this dynamic system state detection methodology may separately or additionally use sensors other than the distal pressure sensor described above. In particular embodiments, as has been discussed previously, a vacuum pressure sensor monitoring the level of vacuum at the canister may be used. In particular embodiments, a saline pressure sensor monitoring the pressure level of the saline fluid may be used. Furthermore, sensors used in particular embodiments of this methodology may not be limited to pressure sensors. In particular embodiments, data may be sourced from a variety of sensors, including, for instance, sensors for detecting pressures, sonic energy, ultrasonic energy, and flow rates.

In particular embodiments, one or more system scores may be determined for determining system states, wherein each system score, independently or in combination with other system scores, may indicate a likelihood of specific system states in the aspiration catheter or the connection tubing. In this respect, system scores may function as metrics for quantifying the corresponding likelihood of specific system states.

System scores may be directly or indirectly derived from sensor data, such as the detected pressure profiles discussed above. In particular embodiments, system score determination may be based on automatically identifying specific features from the detected pressure profiles, extracting pressure parameters based on values and trends derived from those specific features, and calculating one or more system scores based on the pressure parameters of those features. In particular embodiments, system scores may be determined as summations of specific parameter indicators, such as pressure parameters. By way of example and not limitation, one or more pressure parameters indicating a system state of open flow may return a system score of 1, or 2, or 3, for instance, depending upon the specific pressure parameter(s) and specific threshold values used in the system combination, application, and/or embodiment, which may be directly summed for computing quantitative values of one or more system scores, such as an open flow score. In particular embodiments, determining system scores may involve further processing. In particular embodiments, determining system scores based on pressure parameters may further comprise appropriate weighting of the parameters, and/or use of correction factors. By way of example and not limitation, weighting of pressure parameters may be determined empirically. Maximum and minimum values, thresholds, and other characteristics relevant to system scores may be determined and/or adjusted based on specific system combinations and/or applications. For instance, specific thresholds of system scores may be varied based on specific combinations of catheter and aspiration systems. Several examples and particular embodiments with specific features involving detected pressure profiles and corresponding system scores will be further discussed. It should be appreciated that derivation of system scores from sensor data may vary across embodiments, and may be tailored for the specific configuration and application.

In particular embodiments, system scores may be determined based on machine learning. In particular embodiments, intermediate quantities used toward determining system scores may be determined based on machine learning. By way of example and not limitation, intermediate quantities of interest may include thresholds and/or weighting factors. In particular embodiments, training data sets may be assembled from detected pressure profile data taken over a broad range of scenarios, incorporating statistical variations, and corresponding to system states of interest. Trained machine learning models may be then used to make predictions of system state for novel situations. In particular embodiments, machine learning algorithms may employ semi-supervised and/or unsupervised learning. The algorithms may employ clustering, dimensionality reduction, and/or reinforcement learning to further improve prediction accuracy. Additionally, an algorithm that uses a combination of the above algorithmic flow analysis techniques may be employed in particular embodiments.

It is noted that particular sensor parameters and profiles, such as pressure profiles, choices of parameters, thresholds, and other criteria, and/or all other quantities such as valve states that are illustrated in this document are exemplary, and not limiting. For example, illustrations in FIGS. 23-70, which are further discussed below, are provided as examples, and not by way of limitation.

Figure 23:
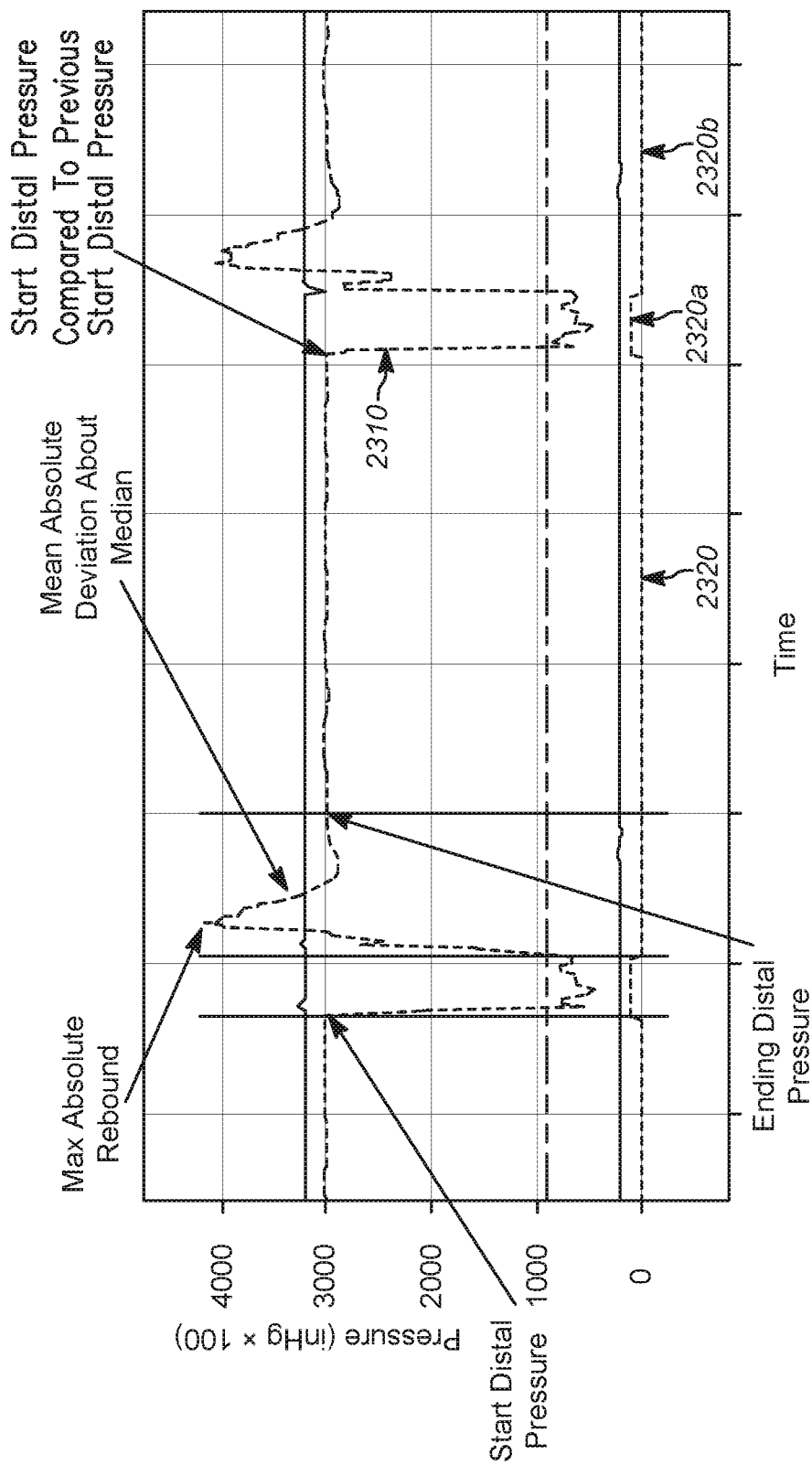
FIG. 23 illustrates a particular embodiment of a distal pressure profile detected over time, illustrating some pressure parameters.

FIG. 23 illustrates a distal pressure profile detected over time, for a particular embodiment, illustrating some pressure parameters. A distal pressure profile 2310 is based on the time-varying pressure detected by the distal pressure sensor. A corresponding vacuum valve state profile 2320 indicates the time-varying state of the vacuum valve, where an open state of the vacuum valve is indicated as a relatively elevated steady level on the y-axis, such as in 2320a, and the closed state of the vacuum valve as a relatively lowered steady level, such as in 2320b. As with the vacuum valve states described above, the open or closed states of vacuum valves or other valves in other figures and illustrations herein may also be indicated by the relative levels of the respective valve profiles on the y-axis.

As a result, in particular embodiments, it may be possible to observe in a detected pressure profile (such as illustrated in FIG. 23) the response of the system to pressure level changes generated by cycling (i.e., the rapid opening and closing) of the vacuum valve. FIG. 23 further illustrates some specific exemplary features of a detected pressure profile, previously mentioned as pressure parameters.

For instance, in particular embodiments illustrated by FIG. 23 and corresponding to a generally unrestricted or open flow scenario, when the vacuum valve is first opened, the distal pressure may experience a large decrease in pressure as the contents of the connection tubing and aspiration catheter become exposed to the very low absolute pressure levels of the vacuum source, and accelerate toward the lower pressure.

For example, a value of the distal pressure corresponding to its starting value prior to the sudden distal pressure decrease may be identified as a Start (or Starting) Distal Pressure, as illustrated. For instance, in particular embodiments, a Starting Distal Pressure may be indicative of a patient's blood pressure, as well as of time history of the system state. Further, in particular embodiments, rates of change of Starting Distal Pressure may be correlated with blood viscosity, and/or the presence of clots in the catheter. Following the subsequent closing of the vacuum valve, the contents of the connection tubing and aspiration catheter may experience an abrupt deceleration, and an eventual return to the new pressure equilibrium in the system disengaged from the vacuum source.

One or more peak pressure levels may be pressure parameters of interest for determining system scores, and/or system states. In particular embodiments, the recorded maximum value of the large overshoot of distal pressure corresponding to the vacuum valve closing in this scenario may be identified as the Maximum Absolute Rebound pressure, as illustrated in FIG. 23 by way of example, and not by way of limitation. Maximum Absolute Rebound Pressure may also be correlated with blood viscosity.

In particular embodiments, one or more pressure levels and/or time intervals corresponding to restoration of pressure level equilibria following a pressure change generation event, such as vacuum valve cycling, may be pressure parameters of interest for determining system scores, and/or system states. For instance, a time window may be established based on pressure and/or time metrics that corresponds to the cessation of effects of a pressure disturbance related to an opening and closing sequence of the vacuum valve. In particular embodiments, the value of the distal pressure at such a time instant may be identified as an Ending Distal Pressure, as illustrated. For instance, in particular embodiments, an Ending Distal Pressure may correspond to the distal pressure value at a predetermined time interval, such as 80 ms, after vacuum valve closing, or may also be based on a time interval determined based on other parameters.

It should be appreciated that specific definitions and thresholds for sensor parameters may vary across embodiments, based on the requirements of specific configurations and applications. The following disclosed pressure parameters and related features are intended to be exemplary, and not limiting.

In particular embodiments, measures of pressure variance may be further extracted as pressure parameters. For instance, the pressure variance between the time instants marking Start and Ending Distal Pressure may be considered for such extraction. In particular embodiments, a Mean Absolute Deviation ("MAD") of pressure about the Median ("Med") pressure, as illustrated, may be identified as a measure of pressure variation between closing of the vacuum valve and the time instant of Ending Distal Pressure. Mean Absolute Deviation of pressure about the Median pressure ("MAD/med") may also be correlated with blood viscosity.

In particular embodiments, differential pressure levels may be pressure parameters of interest for determining system scores, and/or system states. In particular embodiments, for two consecutive vacuum valve cycling sequences, the difference of the second Start Distal Pressure relative to the first Start Distal Pressure may be identified as a differential pressure level of interest, as illustrated in FIG. 23. Such a Differential Start Distal Pressure may be stable across viscosity.

As previously discussed, system scores may be determined based on detected pressure parameters. In particular embodiments, an Open Score may be determined based on detected pressure parameters. As an example and not by way of limitation, the value of the Open Score may vary between 0 and 7, and may indicate the likelihood of at least an open flow state. Similarly, in particular embodiments, an Occlusion Score may be determined based on detected pressure parameters. As another example and not by way of limitation, the value of the Occlusion Score may vary between 0 and 7, and may indicate the likelihood of at least an occluded flow state. Furthermore, in particular embodiments, various combinations of an Open Score and an Occlusion Score may indicate the likelihood of one or more additional system states of interest, for instance, a partially occluded flow state.

In particular embodiments, thresholds may be established for determining system states based on system scores. As some examples and not by way of limitation, in particular embodiments, the system may be determined to be in an occluded state if the Occlusion Score equals or exceeds 3 (out of a maximum possible score of 7). In particular embodiments, the system may be determined to be in an open flow state if the Open Score equals or exceeds 3 (again, out of a maximum possible score of 7). In particular embodiments, if the Open Score and Occluded Score are both less than 3, the system may be determined to be in a partially occluded state. Such a partially occluded state may, in particular embodiments, suggest the presence of a clot or thrombus that is pliable or deformable enough to be extracted by continuous aspiration, and not necessarily require pulsed or modulated aspiration.

Although this disclosure describes establishing specific thresholds for determining system states based on particular system scores in a particular manner, this disclosure contemplates providing any suitable thresholds for determining system states based on any system scores in any suitable manner.

FIGS. 24-31 illustrate particular embodiments of distal pressure profiles for a range of system state scores. In these examples of particular embodiments, specific parts of the respective detected profiles are highlighted, and an Occlusion Score and an Open Score determined based on detected pressure parameters are indicated corresponding to the highlighted parts of each detected pressure profile. These illustrations are exemplary, and not provided by way of limitation.

Figure 24:
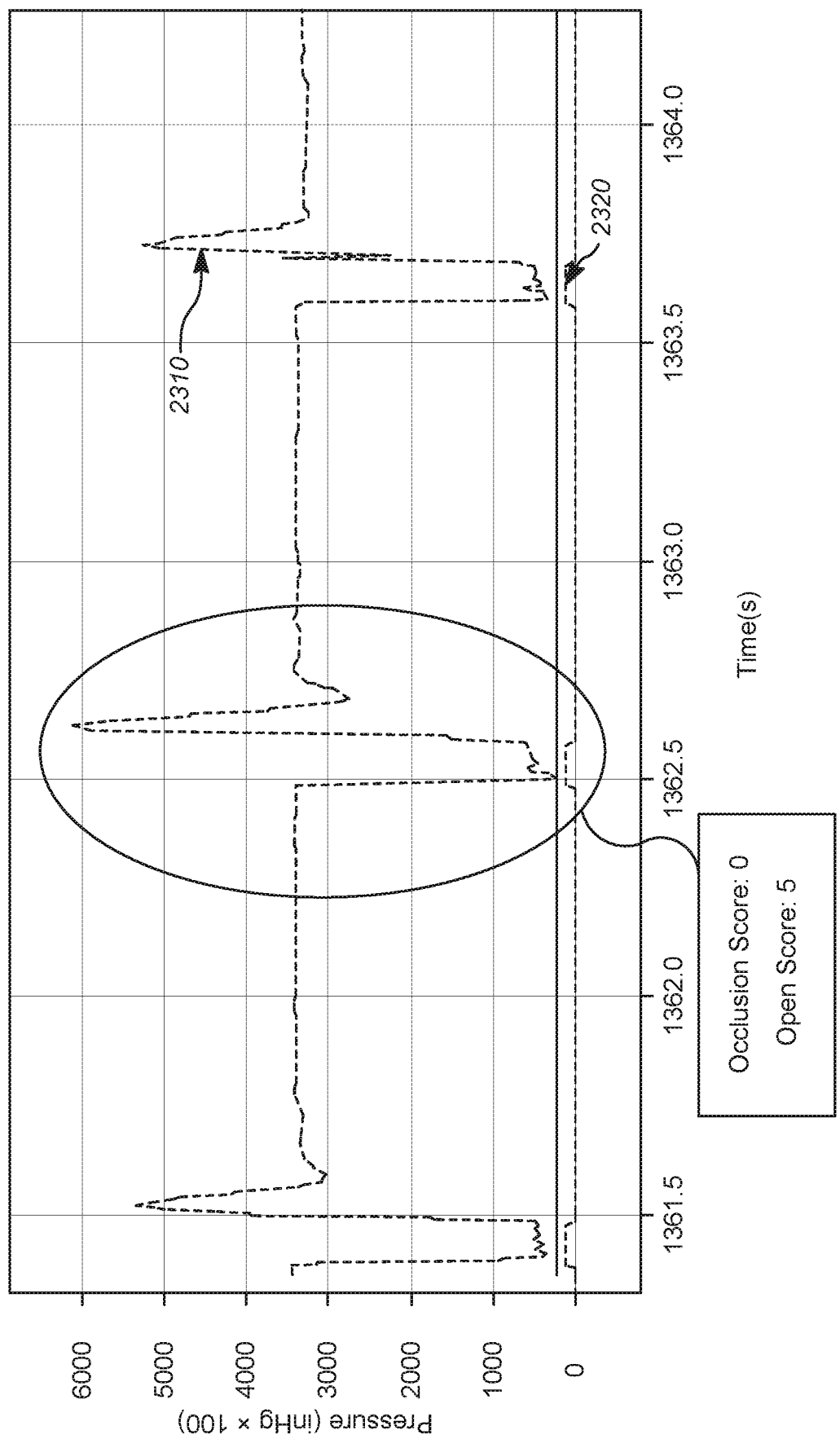
FIGS. 24-31 illustrate particular embodiments of distal pressure profiles for a range of system state scores.

For instance, FIG. 24 illustrates a detected distal pressure profile in a generally open or unrestricted flow scenario, for a particular embodiment. The detected profile of the particular embodiment illustrates relatively rapid pressure changes 2310 responsive to vacuum valve state changes 2320. The highlighted zone illustrates a relatively large overshoot or maximum rebound pressure, as well as a high variance of detected pressure immediately flowing vacuum valve closure. Based on at least these pressure parameters, the Occlusion Score in this example is determined to be 0, whereas the Open Score is determined to be 5.

Figure 25:
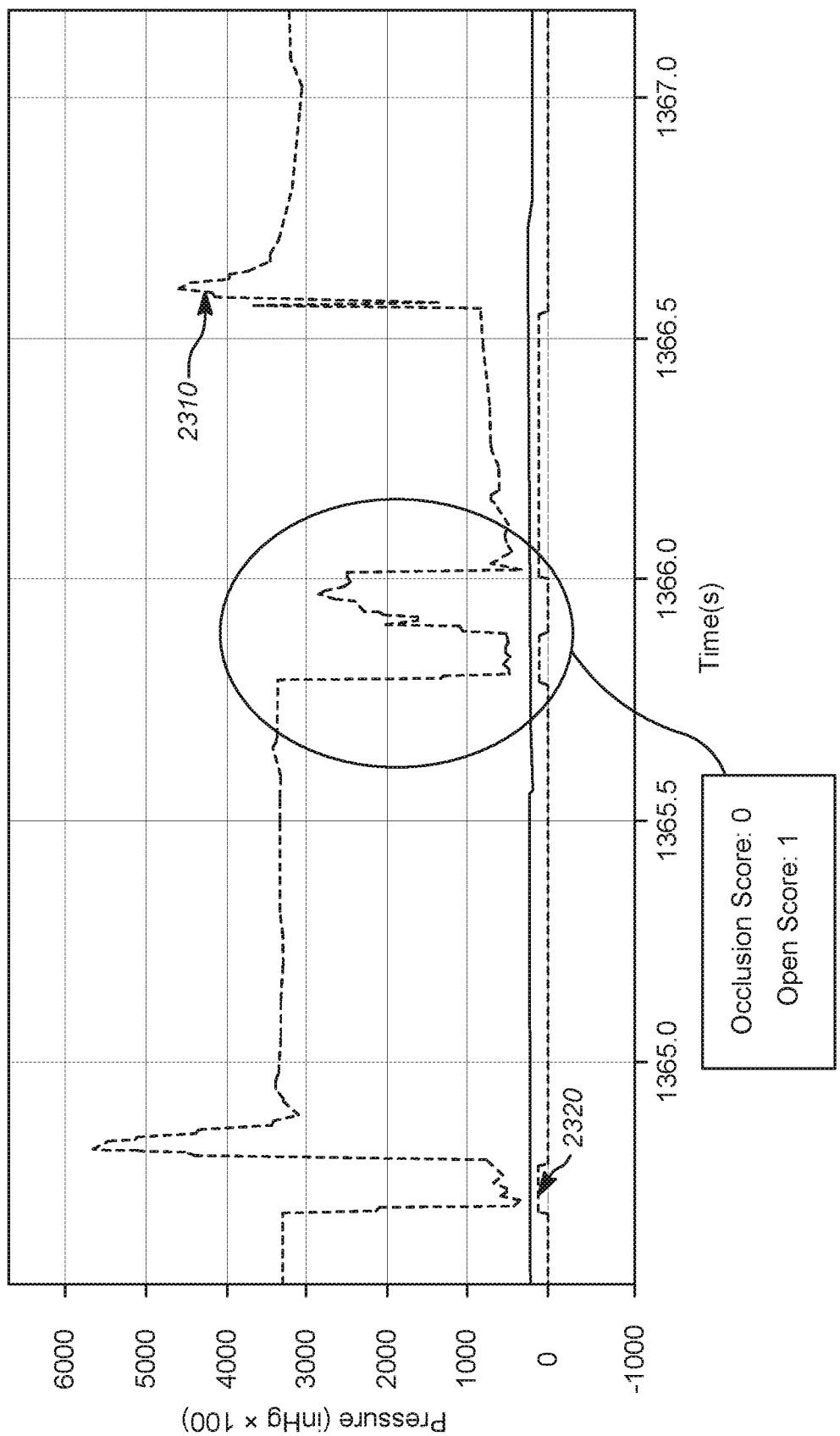
Figure 26:
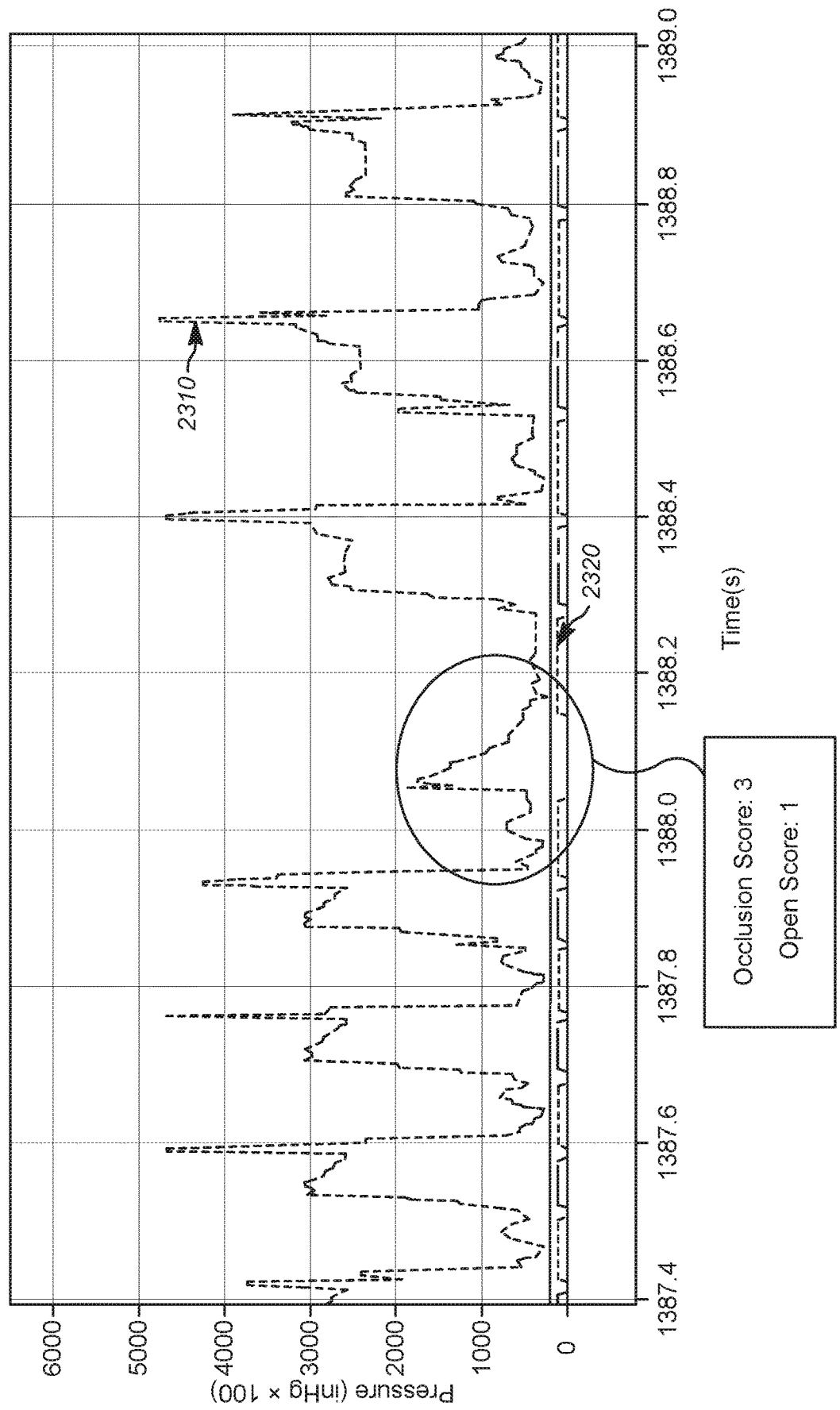

As another example, FIG. 25 illustrates the detected distal pressure profile in a partially occluded flow scenario, for a particular embodiment. The profile illustrates relatively damped rebound, with the detected pressure level not being restored to the levels of its starting distal pressure. Based on at least these pressure parameters, the Occlusion Score in this example is determined to be 0, whereas the Open Score is determined to be 1. FIG. 26 illustrates a particular embodiment where the Occlusion Score is determined to be 3, and the Open Score is determined to be 1.

Figure 27:
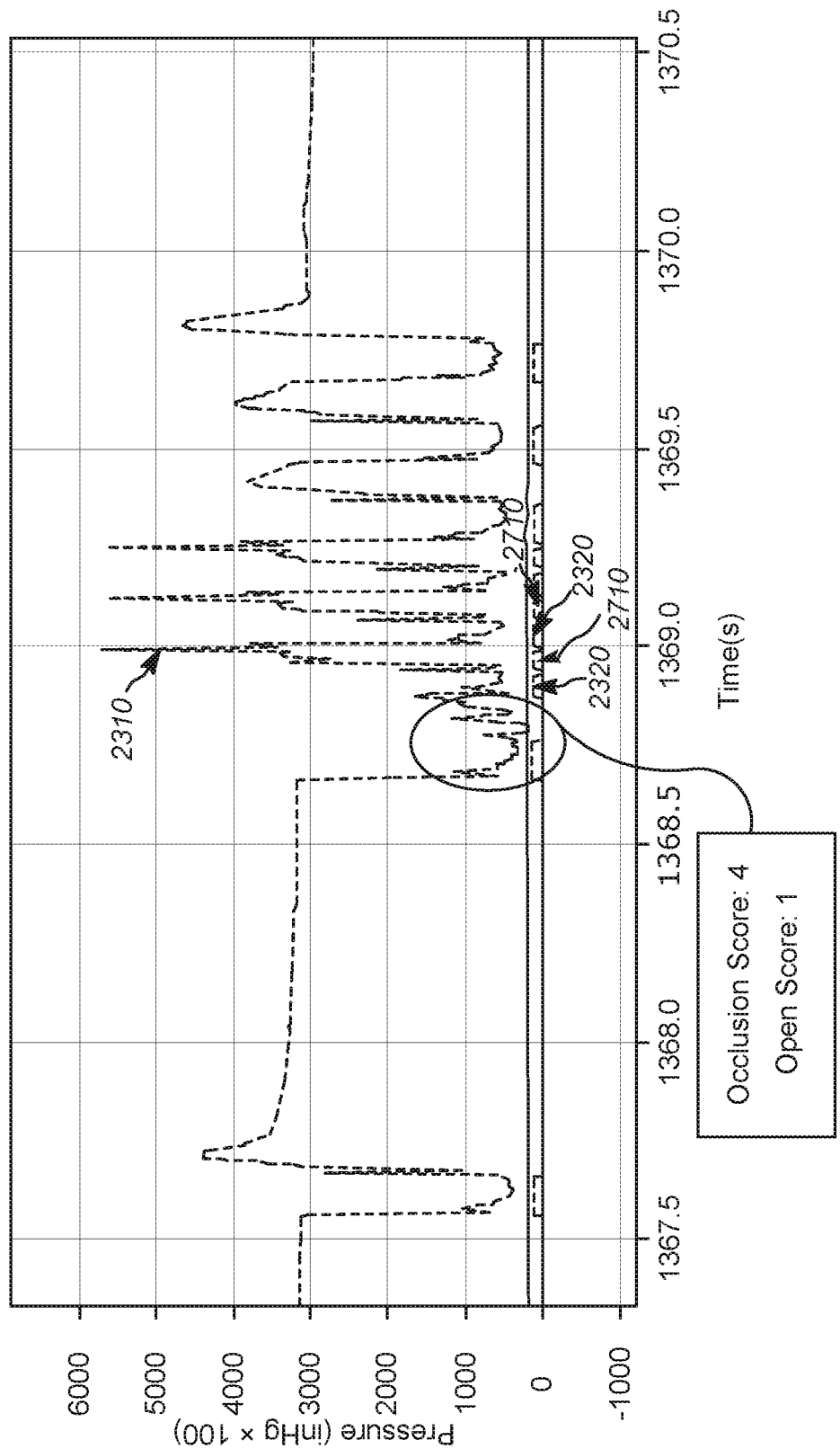

FIG. 27 illustrates an example where the Occlusion Score is determined to be 4 and the Open Score is determined to be 1, for a particular embodiment. In this example, the system may be initially determined to be in an open flow state based on the pressure profile detected in response to the first vacuum valve cycling, starting soon after the 1367.5 s time marker. Based on a determination of open flow, the system may be operated in intermittent aspiration, i.e., the vacuum valve may be held closed for a time interval to prevent aspiration of healthy blood. During this intervening time interval, in some embodiments, the catheter may be repositioned for engagement with a clot. The vacuum valve profile indicates that it was cycled again soon after the 1368.5 s time marker. Based on the corresponding detected pressure profile, the system may be determined to be in an at least partially occluded flow state, which is reflected in the system scores determined in this example. In some embodiments, as illustrated here, the system may trigger modulated or pulsed aspiration in response to this situation. Modulated aspiration may be observed in this particular embodiment as alternately cycling vacuum valve profile (2320) and pressure valve profile (2710), each indicating the time-varying state of the respective valve. In some embodiments, a saline fluid at an elevated pressure may function as a pressure source via a pressure valve. By the end of the sequence, as the distal profile illustrates, the occlusion may be aspirated, and the exemplary pressure profile illustrates indications of the system being in an open flow state again.

Figure 28:
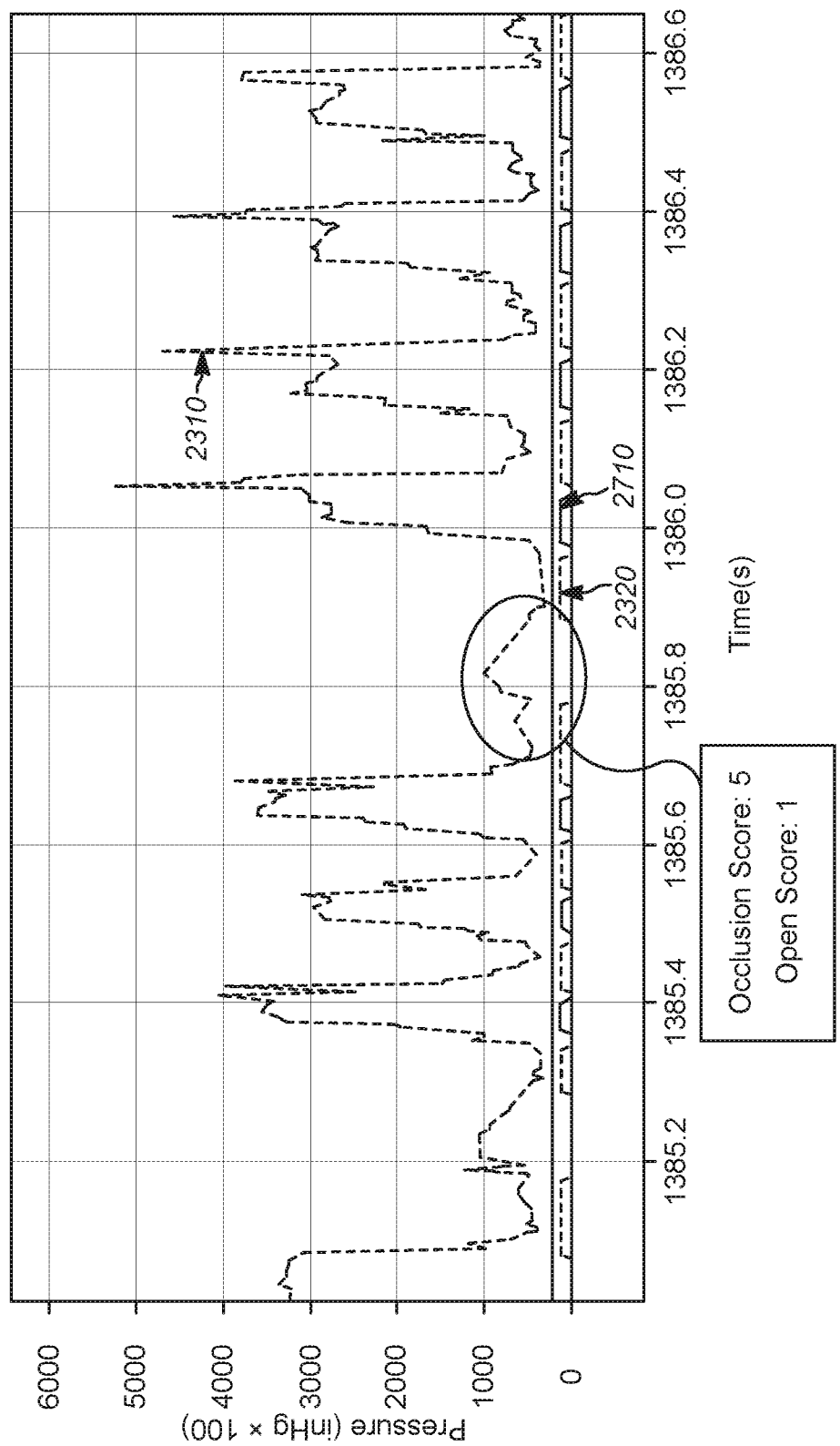
Figure 29:
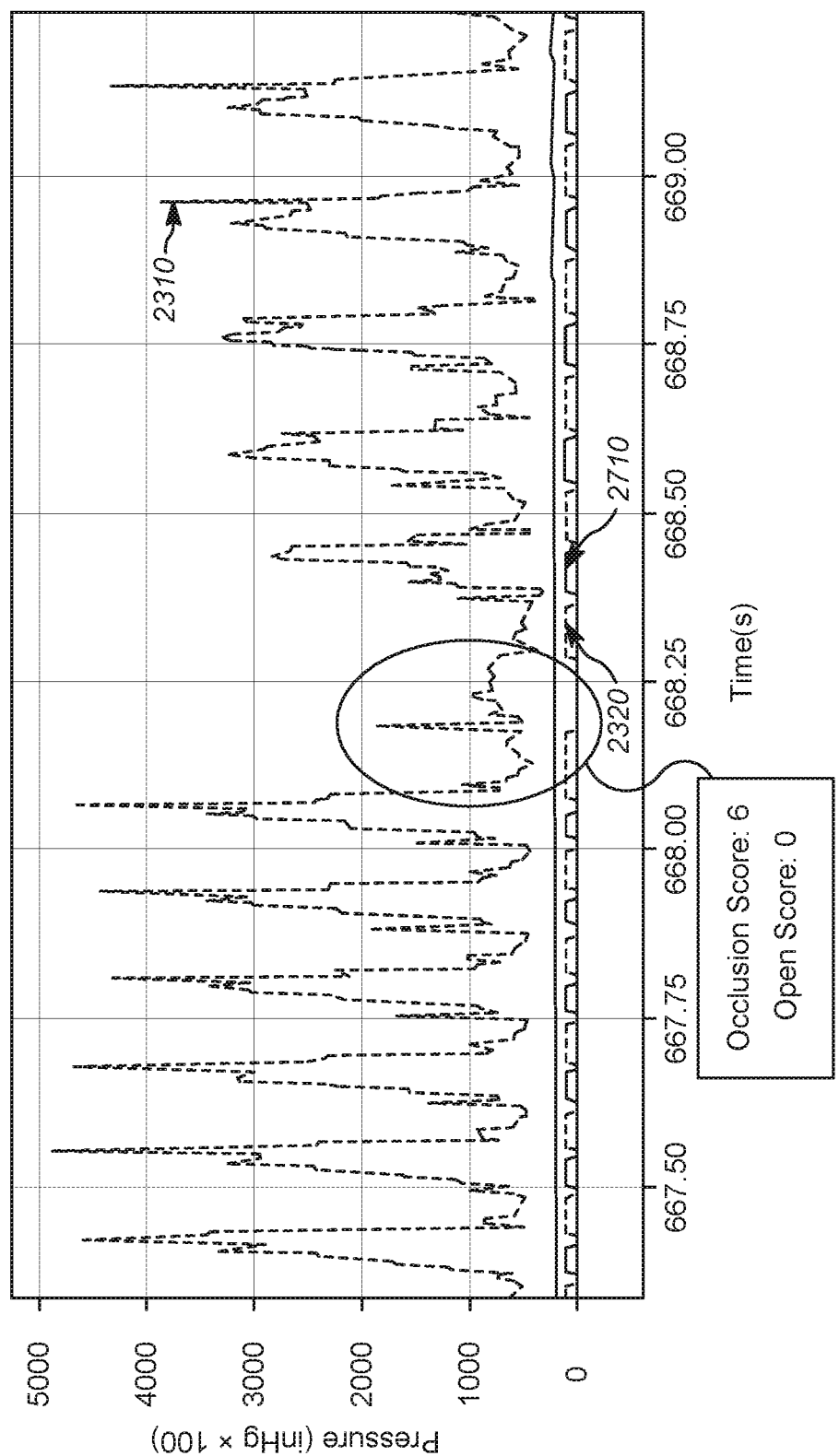
Figure 30:
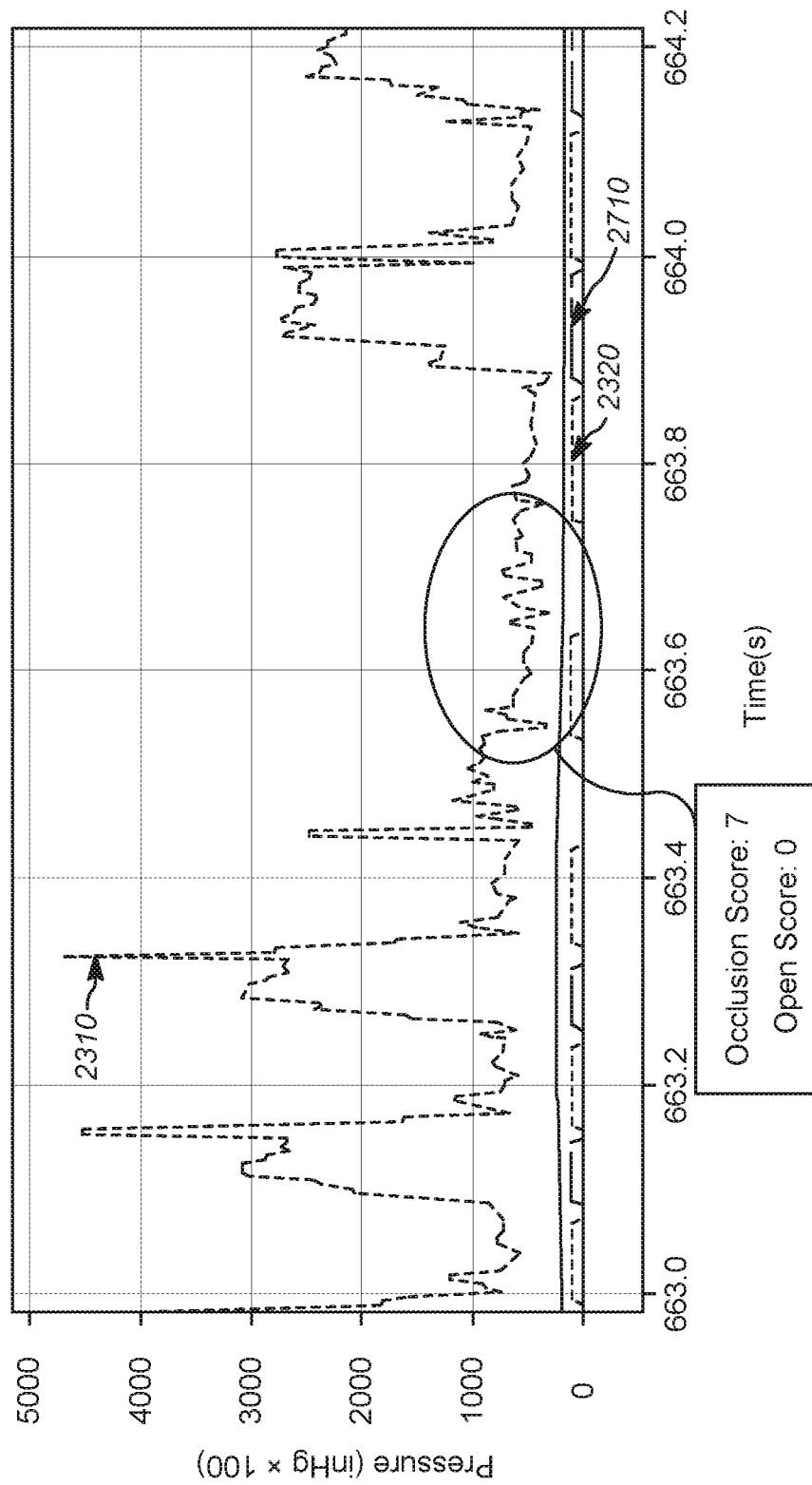
Figure 31:
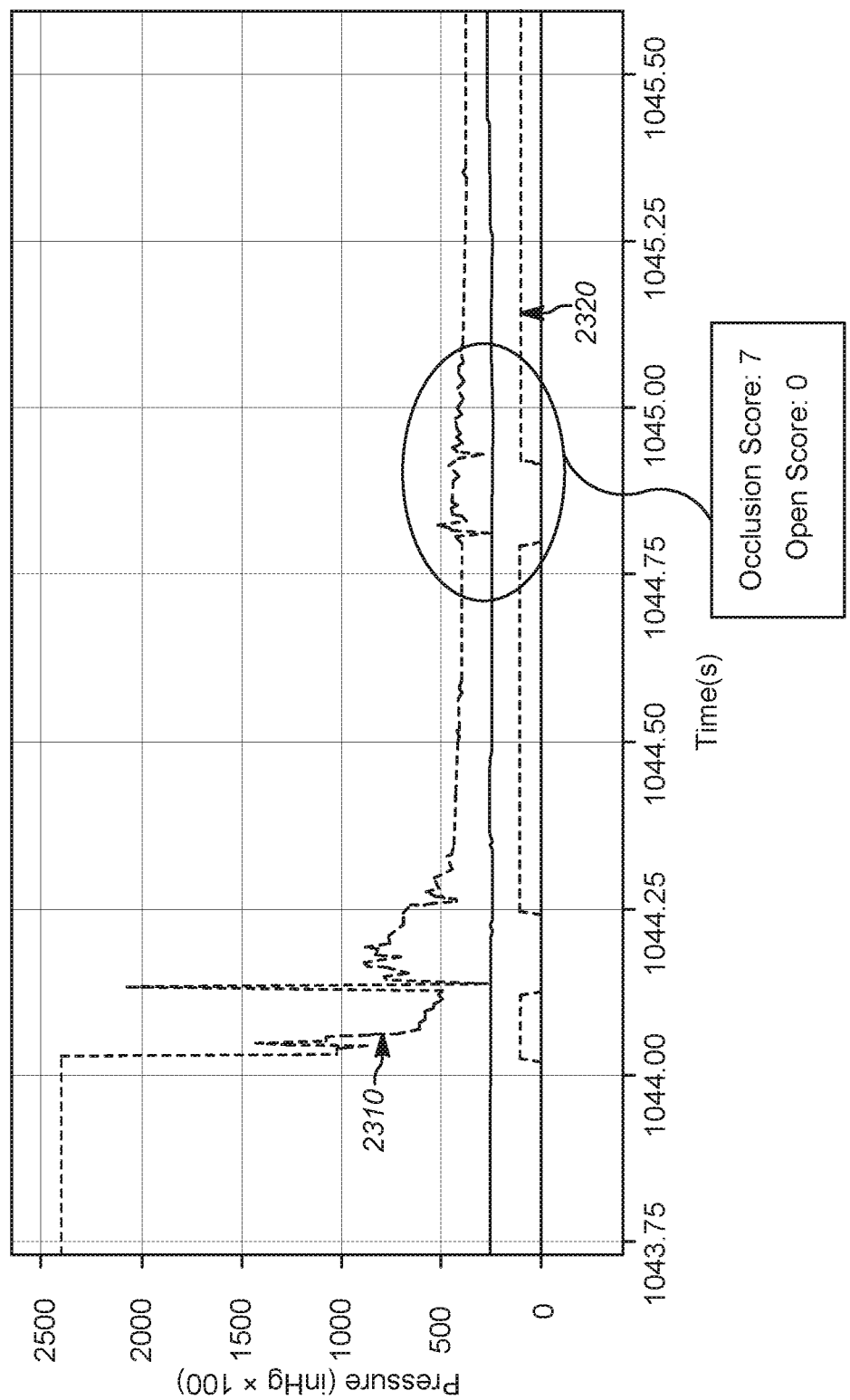
Figure 32:
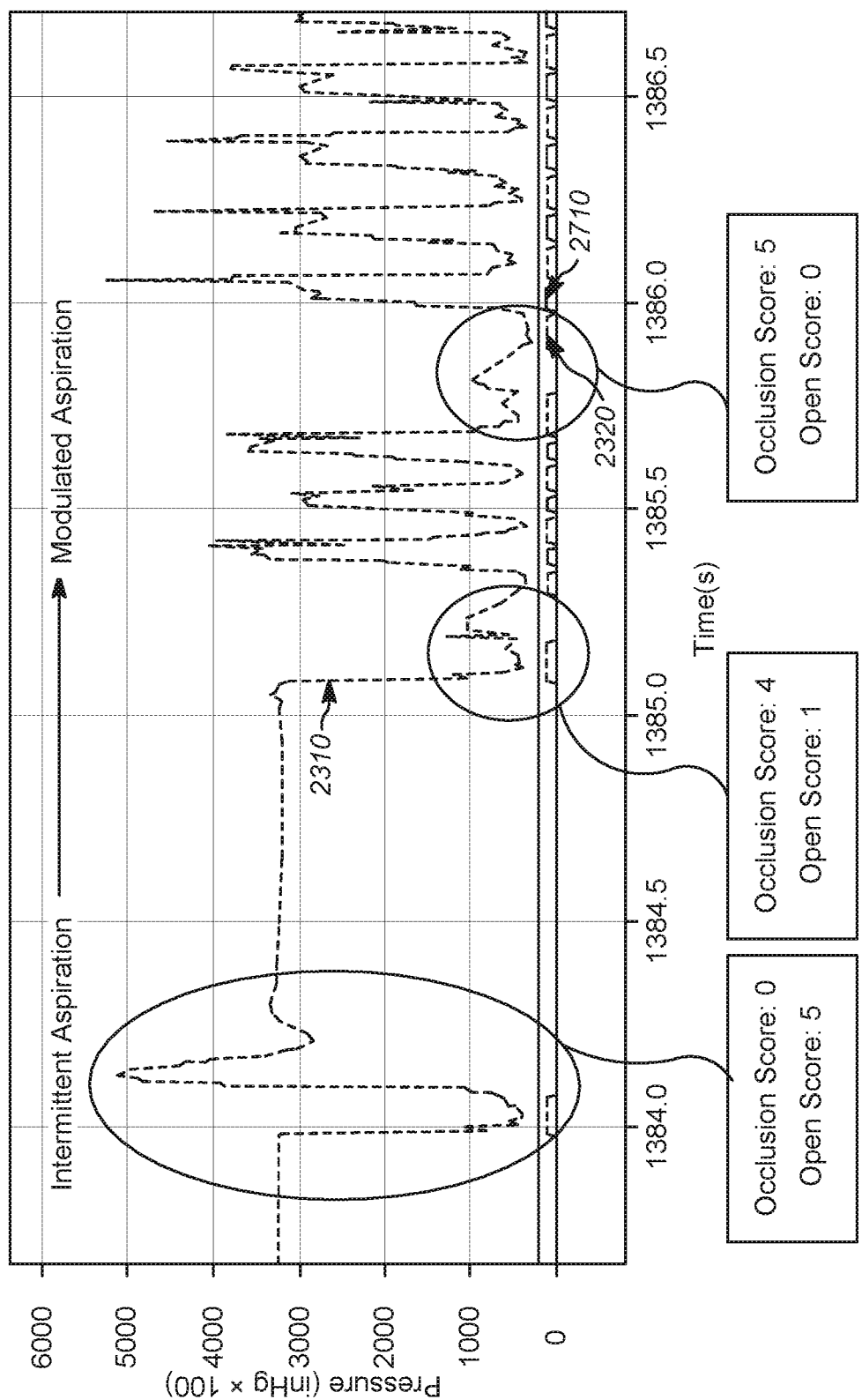
FIG. 32 illustrates a particular embodiment of evolution of distal pressure profile and corresponding system state scores.

FIGS. 28-31 illustrates examples of progressively more pronounced markers that may indicate occlusion in particular embodiments, with correspondingly larger Occlusion Scores, and/or lower (or zero) Open Scores determined by the controller. FIG. 28 illustrates an example with an Occlusion Score of 5, and an Open Score of 1. FIG. 29 illustrates an example with an Occlusion Score of 6, and an Open Score of 0. FIG. 30 illustrates an example with an Occlusion Score of 7, and an Open Score of 0. FIG. 31 illustrates a different example with an Occlusion Score of 7, and an Open Score of 0. FIG. 32 illustrates an open flow and corresponding intermittent aspiration evolving into an occluded or partially occluded flow in a particular embodiment, which may require modulated or pulsed aspiration. These illustrations are exemplary, and not provided by way of limitation.

In particular embodiments, particular combinations of Occlusion Score, Open Score, and/or other system scores may be used to trigger a maceration cycle for applying mechanical forces on occlusive material. Such mechanical action may be applied to sufficiently modify the form and/or consistency of a clot or other occlusive material to enable more effective aspiration.

In particular embodiments, an escalation feature may be used wherein an Escalate Count of consecutive determinations of identical system state is maintained by the controller, and specific action may be taken if the count exceeds a threshold. In particular embodiments, the count may be reset in the iteration following the threshold crossing iteration. In particular embodiments, the action taken if the count exceeds a threshold may be generating a notification, such as a user notification. In particular embodiments, the action taken if the count exceeds a threshold may involve the operation of one or more valves by the controller. In particular embodiments, the parameters for modulated or pulsed aspiration may be adjusted based on a combination of the Occlusion Score and the Escalate Count.

Figure 33:
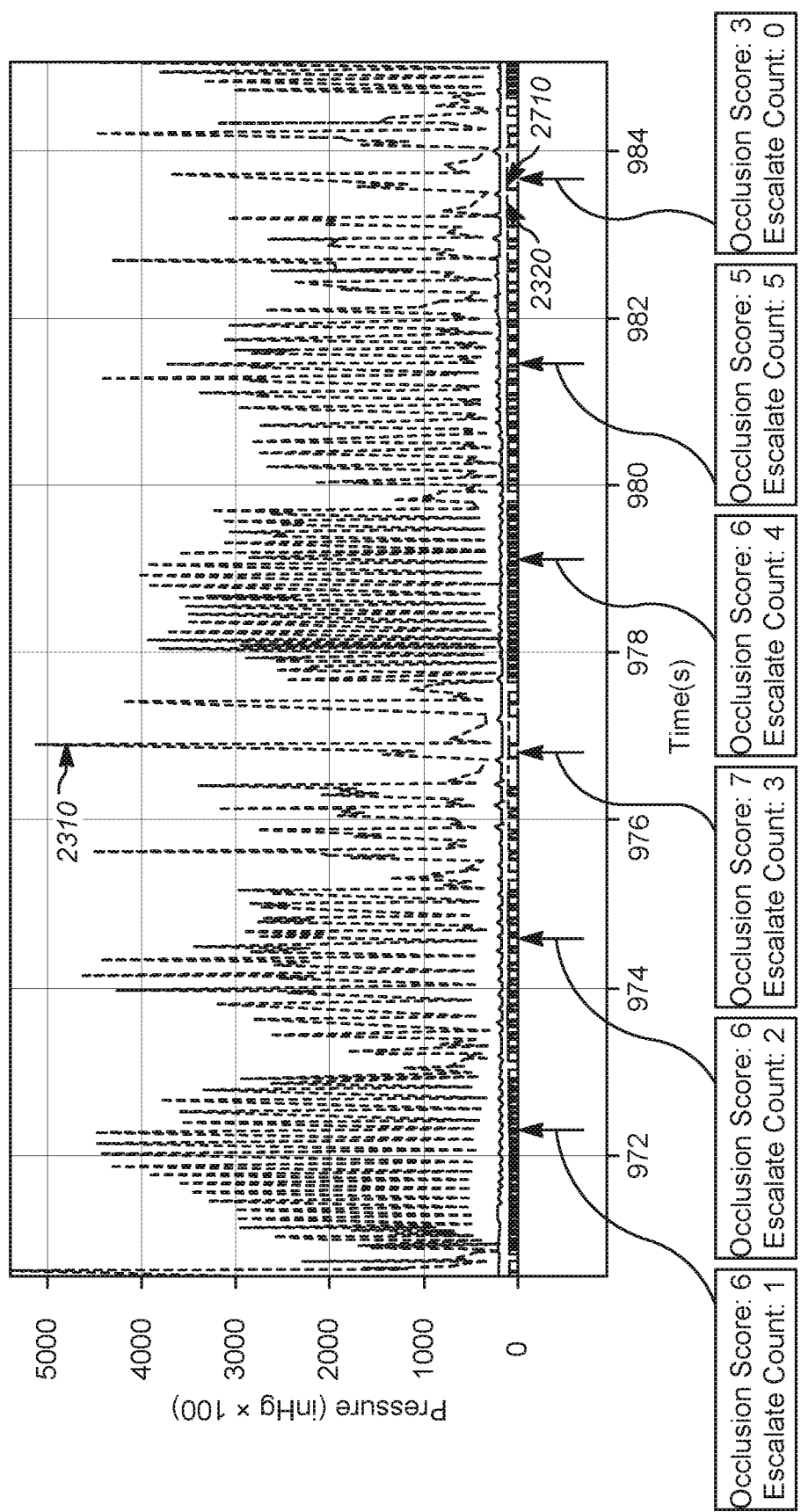
FIG. 33 illustrates a particular embodiment of consecutive system scores, and escalation.

FIG. 33 illustrates the progression of an escalation count scenario, in a particular embodiment. The Occlusion Score determined at the specific time instants indicated by the arrows is illustrated as an example, and not by way of limitation, fluctuating between 5 and 7 during the time interval spanning the first five such instants (arrows), but which may generally be indicating a persisting occluded flow state. Correspondingly, an Escalate Count is illustrated to be incrementing during each consecutive identical determination of occluded flow, until a threshold Escalate Count of 5 is reached, at which time, in particular embodiments, the parameters of the modulated aspiration may be modified based on the combination of the Occlusion Score and Escalate Count. At the next determination of system scores, as illustrated by the last arrow in FIG. 33, the Escalate Count may been reset to zero. In this example, the Occlusion Score is illustrated to have significantly decreased to 3.

In particular embodiments, the values of one or more system scores relative to thresholds may be used to initiate action based on operating one or more valves. Such action taken may additionally depend on prior or current system states and/or modes of aspiration by valve operation.

In particular embodiments of an aspiration thrombectomy system performing intermittent aspiration, an increase of an Occlusion Score beyond a threshold may trigger initiation of a modulated aspiration mode. In particular embodiments of an aspiration thrombectomy system performing intermittent aspiration, an increase of an Open Score beyond a threshold may trigger a mode involving continued intermittent aspiration. In particular embodiments of an aspiration thrombectomy system performing intermittent aspiration, if neither an Open Score nor an Occlusion score increase beyond a threshold, it may trigger initiation of continuous aspiration. In particular embodiments of an aspiration thrombectomy system performing modulated aspiration, a decrease of an Occlusion Score below a threshold may trigger a change of mode to intermittent aspiration.

Figure 34:
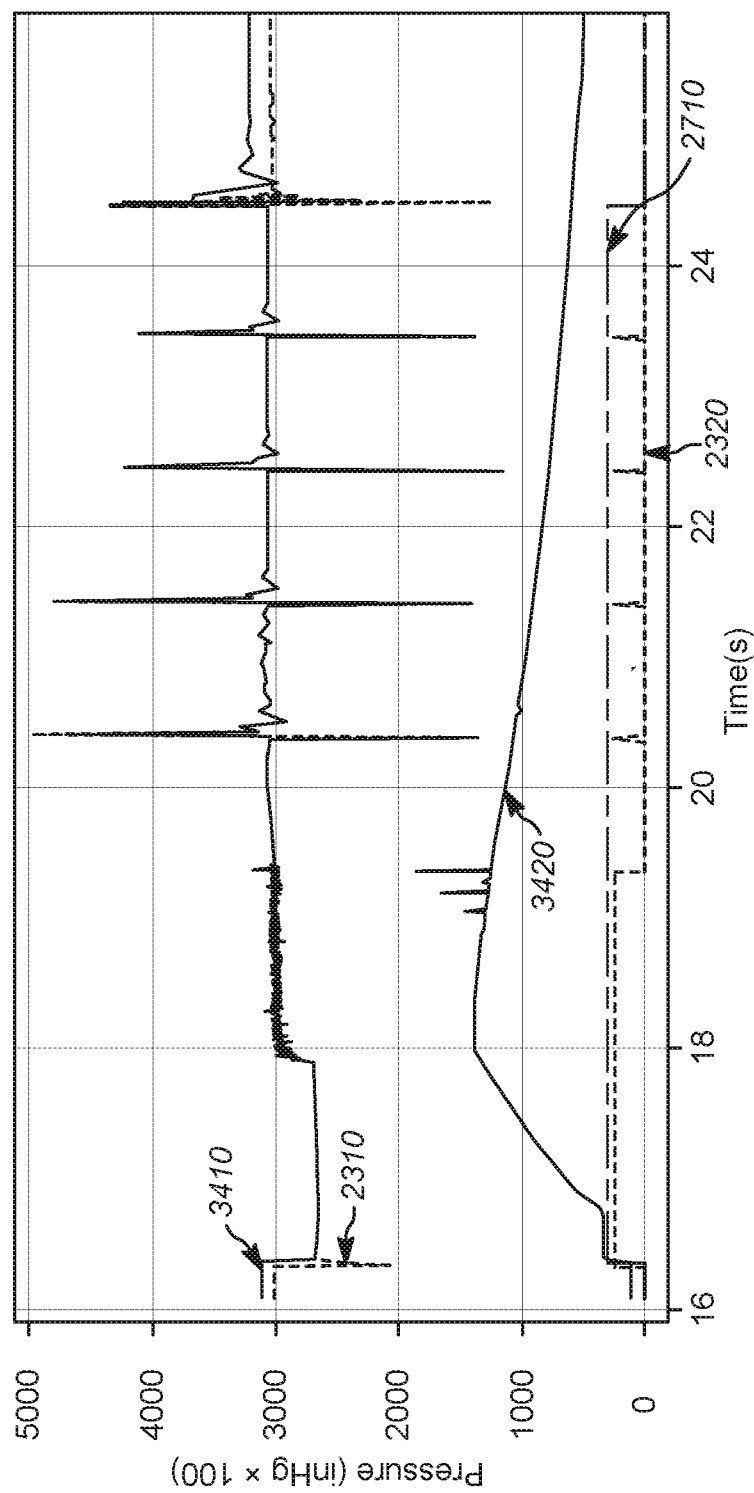
FIGS. 34-35 illustrate pressure profiles of particular embodiments during priming.
Figure 35:
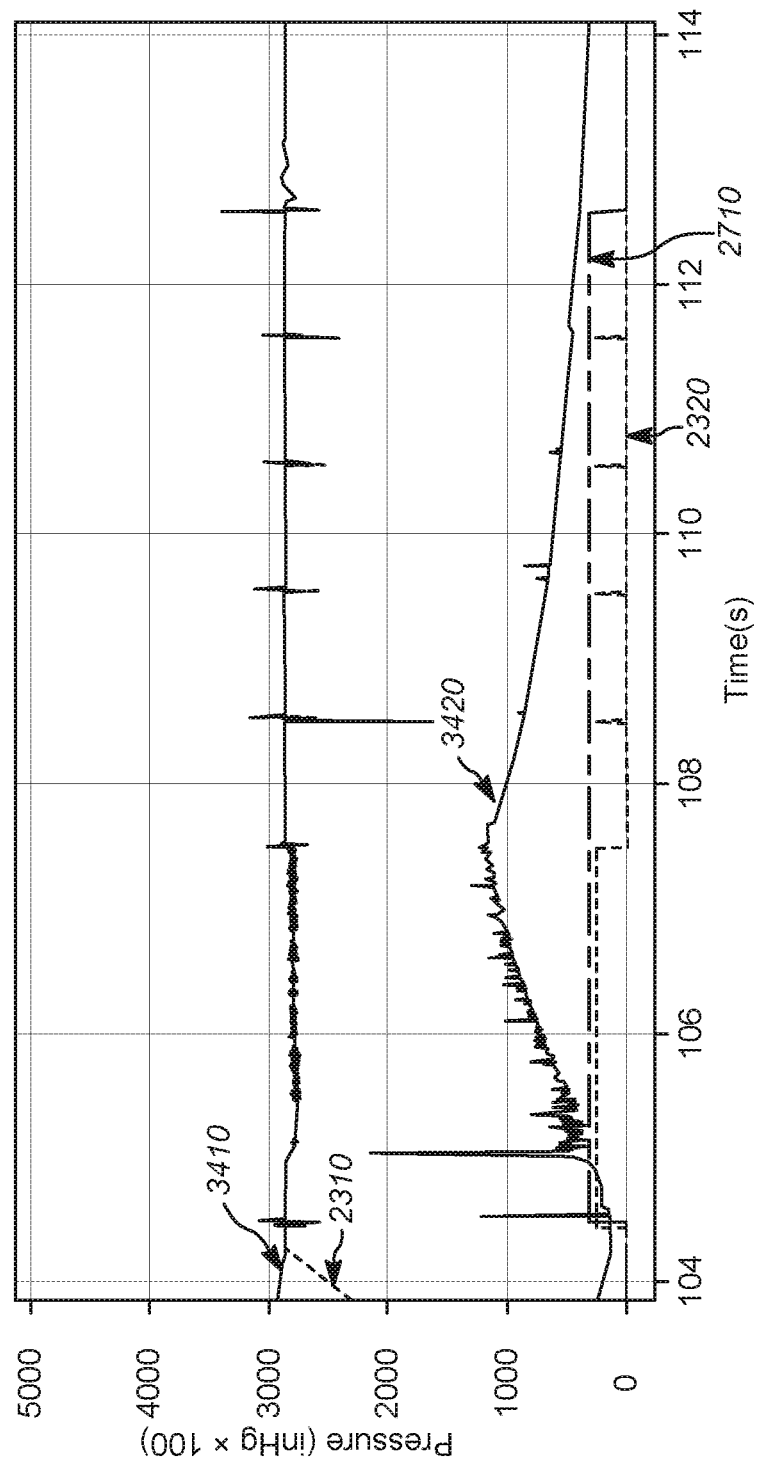

As previously discussed, additional system states may be determined based on detected sensor data correlated with generated pressure level changes. For instance, in particular embodiments, presence of saline and/or air in the system may be detected by such dynamic system state detection. FIGS. 34 and 35 illustrate examples of detecting a successful and an unsuccessful priming operation, respectively, in particular embodiments, by using detected pressure profiles correlated with generated changes in pressure by valve operation. These illustrations are exemplary, and not provided by way of limitation.

FIGS. 34 and 35 illustrate a distal pressure profile 2310, a saline pressure profile 3410 associated with a saline pressure source, and a vacuum pressure profile 3420 associated with a pressure in the vacuum canister, based on particular embodiments. An exemplary vacuum valve profile 2320 illustrates the time-varying open/close operational state of the vacuum valve. An exemplary pressure valve profile 2710, also called a vent valve profile, illustrates the time-varying open/close operational state of the pressure valve for the saline pressure source. Specific features and pressure parameters that may permit detection of saline and/or air will be further discussed.

Figure 36:
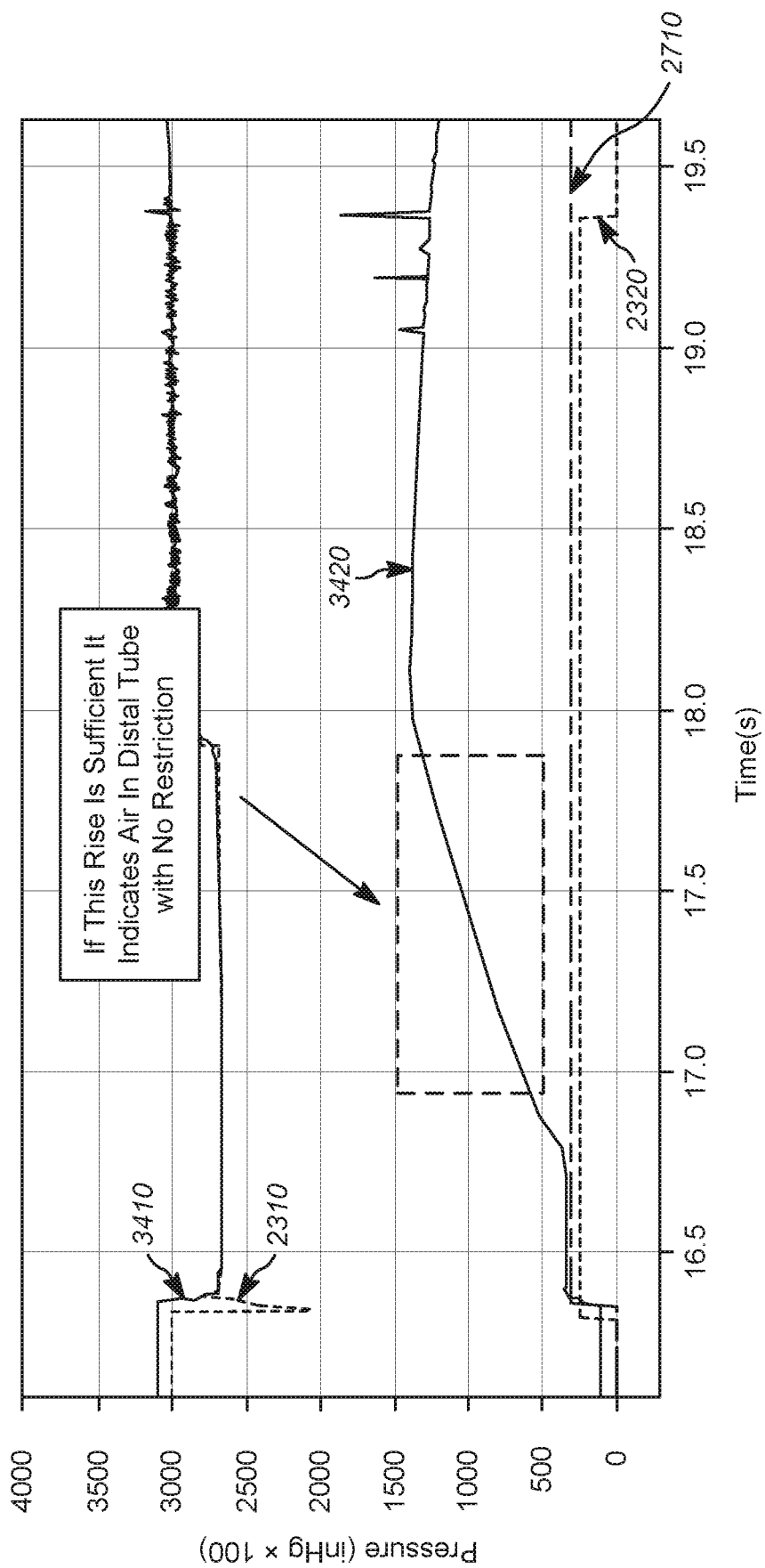
FIGS. 36-50 illustrate pressure profile features of particular embodiments for dynamic system state detection during priming.
Figure 37:
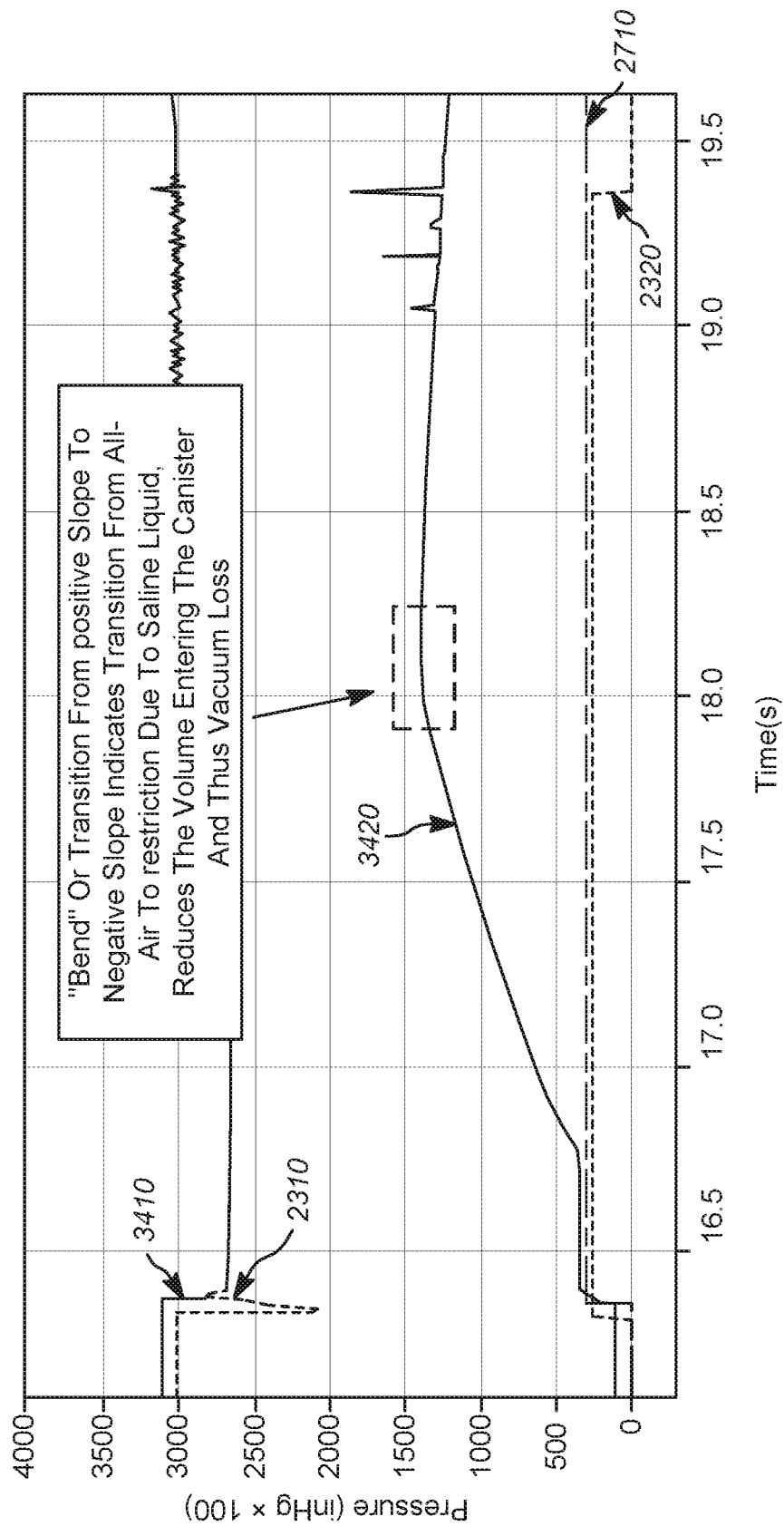
Figure 38:
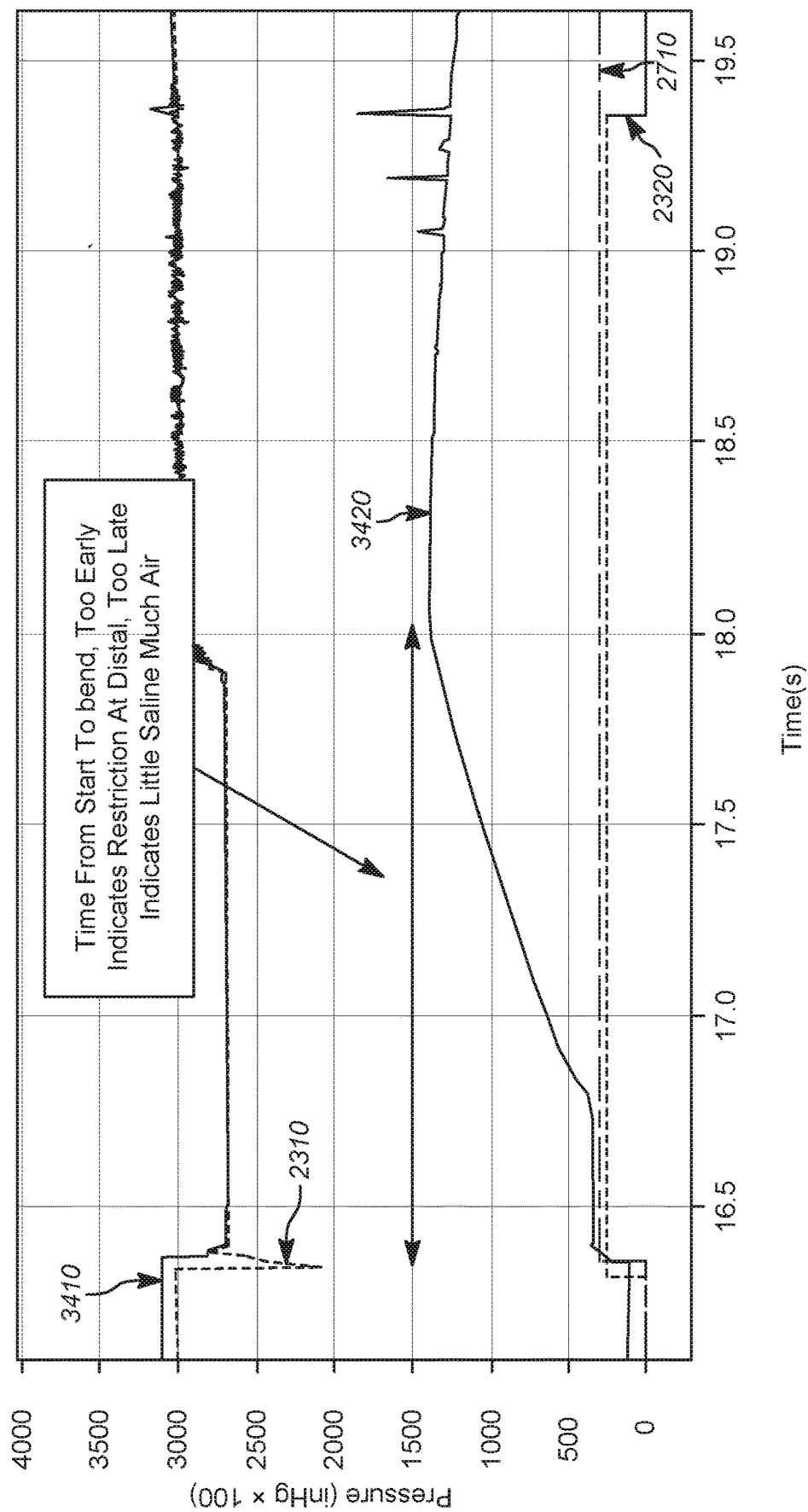

FIGS. 36-50 illustrate pressure profile features of particular embodiments for dynamic system state detection during priming. These illustrations are exemplary, and not provided by way of limitation. FIG. 36 illustrates pressure profiles at the beginning of a priming sequence in particular embodiments, upon opening both the vacuum valve and the saline pressure valve. It illustrates how the slope of a vacuum pressure profile may indicate air in the distal connection tubing, along with the absence of restrictions. FIG. 37 illustrates, still at the beginning of a priming sequence in particular embodiments, how the nature of a transition or change in slope of a vacuum pressure profile, such as a bend from positive to negative slope, may indicate a transition from an air-filled system to restrictions due to a saline liquid entering the vacuum canister. FIG. 38 illustrates how the time interval between the start of priming and identifying a bend, or change of slope, in the vacuum pressure profile, in particular embodiments, may be indicative of relative balance of air and/or saline, as well as restrictions at the distal connection tubing.

Figure 39:
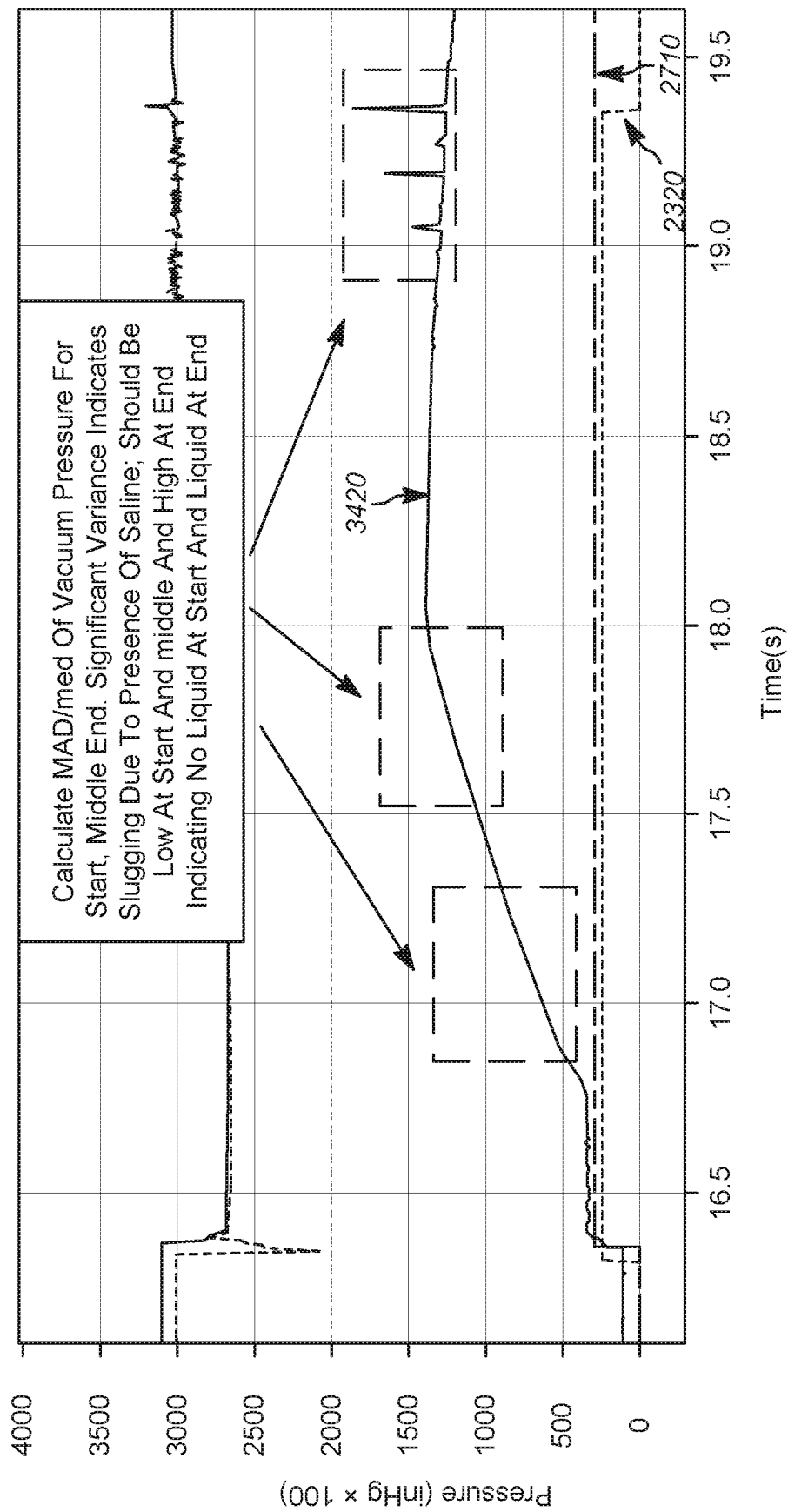
Figure 40:
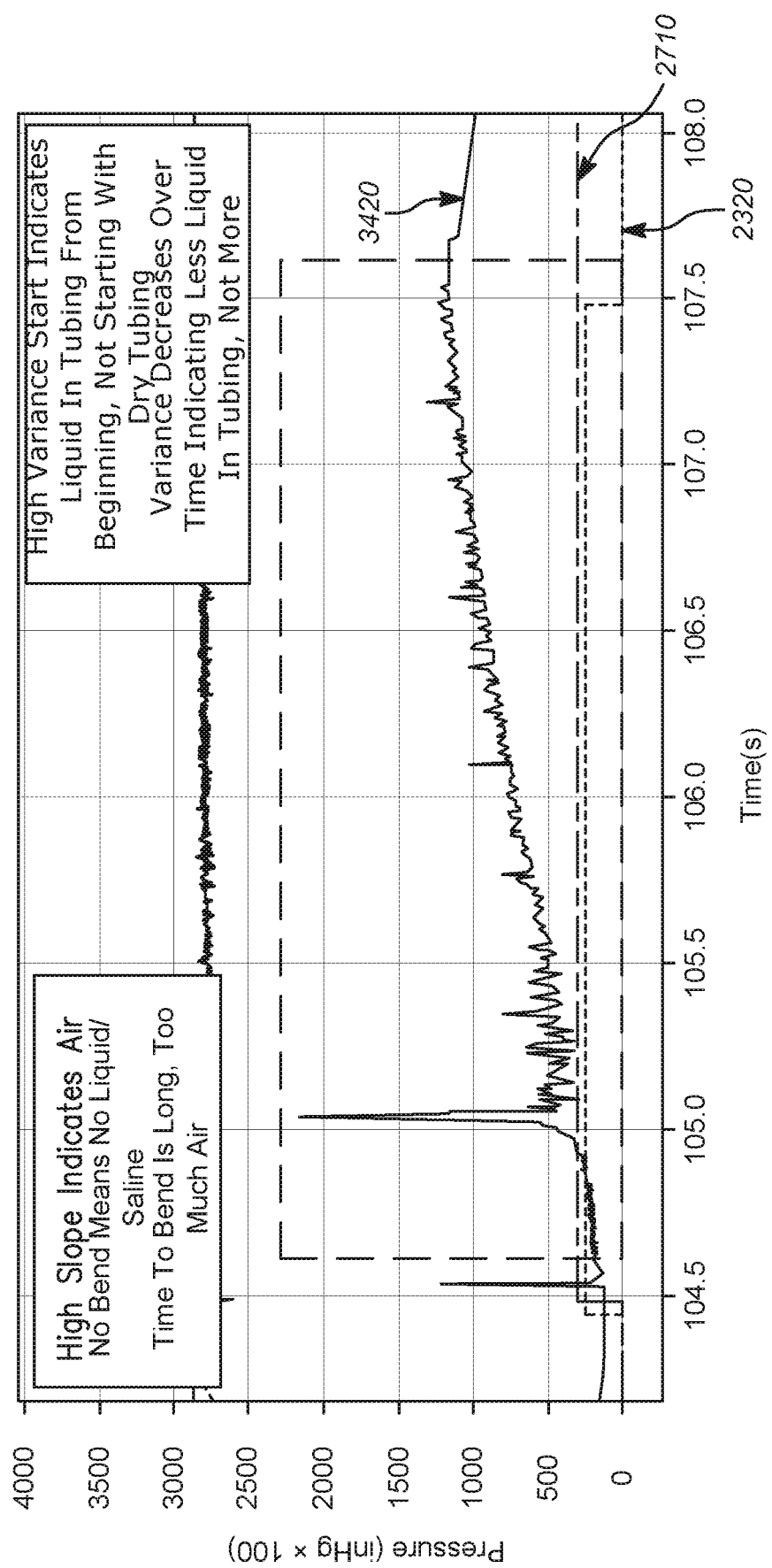

FIG. 39 illustrates how the Mean Absolute Deviation ("MAD") of Vacuum Pressure over the Median ("Med"), which may be denoted as "MAD/med," taken during time windows/intervals at the beginning, middle, and end of the priming operation, may be used to identify saline, and be used to detect successful priming, in particular embodiments. High levels of variance may indicate slugging due to liquid saline; such variance may increase through the evolution of a successful priming operation, indicating progressive replacement of air with liquid. In contrast, FIG. 40 illustrates features of a vacuum profile corresponding to an unsuccessful priming operation, in particular embodiments. During the early stages of priming, a high slope may indicate the presence of air, and the delay or absence of a notable and timely change of slope may be indicative of the absence of liquid saline. The excessive time taken for the slope to change may be indicative of too much air in the system. Furthermore, the levels of variance from the beginning may indicate starting with the presence of liquid in the tubing, rather than with dry tubing. A decrease in vacuum pressure variance over time may be indicative of less liquid in the tubing over time, rather than more.

Figure 41:
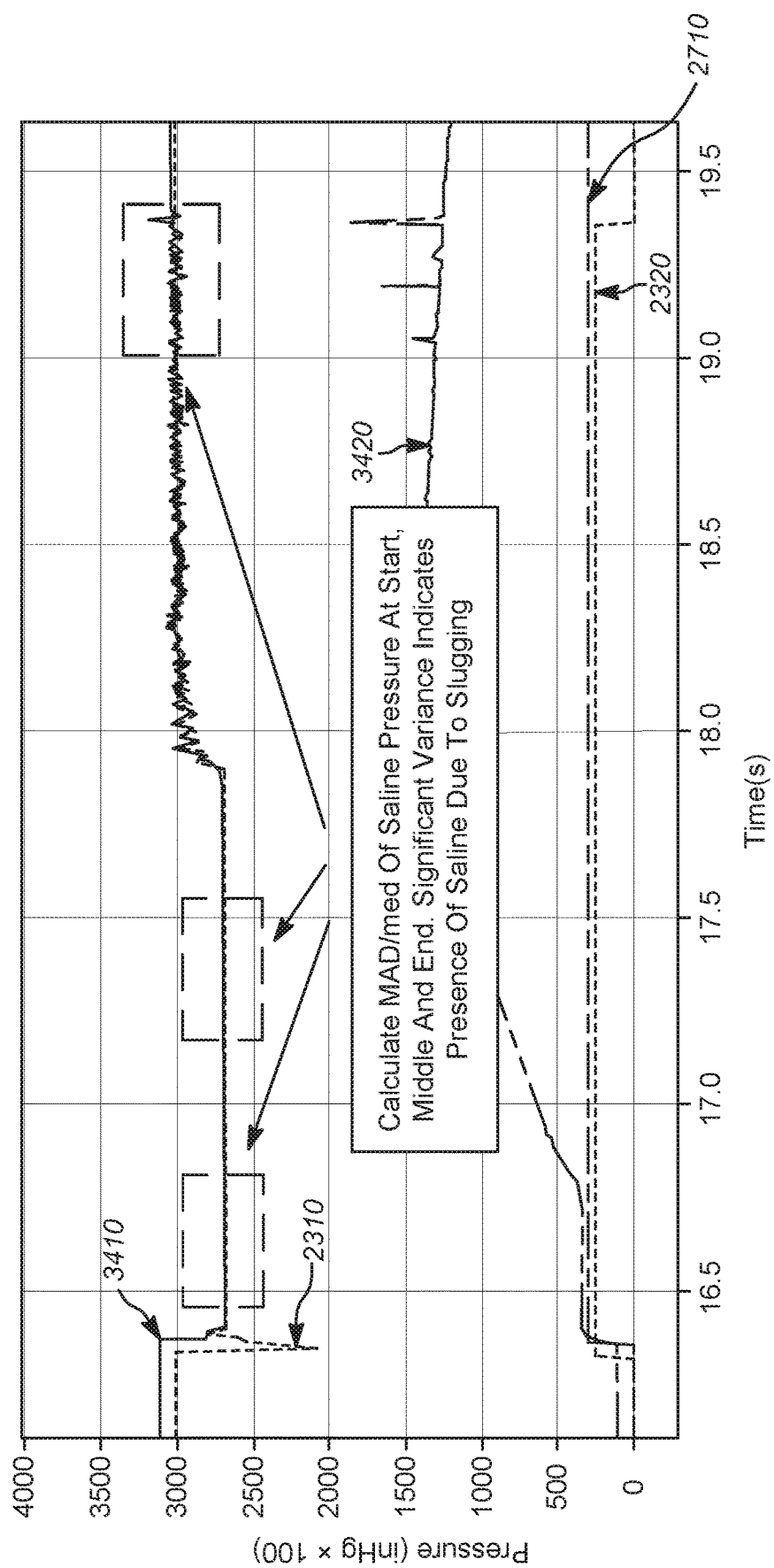
Figure 42:
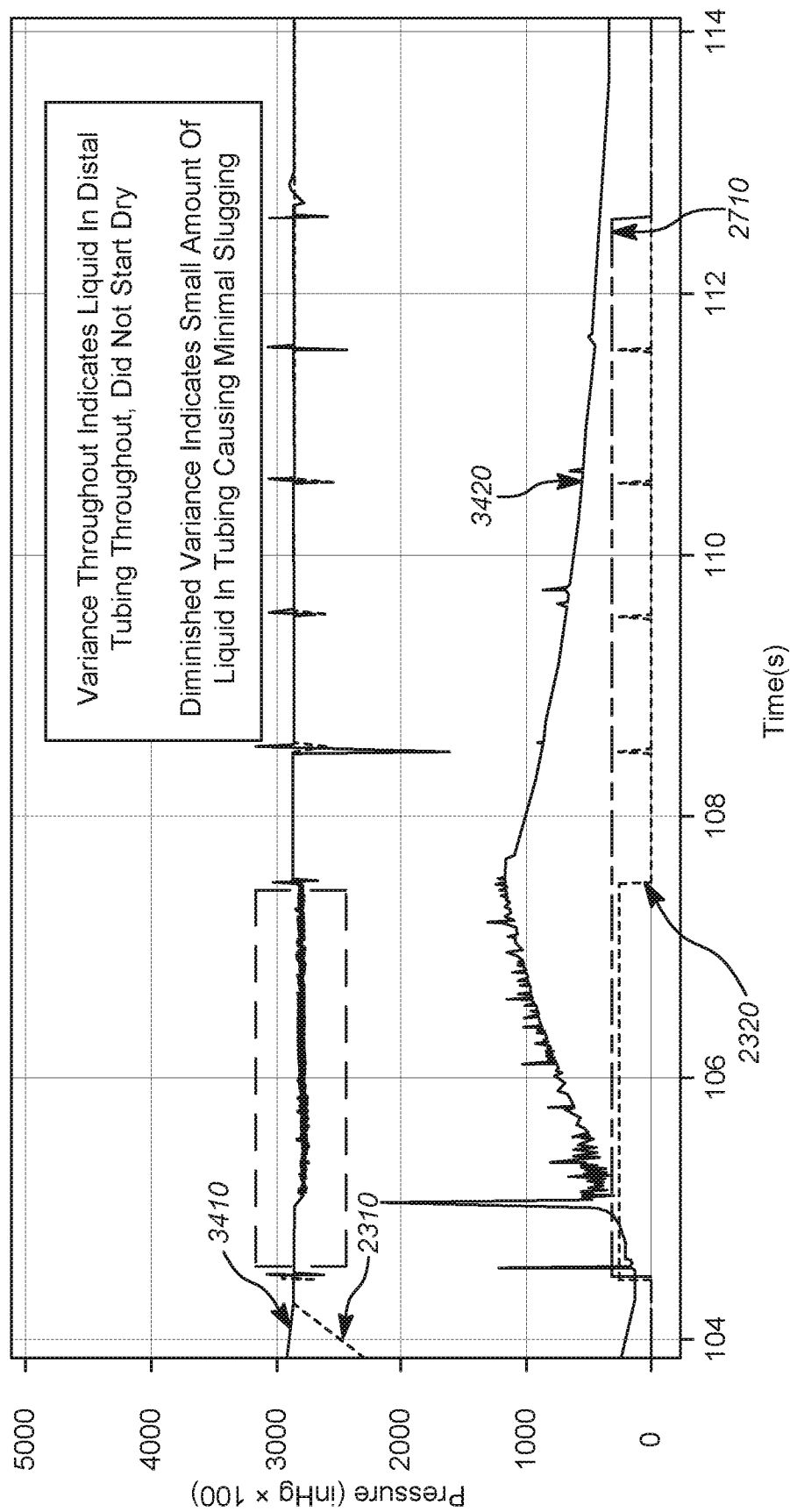

FIG. 41 illustrates the evolution of variance of saline pressure through the beginning, middle, and end of a successful priming operation, in particular embodiments. For instance, the Mean Absolute Deviation of Pressure over the Median, or MAD/med, of each pressure may be used as a metric of variance. Again, high levels of variance may be indicative of slugging due to the presence of saline. For the case of successful priming in this particular embodiment, the low variance at the beginning may be indicative of starting with a dry tube, with the increased and significant pressure variance by the end of the operation indicating potential presence of saline. In contrast, FIG. 42 illustrates significant pressure variance in saline pressure at the beginning of the priming sequence in particular embodiments, indicating that the tube may not have started dry. Diminished variance may indicate a small amount of liquid in the tubing causing minimal slugging.

Figure 43:
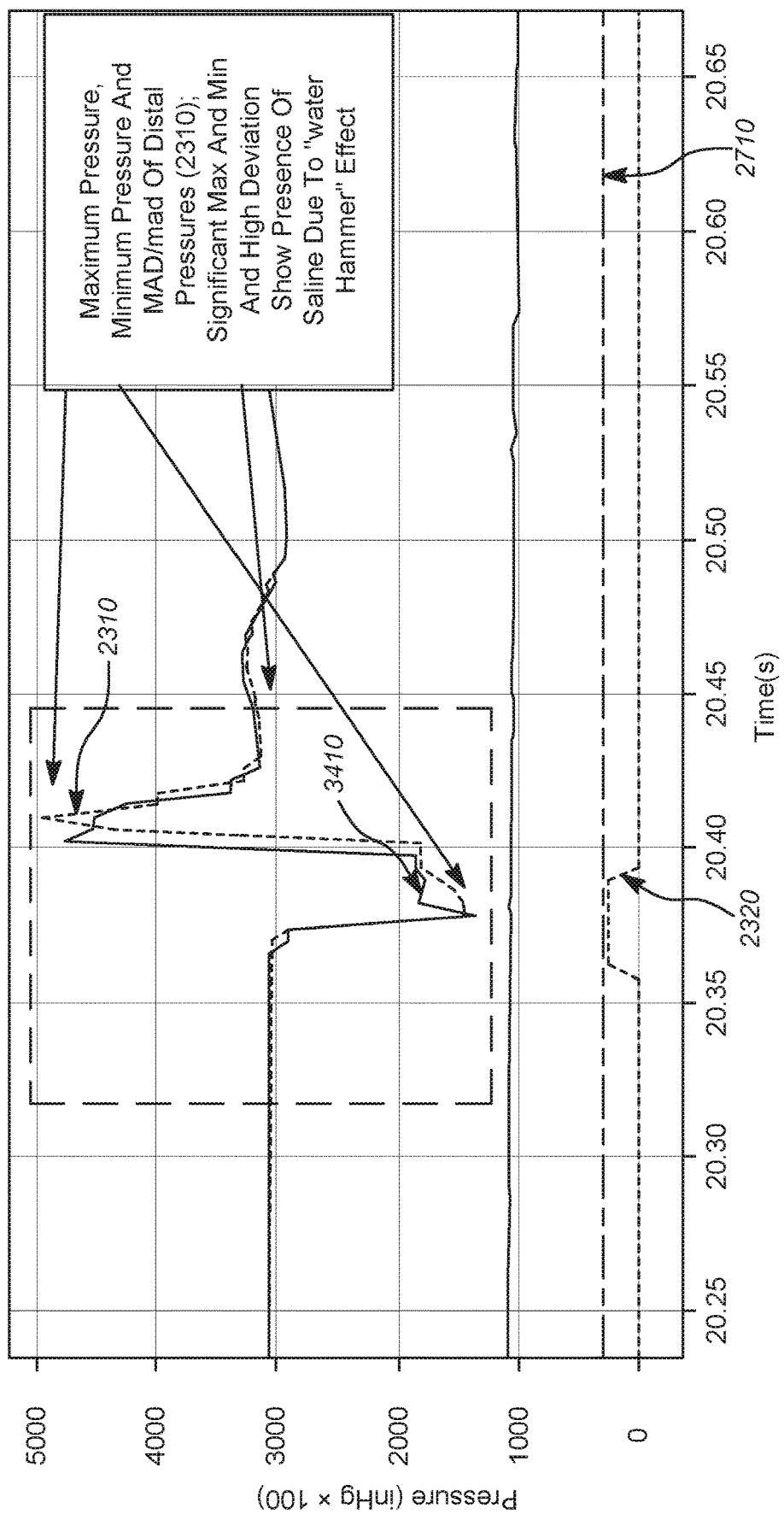
Figure 44:
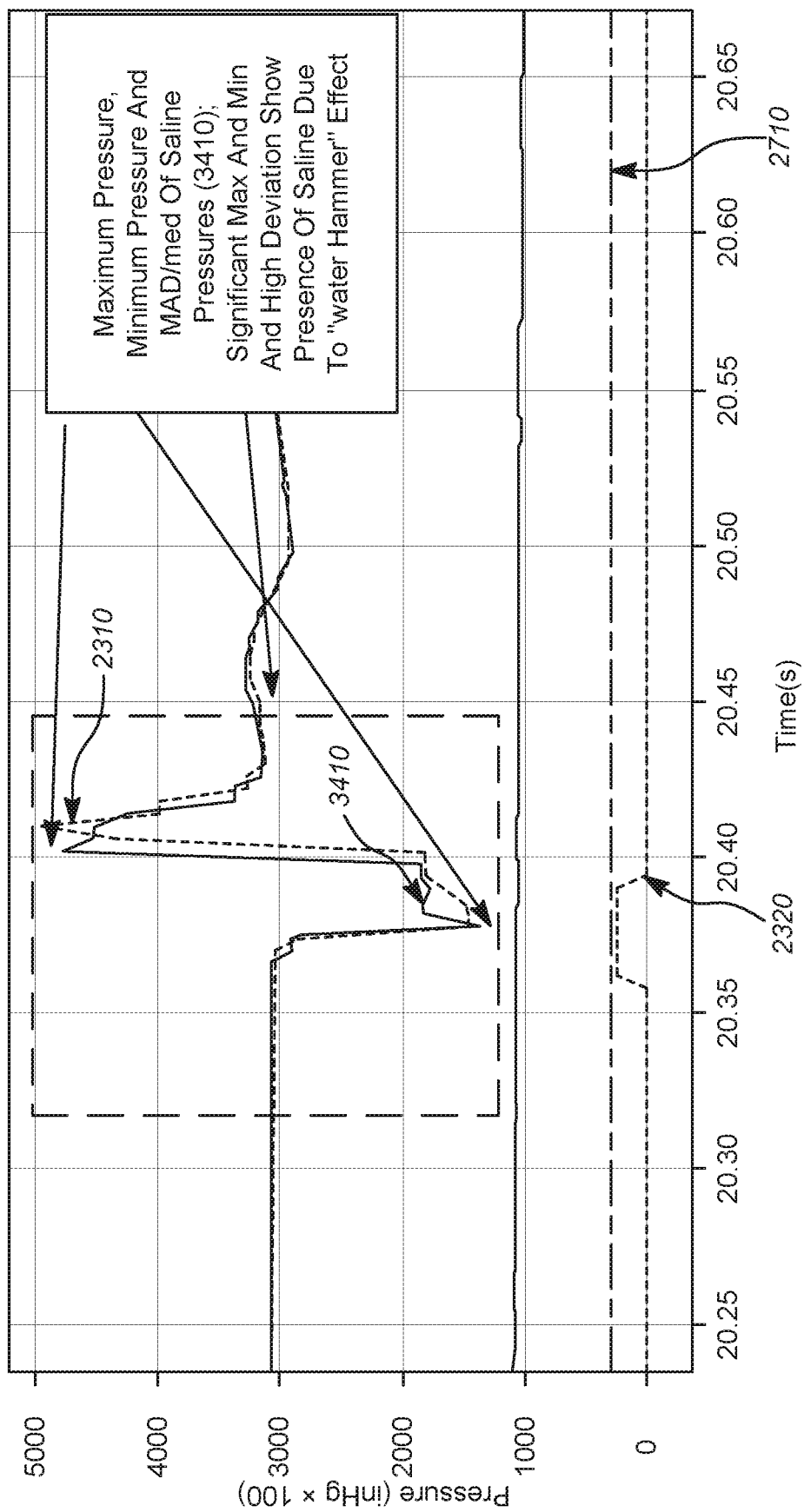
Figure 45:
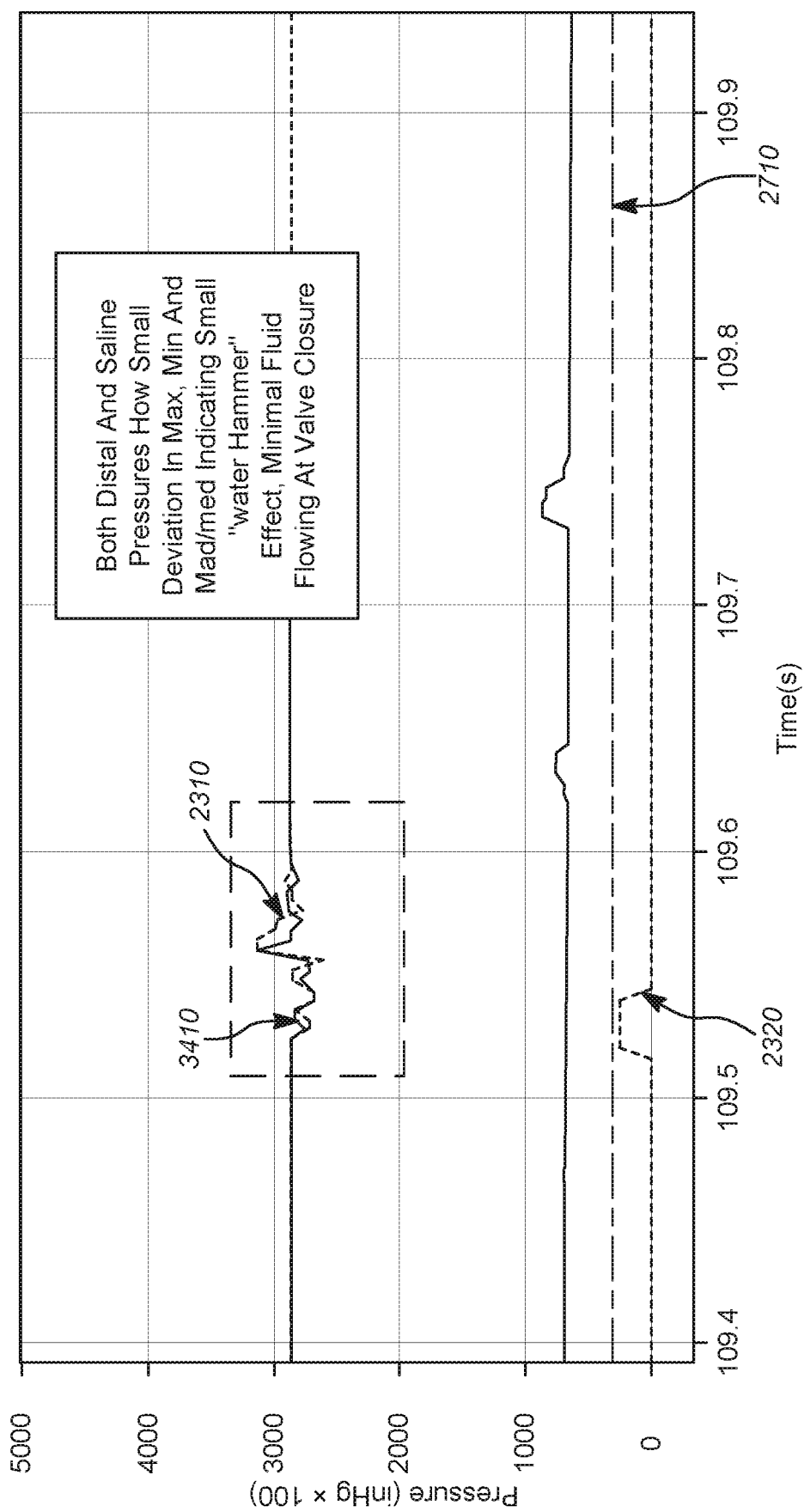

FIG. 43 illustrates a distal pressure profile 2310 taken during the middle of a successful priming sequence, in particular embodiments. Significantly high maximum and low minimum distal pressures, as well as high variances, may indicate inertial "water hammer" effects of the liquid relative to air, which may further indicate the presence of liquid saline. Similarly, FIG. 44 illustrates a saline pressure profile 3410 taken during the middle of a successful priming sequence, in particular embodiments. Significant high maximum and low minimum saline pressures, as well as high variances, may indicate inertial "water hammer" effects of the liquid relative to air, which may further indicate the presence of liquid saline. In contrast, FIG. 45 illustrates distal and saline pressure profiles taken during the middle of an unsuccessful priming sequence, in particular embodiments. Both exemplary pressure profiles illustrate small deviations in maximum and minimum pressures, and low variances, which may indicate low inertial "water hammer" effects and minimal fluid flow at vacuum valve closure.

Figure 46:
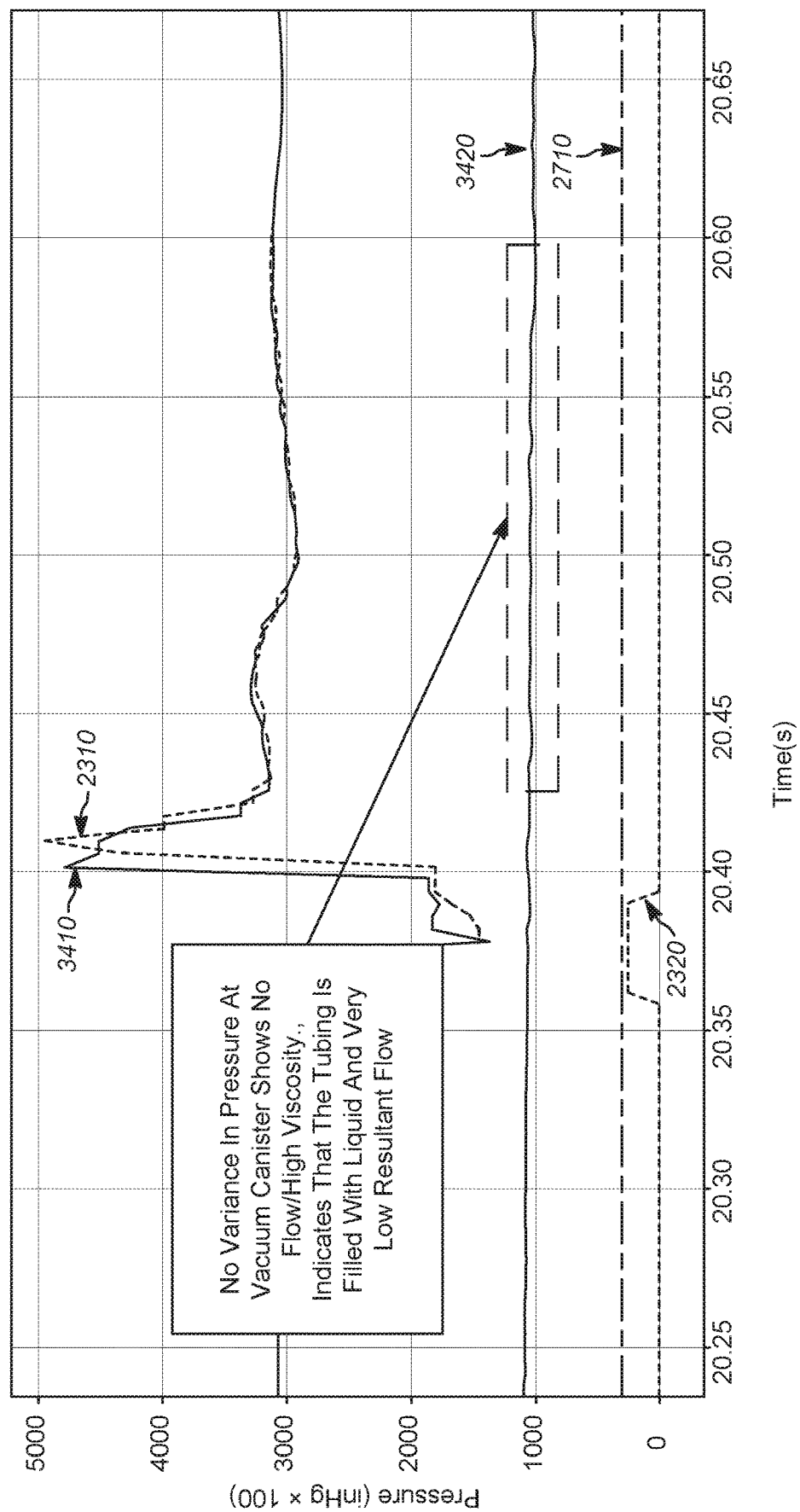
Figure 47:
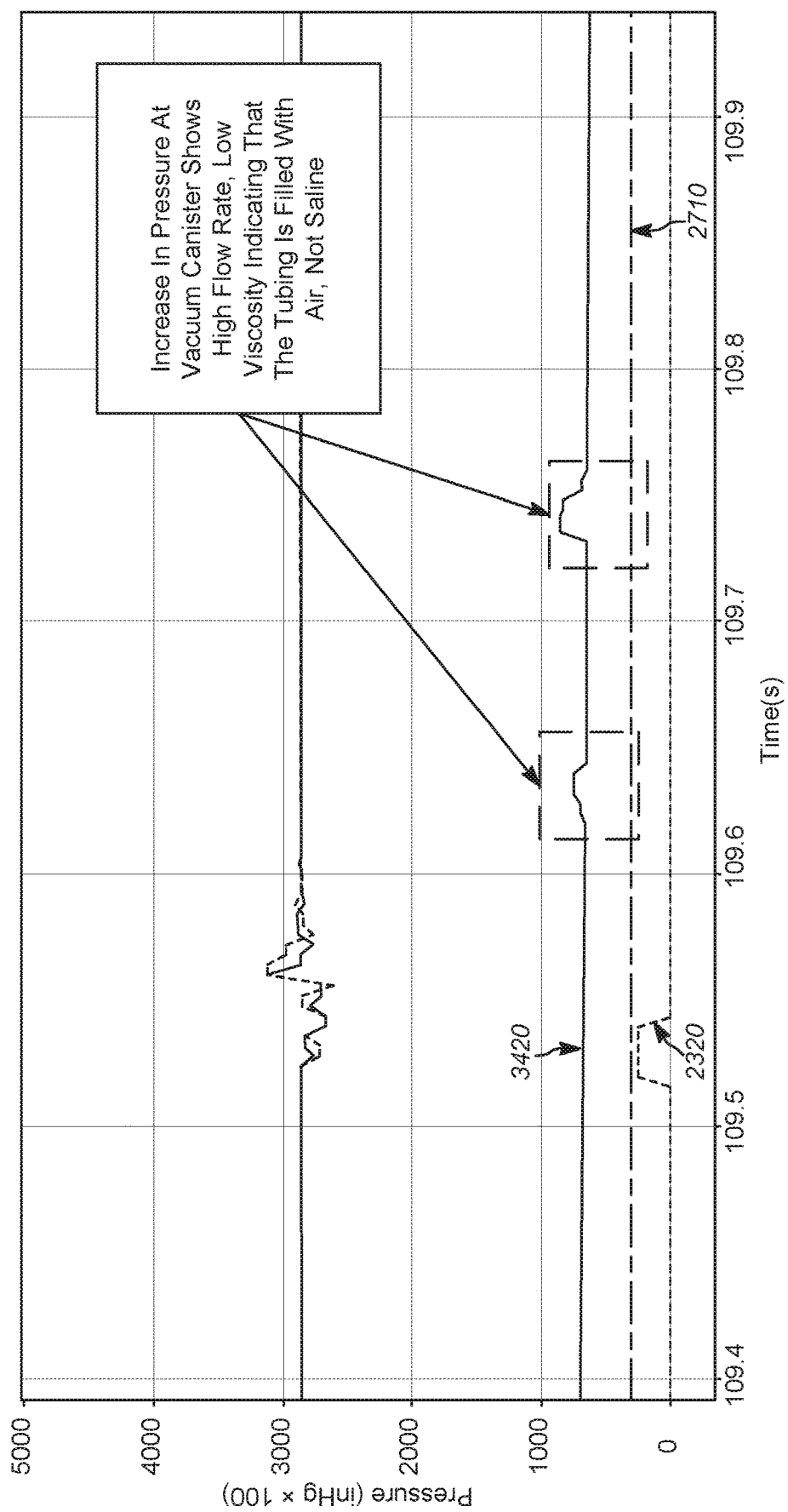

FIG. 46 illustrates a vacuum pressure profile taken during the middle of a successful priming sequence, in particular embodiments. Little or no variance in vacuum pressure may be observed at the vacuum canister, which may indicate no flow and/or high viscosity, further indicating that the tubing may be filled with liquid with very low resultant flow at the vacuum valve. In contrast, FIG. 47 illustrates a vacuum pressure profile taken during the middle of an unsuccessful priming sequence, in particular embodiments. Pressure increases at the vacuum canister may indicate high flow rates and/or low viscosity, indicating that the tubing may be filled with air, not liquid saline.

Figure 48:
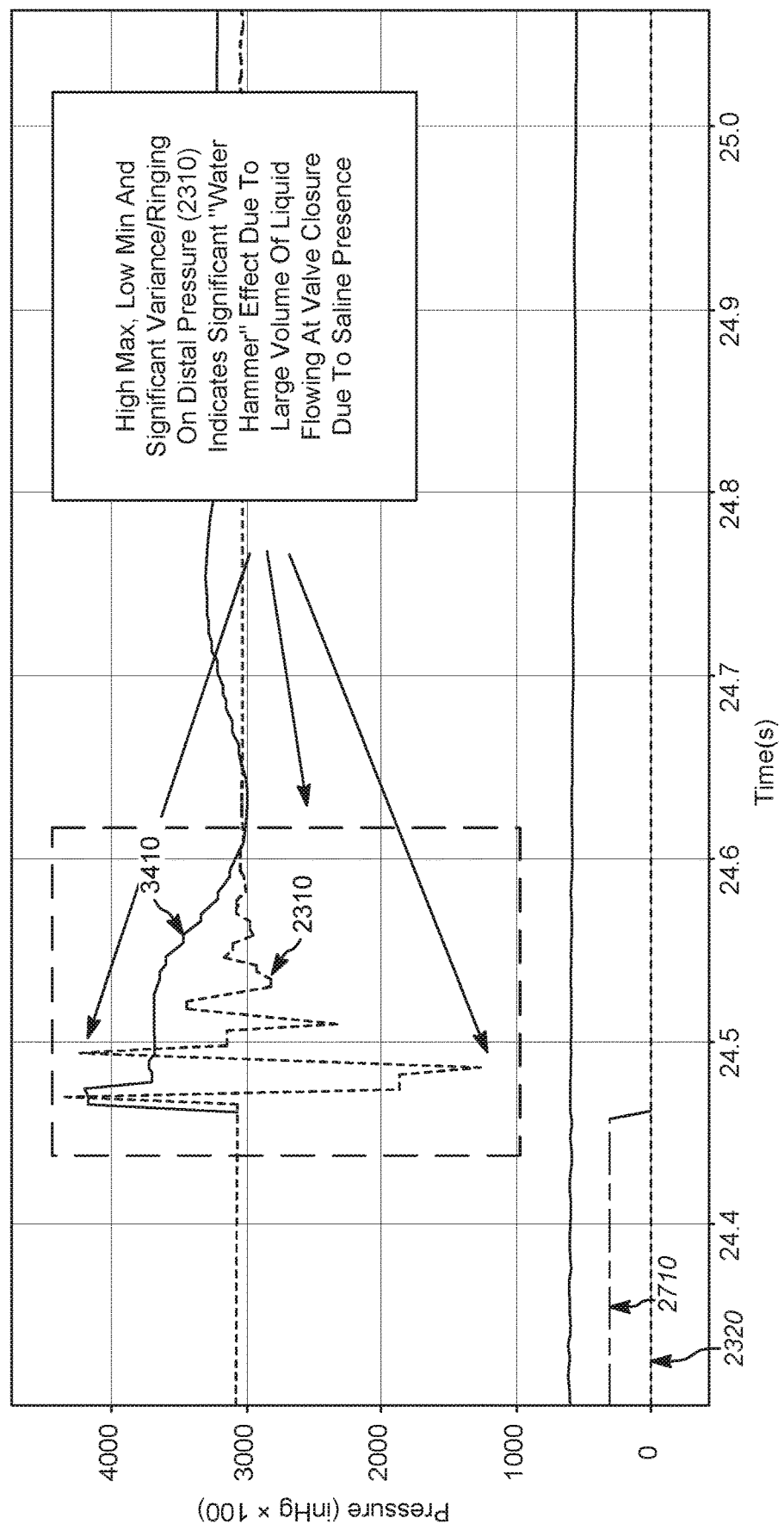
Figure 49:
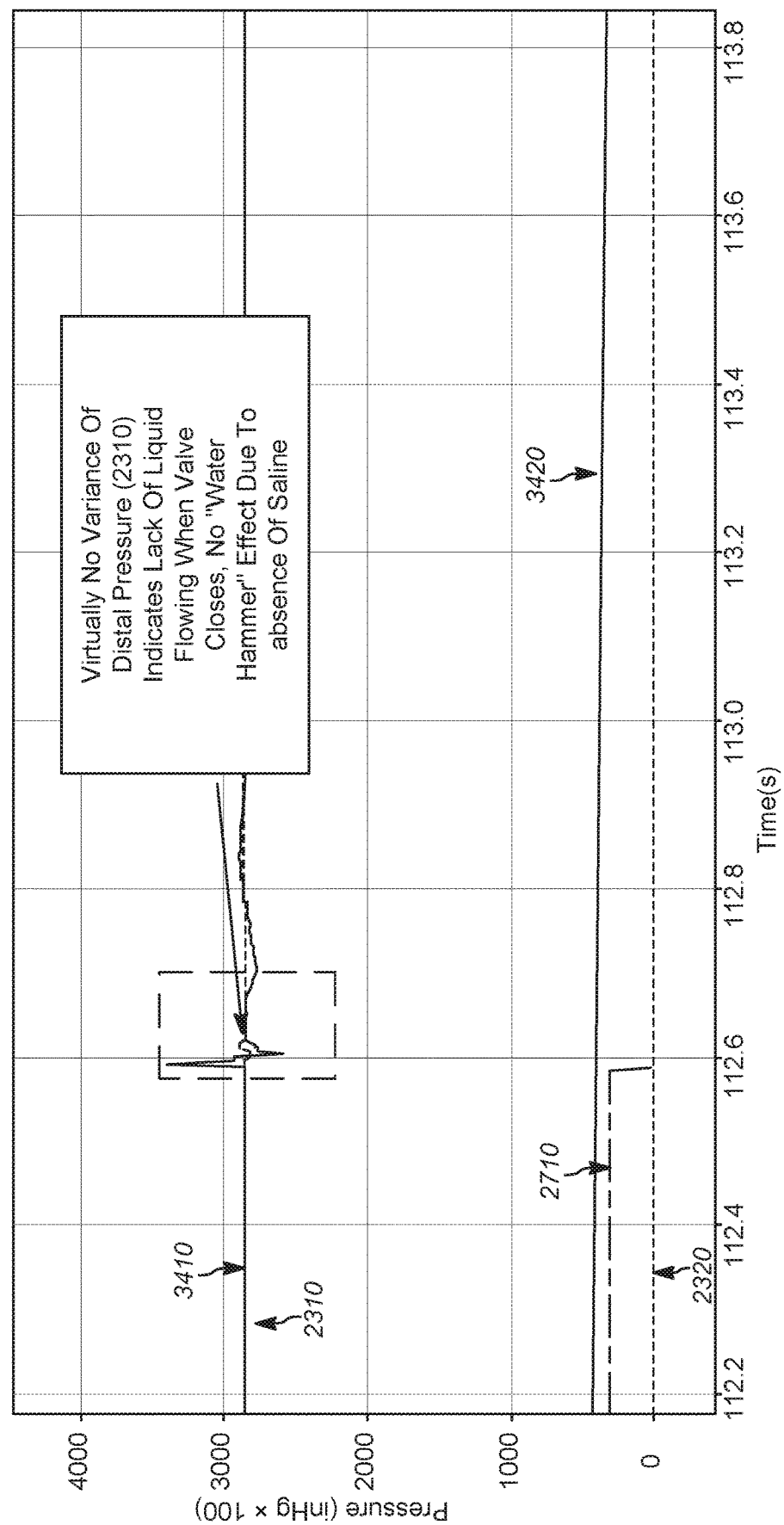

FIG. 48 illustrates a distal pressure profile taken near the end of a successful priming sequence, in particular embodiments. Significantly high maximum and low minimum distal pressures, as well as high variances and ringing or oscillations, may indicate inertial "water hammer" effects of the liquid relative to air due to large volumes of liquid flowing at pressure valve closure, which may be due to the presence of liquid saline. In contrast, FIG. 49 illustrates a distal pressure profile taken near the end of an unsuccessful priming sequence, in particular embodiments. Little or no variance of distal pressure may be observed, which may indicate a lack of liquid flowing when the pressure valve closes, with little or no inertial "water hammer" effects observed due to the relative absence of saline.

Figure 50:
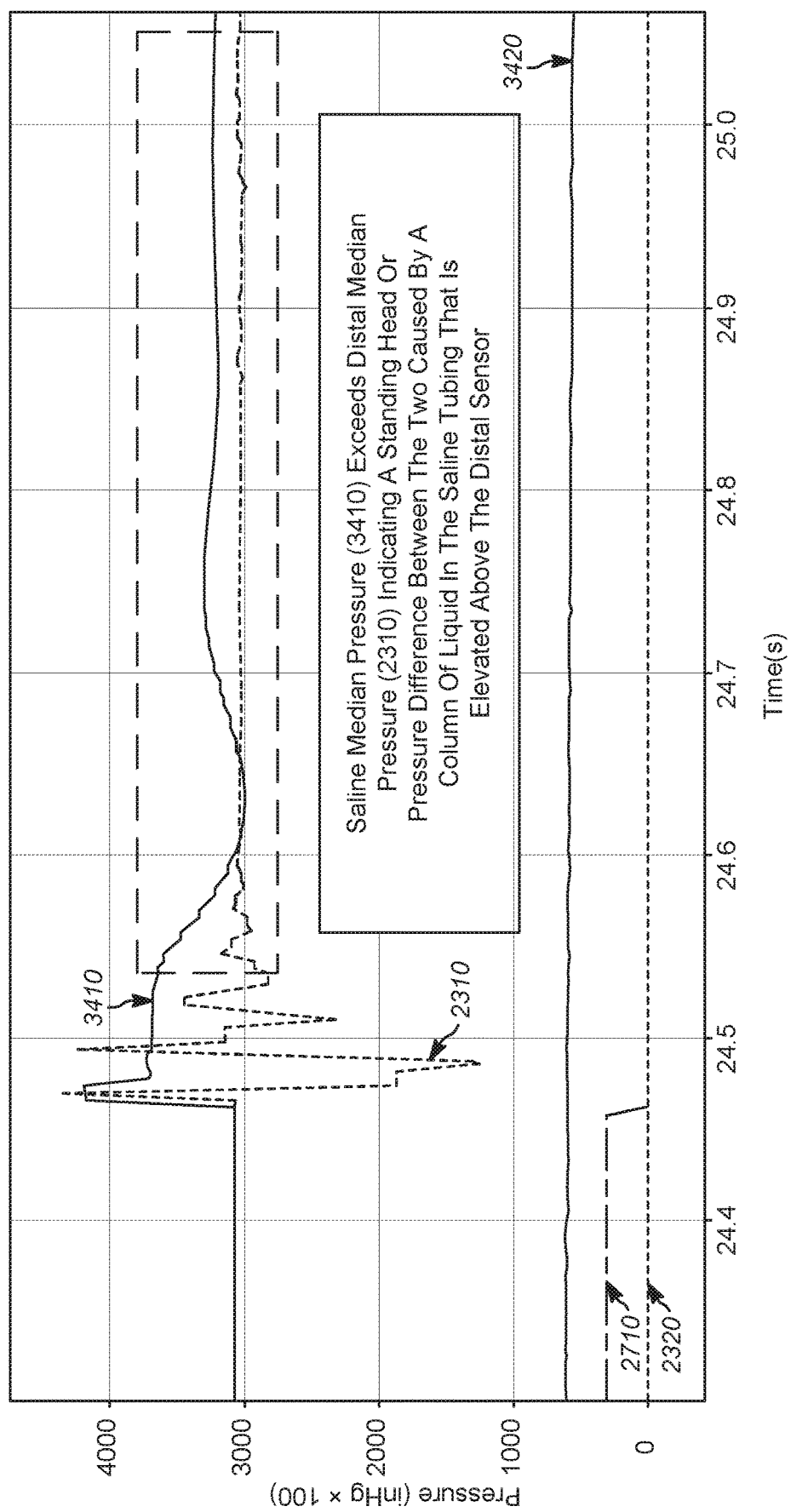

FIG. 50 illustrates a saline pressure profile taken near the end of a successful priming sequence, in particular embodiments. The median ending saline pressure exceeds the median ending distal pressure, which may indicate a standing head or pressure difference between the two pressures. This may be caused by a liquid column in the saline tubing that is elevated above the distal sensor.

Although this disclosure describes using particular sensor profiles, particular parameters and/or particular actuators such as vacuum valves for dynamically detecting system states and/or taking further action based on the determination, this disclosure contemplates providing any suitable providing any suitable sensors, actuators and/or methodologies for detecting system states or taking further action in any suitable manner.

As was previously discussed for determining of system states such as an open flow state, an occluded flow state, or "in-between" states based on system scores such as an Open Score and an Occlusion Score, in particular embodiments, the controller may be configured to detect system states relating to the relative presence or absence of liquid and gas, such as saline and air. For instance, each feature, such as those disclosed above, may be weighted, and the weighted sums of the features may be used to determine one or more corresponding system states. The above and following aspects are exemplary, and not limiting. It should be appreciated that methodologies for dynamic system state detection may vary across embodiments, and may be tailored based on specific configurations and/or applications.

In particular embodiments, dynamic system state detection may be used to determine whether a catheter is attached to the aspiration thrombectomy system. In particular embodiments, for flushing the system with saline, a catheter must not be connected to the system. Additionally, other factors indicating the presence of saline may be used for proceeding. As examples and not by way of limitation, FIGS. 51-52 illustrate pressure profile features of particular embodiments for catheter detection during flushing.

Figure 51:
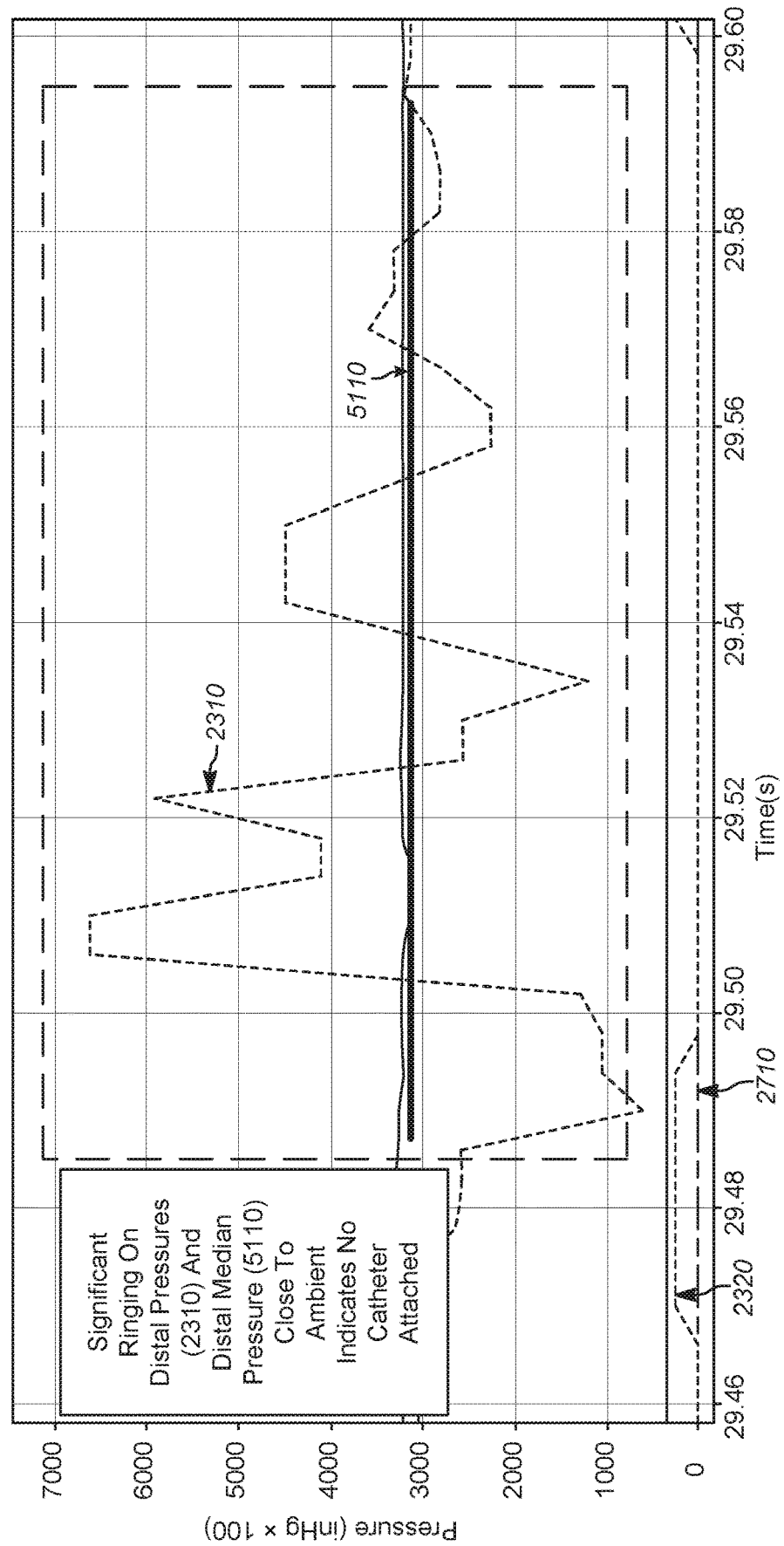
FIGS. 51-52 illustrate pressure profile features of particular embodiments for catheter detection during flushing.
Figure 52:
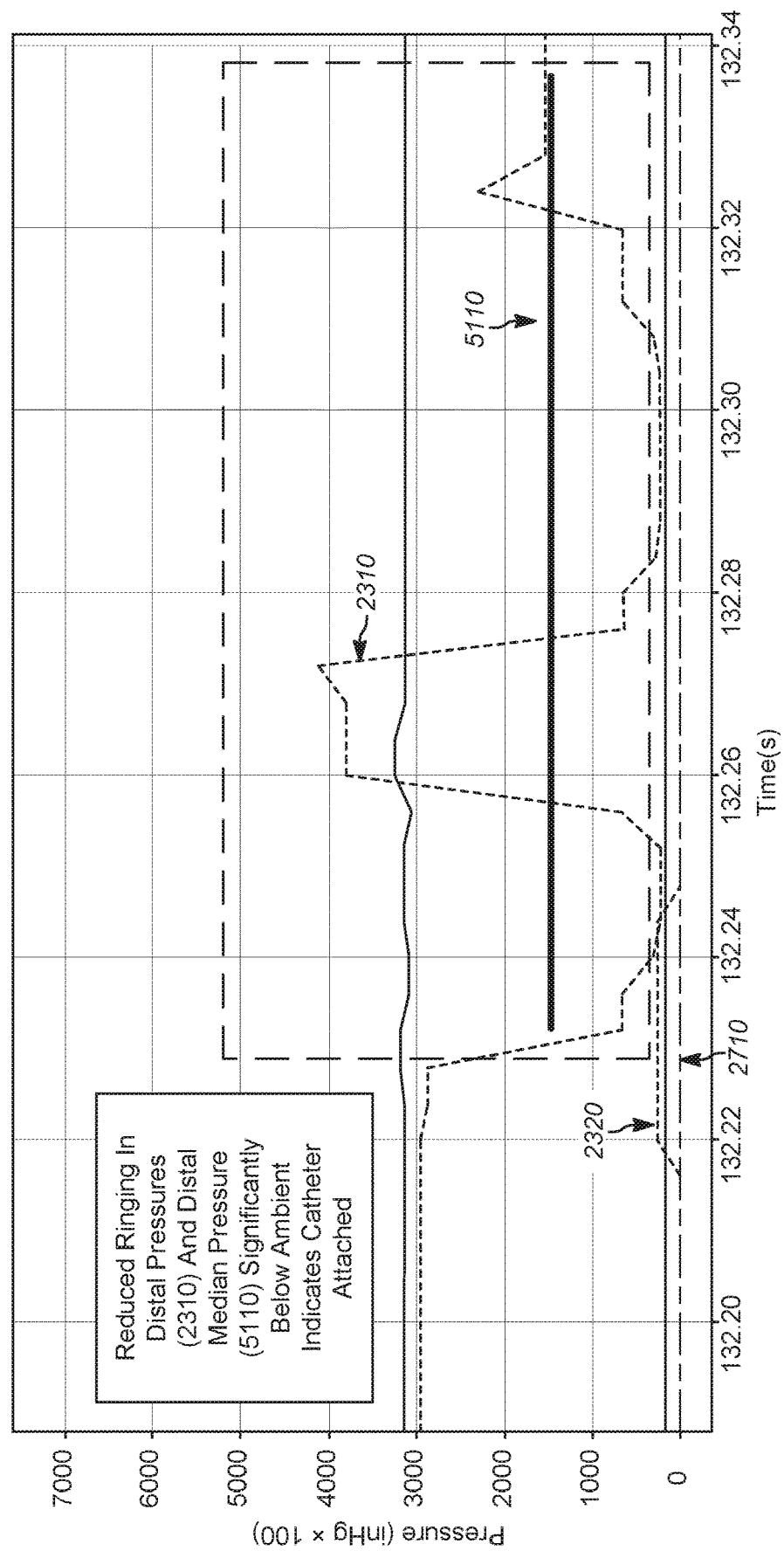

FIG. 51 illustrates a distal pressure profile taken at the start of a flush sequence, with no catheter attached to the system, in particular embodiments. Within the time interval or window of interest, based on cycling the vacuum valve, a large variance, or ringing, of distal pressures may be observed. Additionally, the median of the distal pressure 5110 during this time interval may be determined to be close to the local ambient pressure. This combination of features may indicate that no catheter is attached to the system. In contrast, FIG. 52 illustrates a distal pressure profile taken at the start of a flush sequence, with a catheter attached to the system, in particular embodiments. Based on cycling the vacuum valve, notably reduced variance or ringing of the distal pressure may be observed, along with a median of the distal during this time interval being significantly below the local ambient pressure, indicating that a catheter may be attached to the system.

Figure 53:
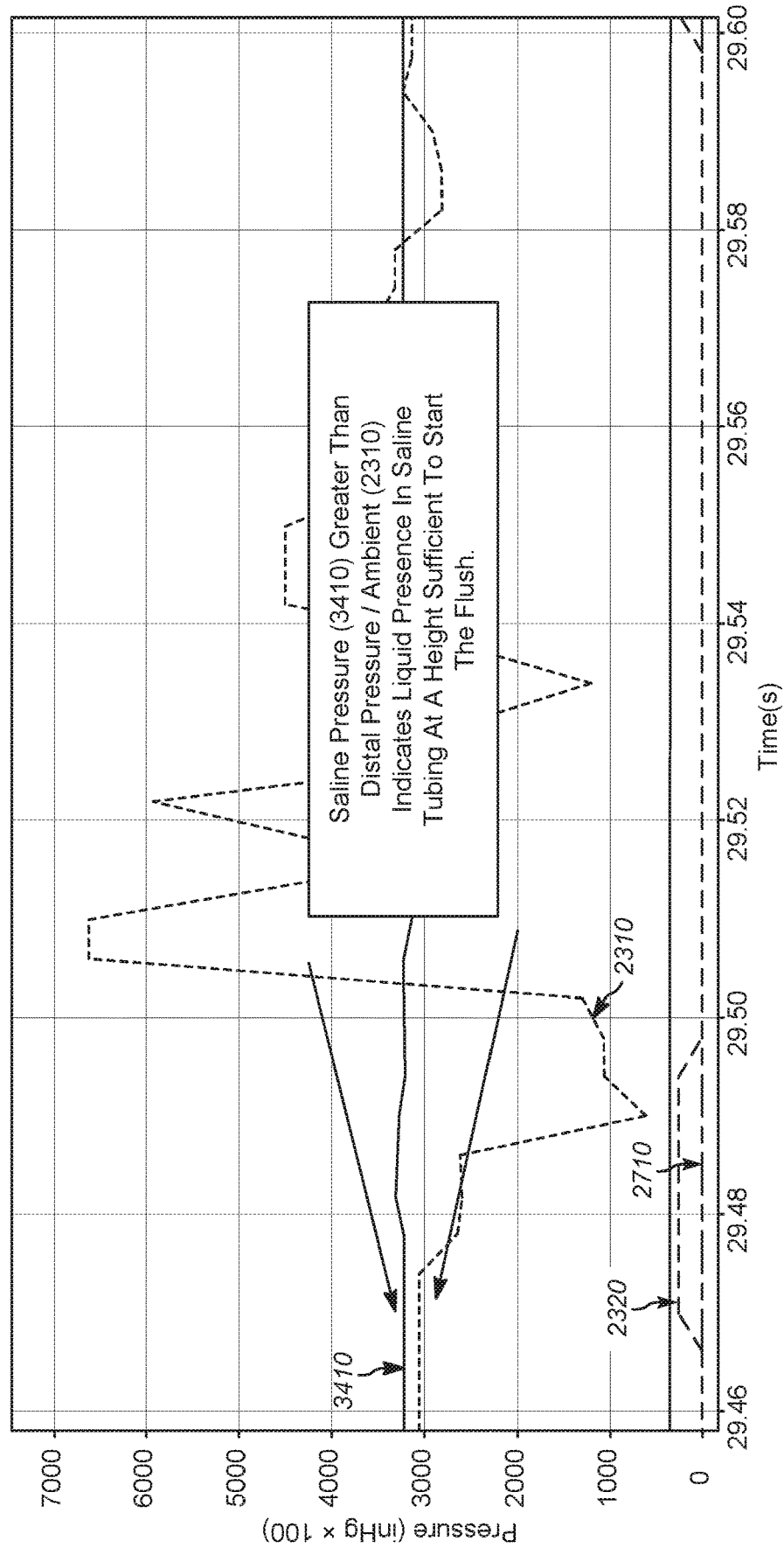
FIGS. 53-55 illustrate pressure profile features of particular embodiments for verifying liquid presence during flushing.
Figure 54:
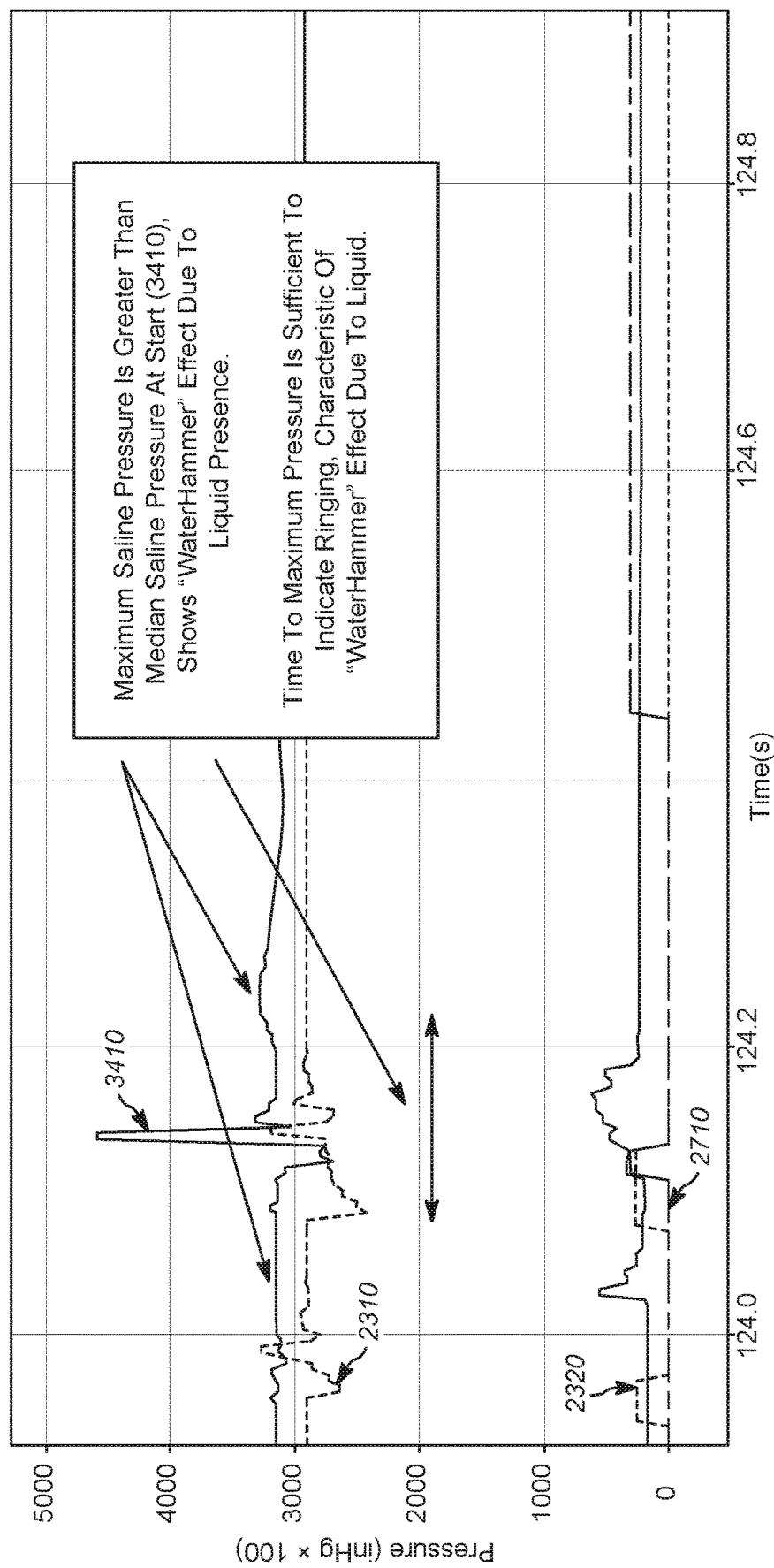
Figure 55:
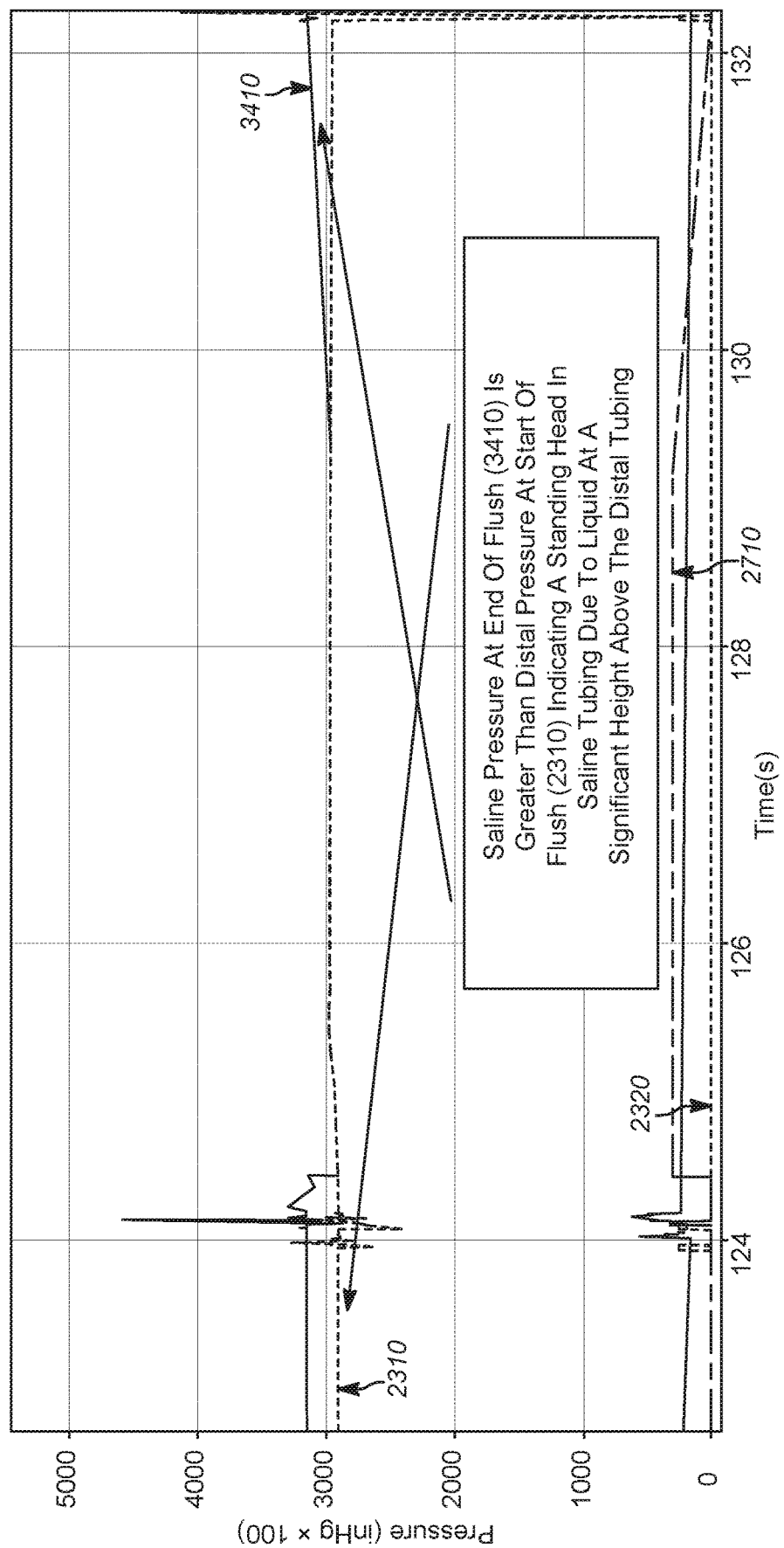
Figure 56:
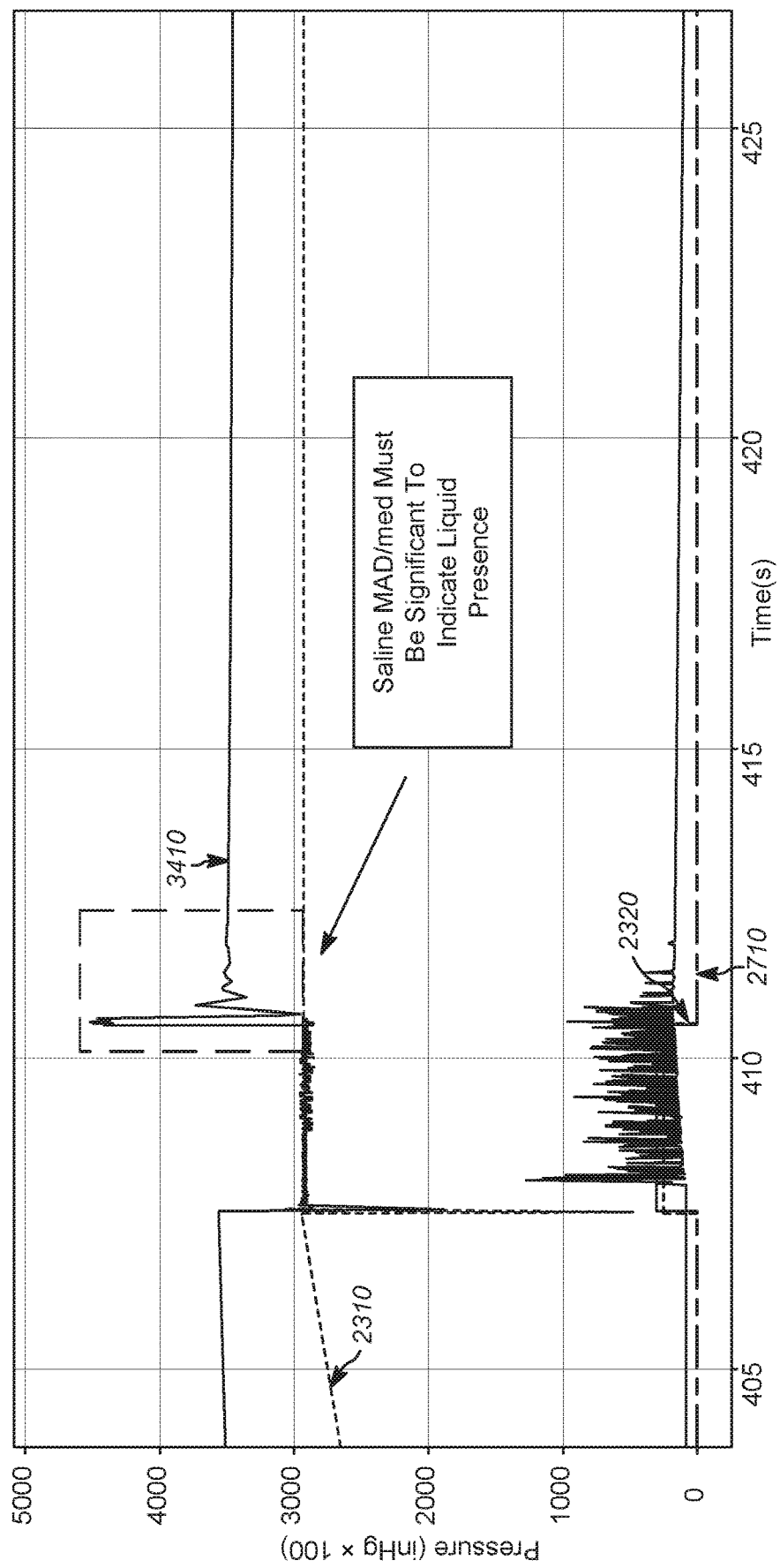
FIGS. 56-58 illustrate pressure profile features of particular embodiments for verifying liquid presence during repriming.
Figure 57:
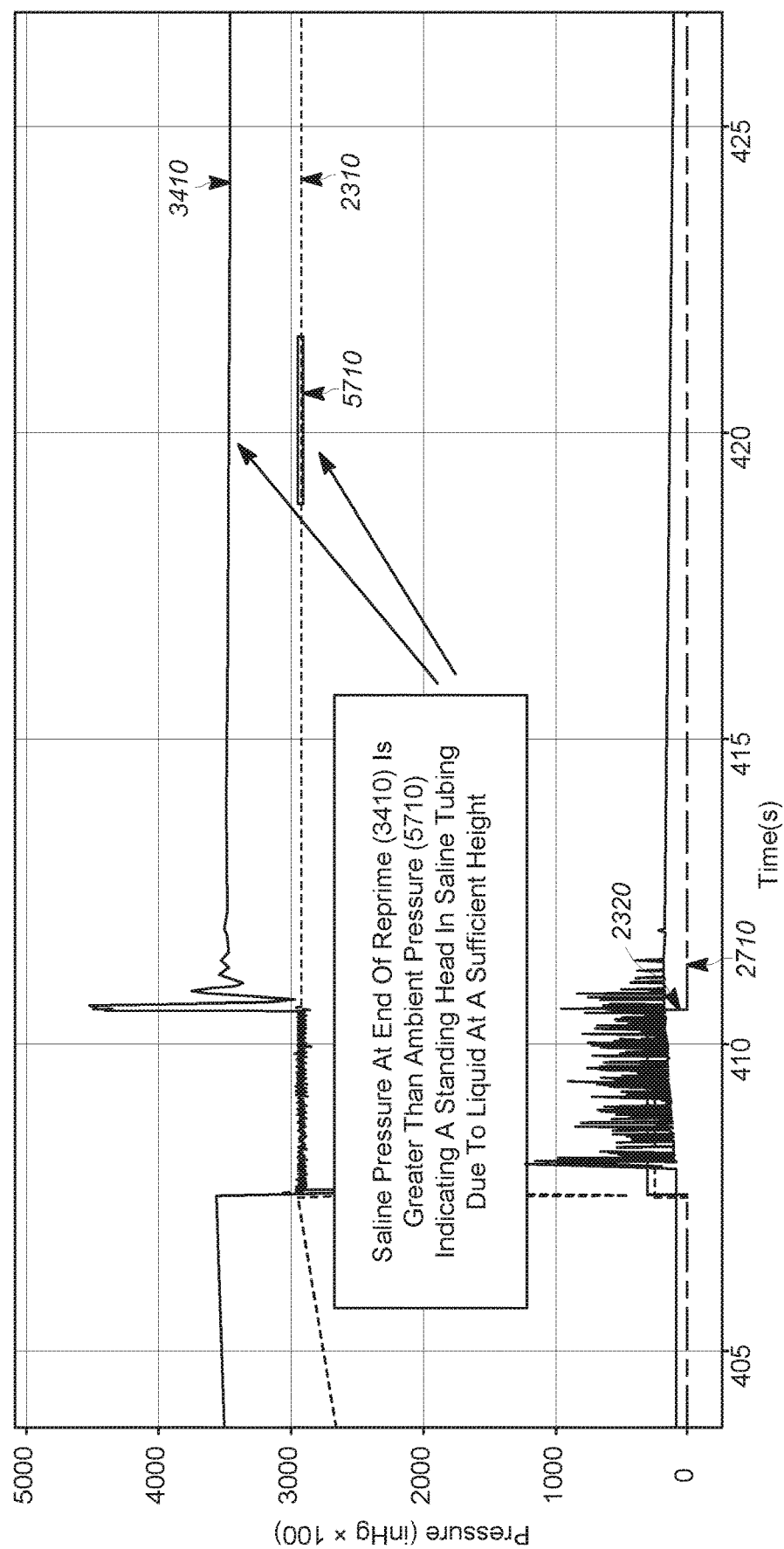
Figure 58:
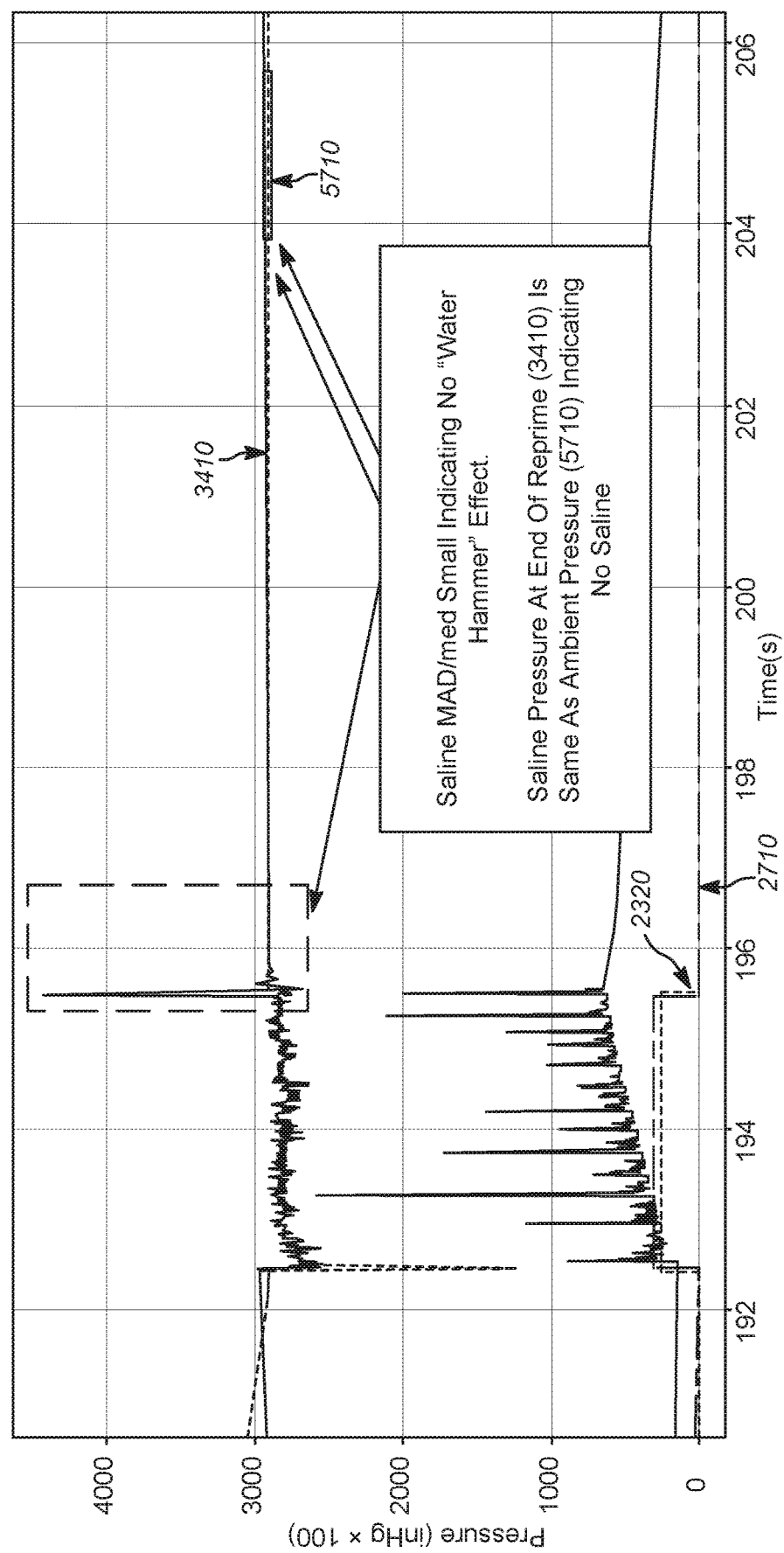

FIGS. 53-55 illustrate pressure profile features of particular embodiments for verifying liquid presence during flushing. FIG. 53 illustrates a saline pressure profile at the start of a flush sequence, in particular embodiments. The higher saline pressure relative to the distal or ambient pressure may indicate the presence of liquid in the saline tubing at a height sufficient to start the flush. FIG. 54 illustrates a saline pressure profile during the middle of a flush sequence, in particular embodiments. The higher maximum saline pressure relative to the median saline pressure at the start illustrates inertial "water hammer" effects due to the presence of liquid. Further, the time taken to reach maximum saline pressure may be sufficient to indicate ringing in this particular example. FIG. 55 illustrates a saline pressure profile during at the end of a flush sequence, in particular embodiments. The saline pressure at the end of the flush is greater than the distal pressure at the start of the flush, which may indicate a standing head in saline tubing due to liquid at a significant height above the distal tubing. These illustrations are provided as examples and not by way of limitation, In particular embodiments, dynamic system state detection may be used to determine the presence or absence of saline during a repriming sequence. As examples, and not by way of limitation, FIGS. 56-58 illustrate pressure profile features of particular embodiments for verifying liquid presence during repriming. FIGS. 56 and 57 illustrate a saline pressure profile taken at the end of a successful repriming sequence, in particular embodiments. As illustrated in FIG. 56, a significant variance (using a metric such as a MAD/med) of saline pressure detected during a time interval window following valve closure may be used to verify liquid presence. As illustrated in FIG. 57, a saline pressure at the end of reprime being greater than the ambient pressure level 5710 may be indicative of a standing head in the saline tubing due to liquid at a sufficient height. In contrast, FIG. 58 illustrates a saline pressure profile corresponding to an unsuccessful repriming sequence, in particular embodiments. A low variance (using a metric such as a MAD/med) of saline pressure detected during a time interval window following valve closure may indicate a lack of inertial "water hammer" effects, which may further indicate a lack of liquid saline. Additionally, saline pressure at the end of reprime is observed to be the same as the ambient pressure, which may also indicate a lack of saline.

Figure 59:
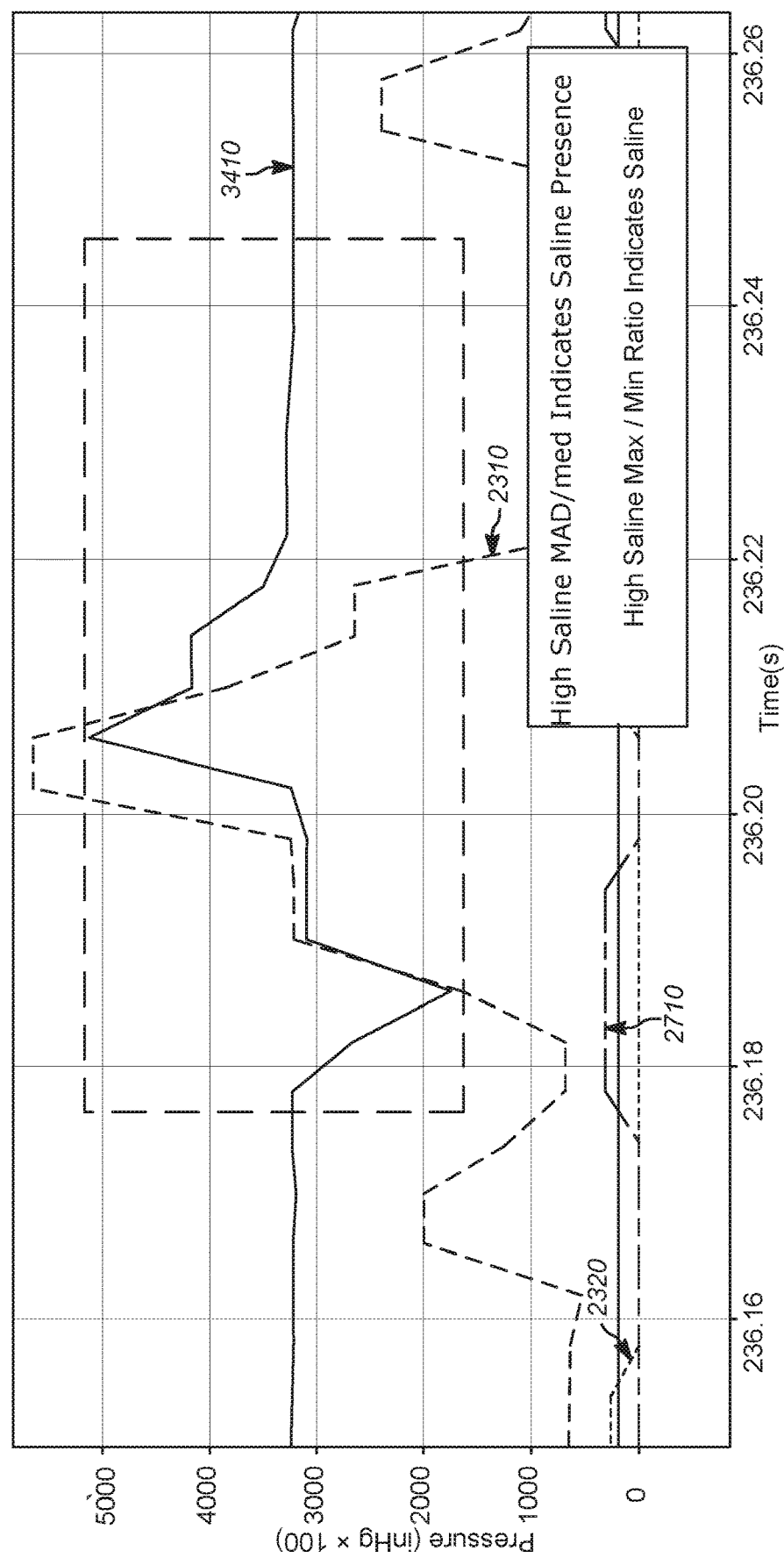
FIGS. 59-60 illustrate pressure profile features of particular embodiments for saline detection during a pulse sequence.
Figure 60:
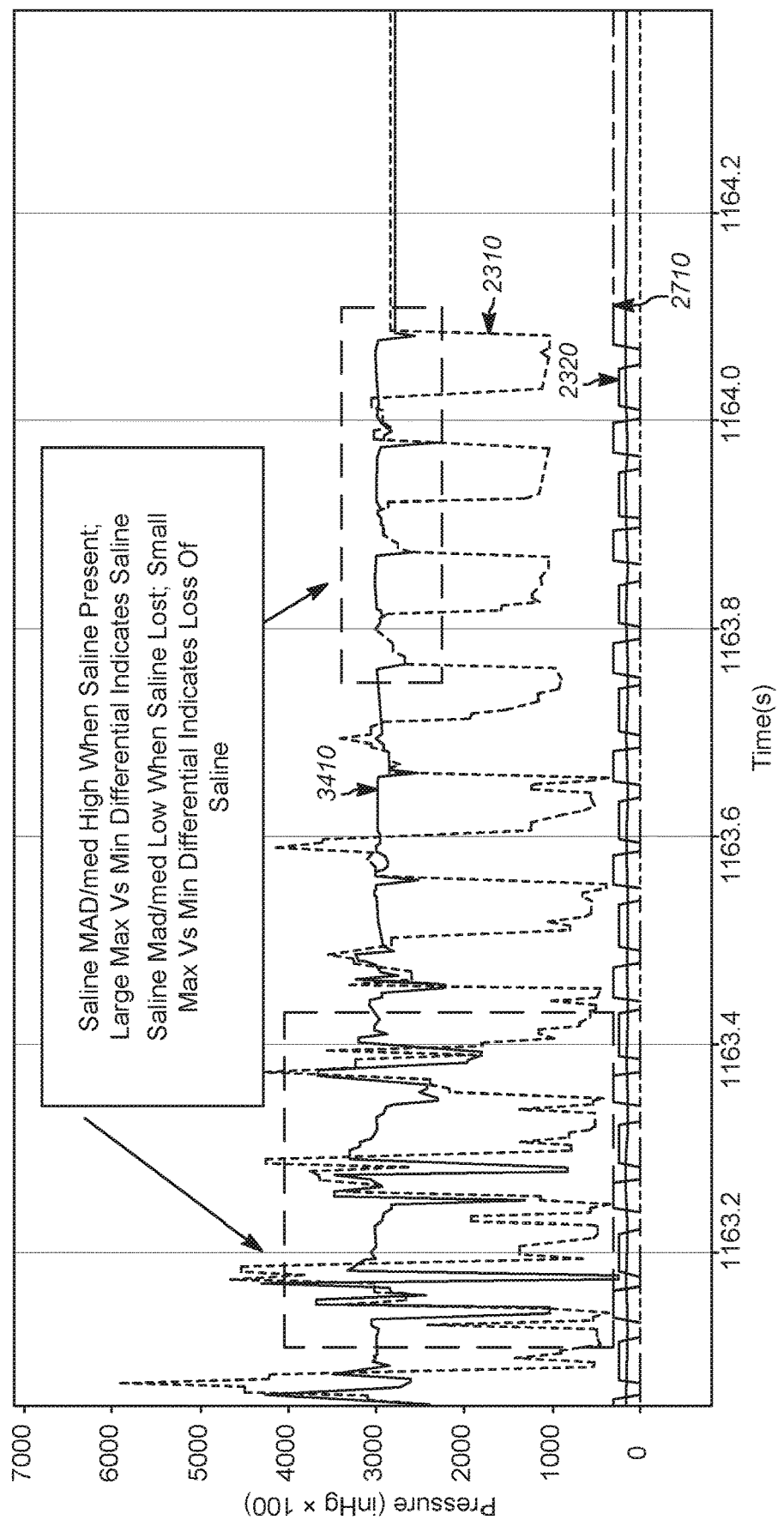

In particular embodiments, dynamic system state detection may be used to determine the presence or absence of saline during a pulse sequence. As examples, and not by way of limitation, FIGS. 59-60 illustrate pressure profile features of particular embodiments for saline detection during a pulse sequence. FIG. 59 illustrates a saline pressure profile during a pulse sequence, in particular embodiments. A high variance of saline pressure (using a metric such as a MAD/med) detected during a time interval window based on operating the pressure valve may indicate saline presence. Additionally, a high ratio of maximum to minimum saline pressures may indicate saline presence. FIG. 60 illustrates detection of loss of saline during pulsing, in particular embodiments. While the early time interval window during pulsing illustrates a high variance of saline pressure, and a large ratio of maximum to minimum saline pressures, all indicating possible saline presence, the later stage time interval window illustrates a significantly lower variance of saline pressure, and a significantly lower ratio of maximum to minimum saline pressures, all indicating possible loss of saline during pulsing.

In particular embodiments, dynamic system state detection may be used to determine whether a clot has been engaged. In particular embodiments, initiation of modulated aspiration may follow such a determination of clot engagement. In particular embodiments, such a determination may be separately or additionally used to initiate a maceration cycle for applying mechanical forces on occlusive material. Such mechanical action may be applied to sufficiently modify the form and/or consistency of a clot or other occlusive material to enable more effective aspiration.

Figure 61:
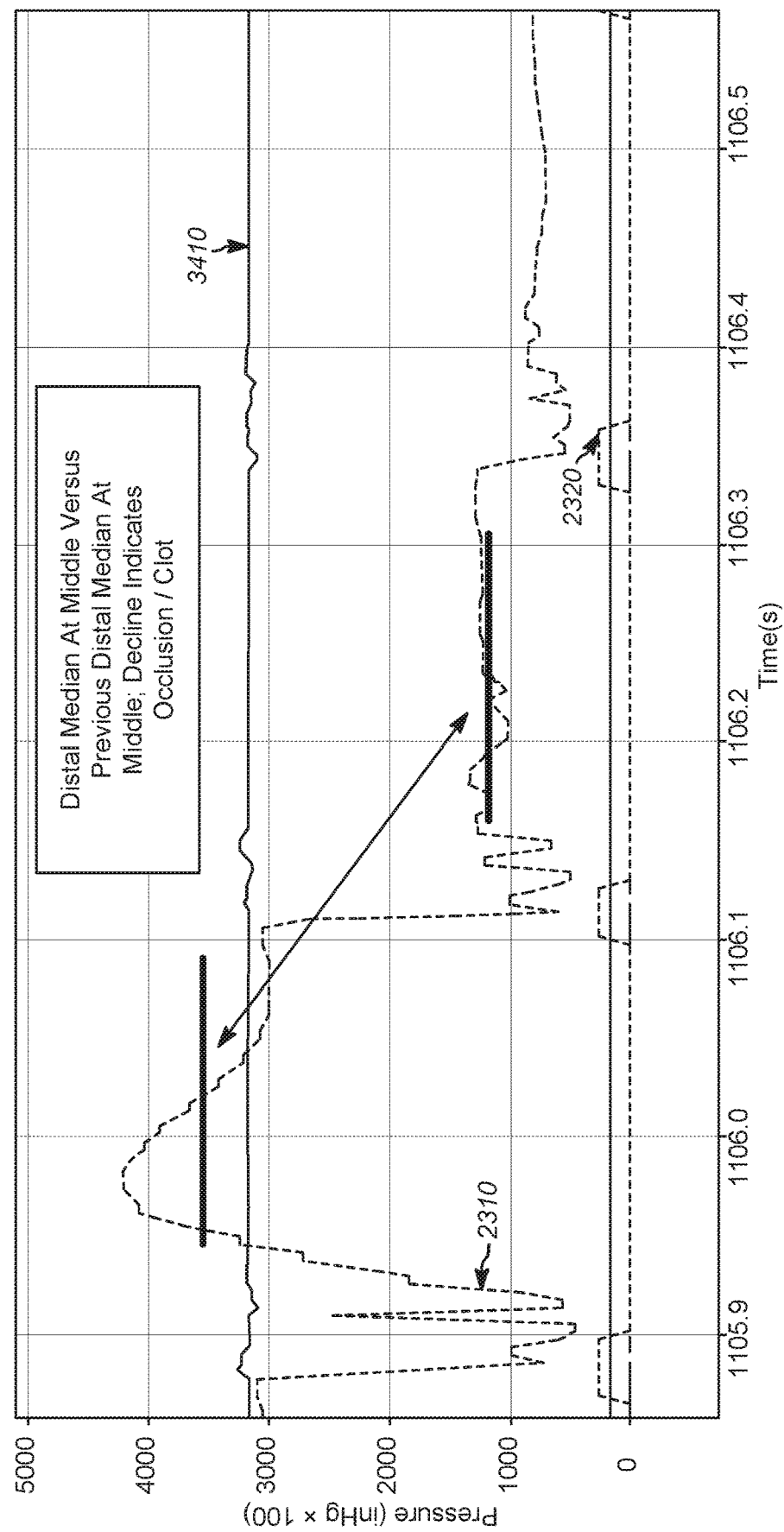
FIGS. 61-65 illustrate pressure profile features of particular embodiments for clot detection corresponding to a pulse sequence.

As examples, and not by way of limitation, FIGS. 61-65 illustrate pressure profile features of particular embodiments for clot detection corresponding to a pulse sequence. FIG. 61 illustrates a distal pressure profile during a pulse sequence, in particular embodiments. A comparison of the median distal pressures taken during the middle of the time intervals between vacuum valve cycling events illustrates a decline in the median value across two consecutive such detections, which may indicate the presence of an occlusion or clot.

Figure 62:
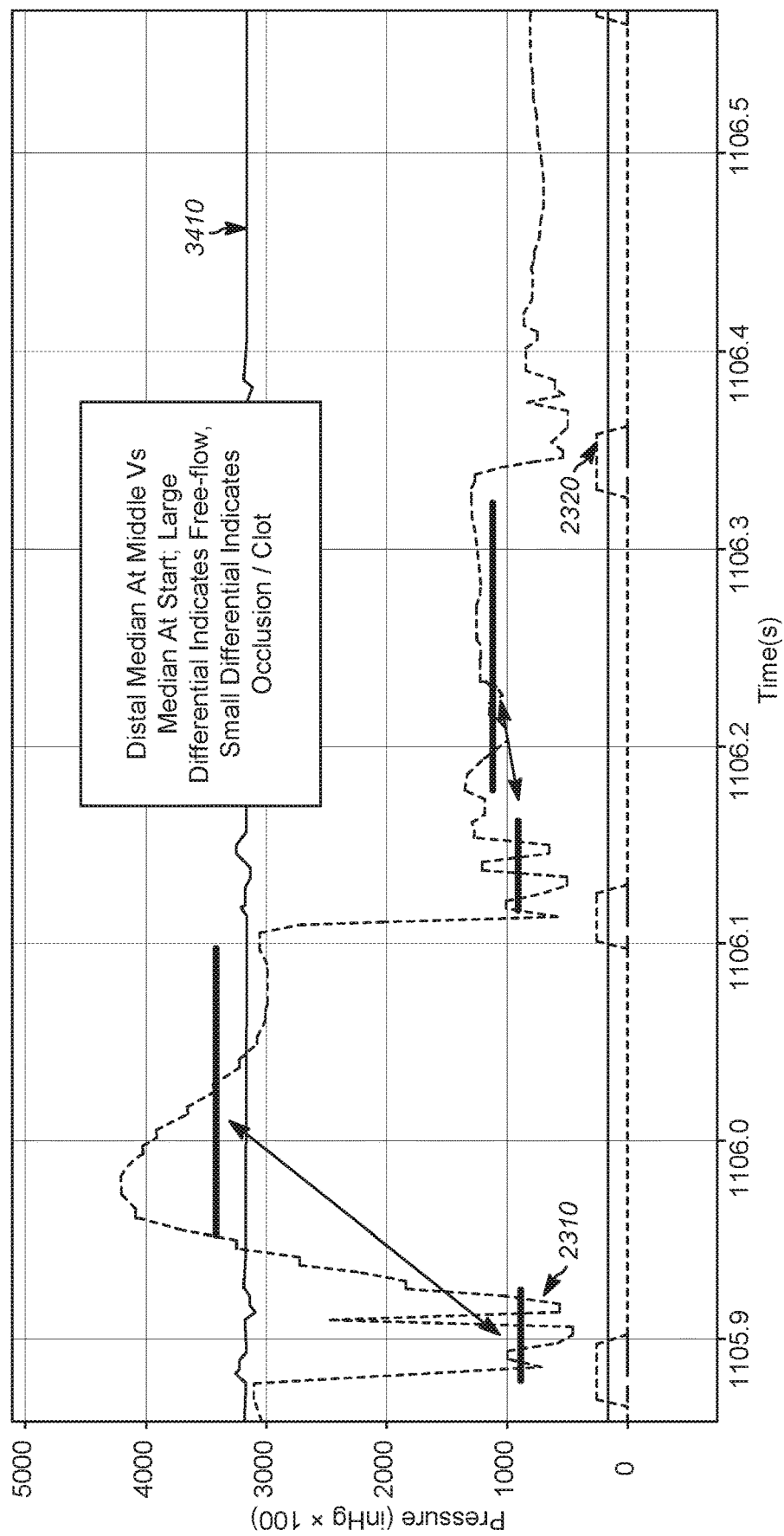

FIG. 62 illustrates a distal pressure profile during a pulse sequence, in particular embodiments. In a first case corresponding to the first cycling of the vacuum valve around the 1105.9 s time marker, the median value of the distal pressure taken at the start is compared to the median value of the distal pressure taken at the middle of the pulsing cycle. A large differential between these median pressures, as observed in the first case, may be indicative of open or unrestricted flow. In a second case corresponding to the second cycling of the vacuum valve that starts around the 1106.1 s time marker, a small differential between the median pressures is observed, which may be indicating the presence of an occlusion or clot.

Figure 63:
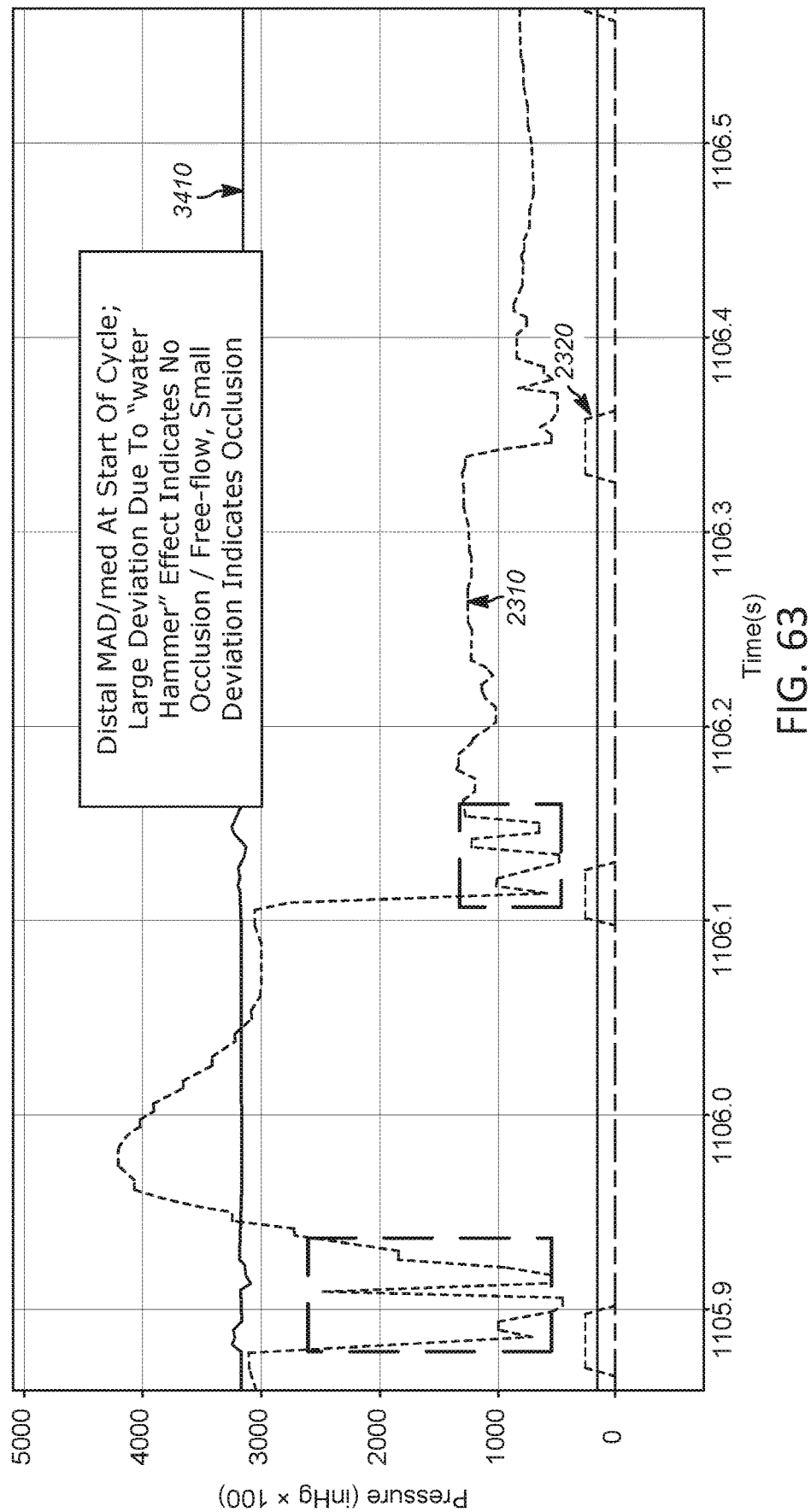

FIG. 63 illustrates a distal pressure profile during a pulse sequence, in particular embodiments. In a first case corresponding to a short time window taken at the start of the first cycling of the vacuum valve around the 1105.9 s time marker, the variance of distal pressure (using a metric such as MAD/med) is large due to inertial "water hammer" effects, which may be indicating open, free, or unrestricted flow. In a second case corresponding to a short time window taken at the start to the second cycling of the vacuum valve that starts around the 1106.1 s time marker, the variance of distal pressure (using a metric such as MAD/med) is small, which may be indicating the presence of an occlusion or clot.

Figure 64:
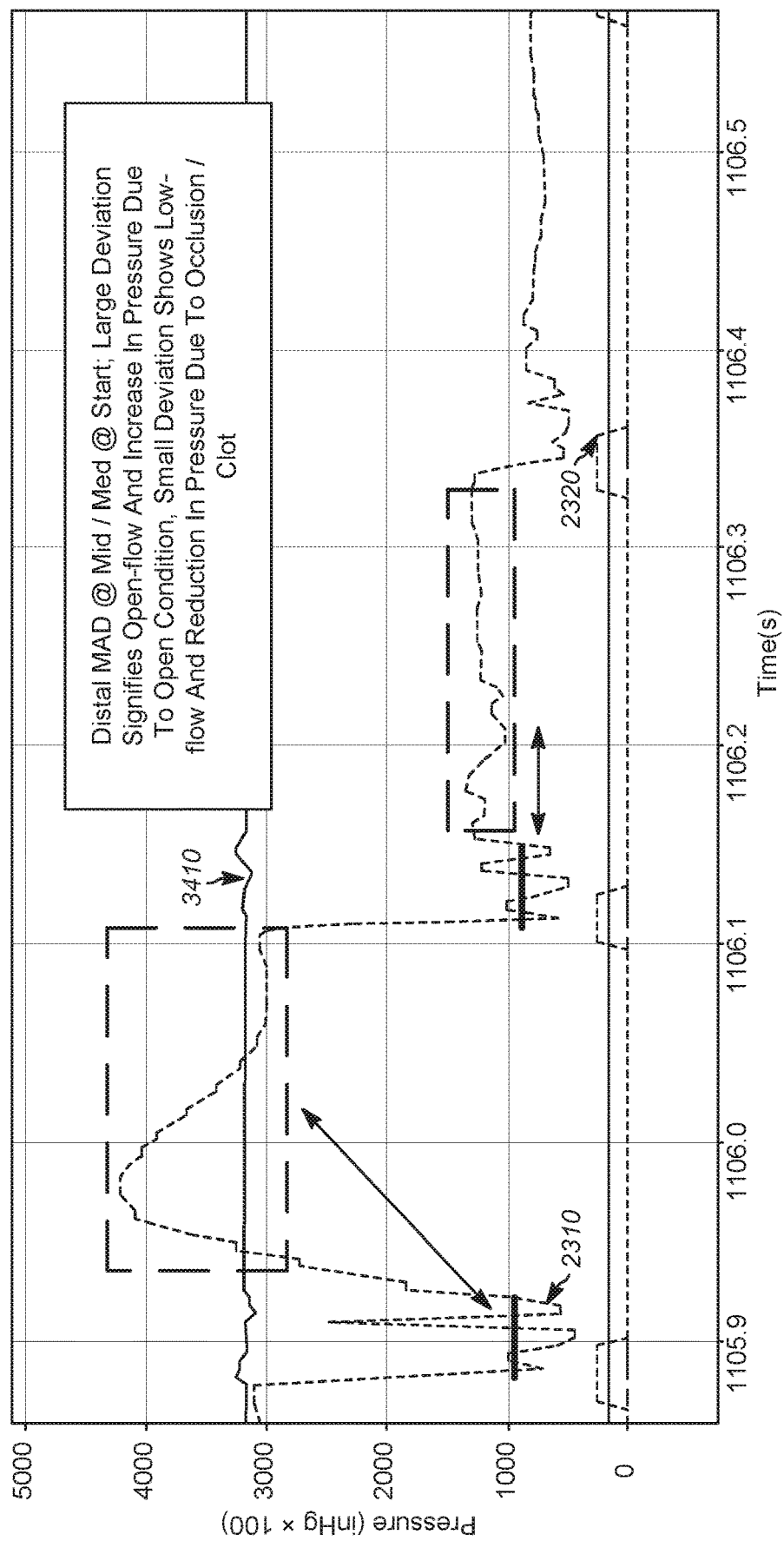

FIG. 64 illustrates a distal pressure profile during a pulse sequence, in particular embodiments. In a first case corresponding to the first cycling of the vacuum valve around the 1105.9 s time marker, the median distal pressure at the start of the pulse cycle is compared to the mean absolute deviation of distal pressure during the middle of the pulse cycle. The large deviation(s) observed may indicate open flow conditions, and corresponding increase in pressure. In a second case corresponding to the second cycling of the vacuum valve that starts around the 1106.1 s time marker, the median distal pressure at the start of the second pulse cycle is again compared to the mean absolute deviation of distal pressure during the middle of the second pulse cycle. Small deviation(s) observed may indicate low flow conditions, and reduction in pressure due to the possible presence of an occlusion or clot.

Figure 65:
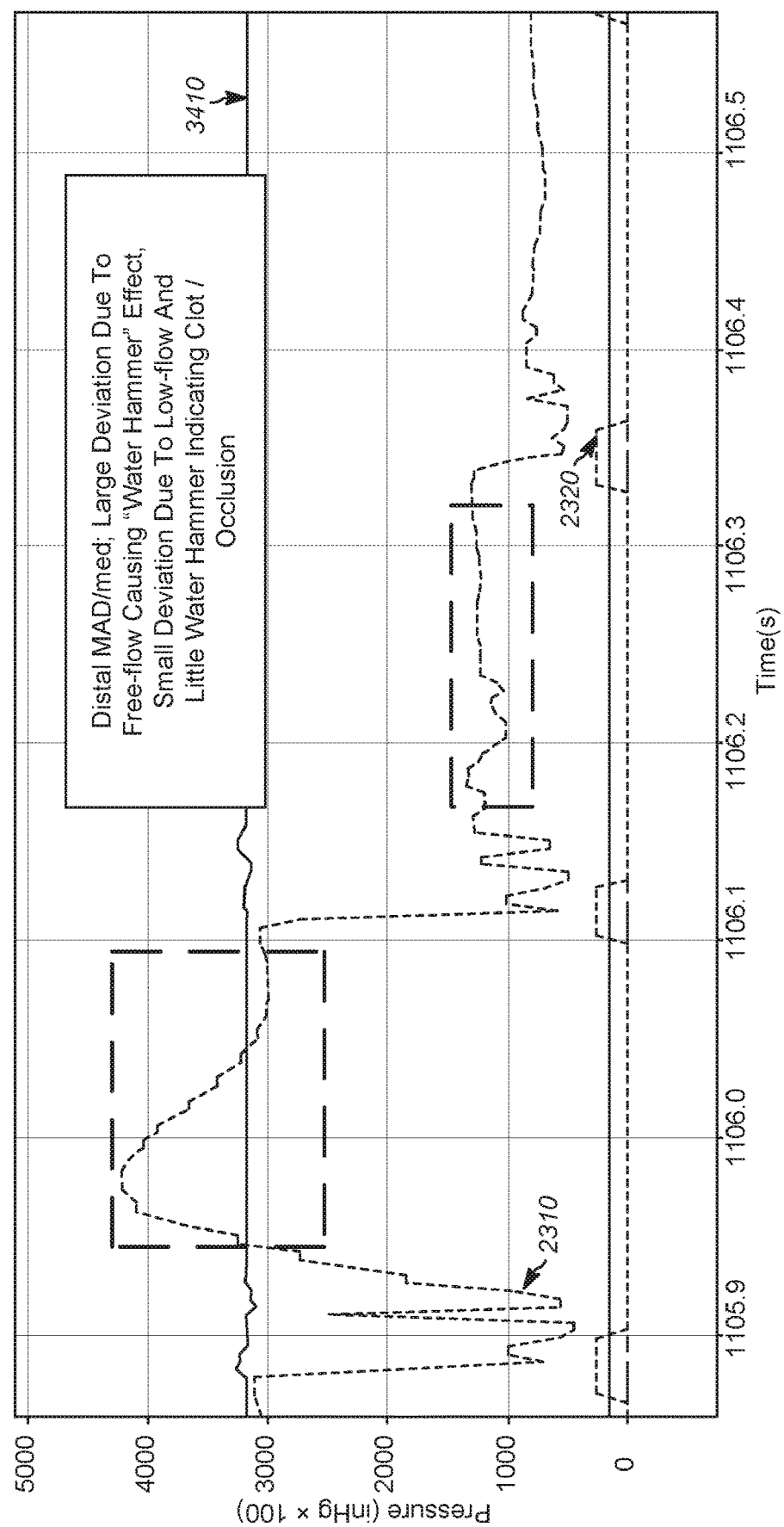

FIG. 65 illustrates a distal pressure profile during a pulse sequence, in particular embodiments. In a first case corresponding to a large time interval window taken during the middle of the first cycling of the vacuum valve that start around the 1105.9 s time marker, the variance of distal pressure (using a metric such as MAD/med) is large due to inertial "water hammer" effects, which may indicate open, free, or unrestricted flow. In a second case corresponding to a large time interval window taken during the middle of the second cycling of the vacuum valve that starts around the 1106.1 s time marker, the variance of distal pressure (using a metric such as MAD/med) is small, which may indicate the presence of an occlusion or clot.

In particular embodiments, dynamic system state detection may involve the use of multiple sensors, such as multiple pressure sensors, including interactions between multiple sensors. As examples, and not by way of limitation, FIGS. 66-70 illustrate pressure profiles of particular embodiments detected using multiple pressure sensors, P1 and P2, used for dynamic system state detection. It should be appreciated that using multiple sensors for dynamic system state detection may vary across embodiments, and may be tailored based on specific configurations and/or applications.

Figure 66:
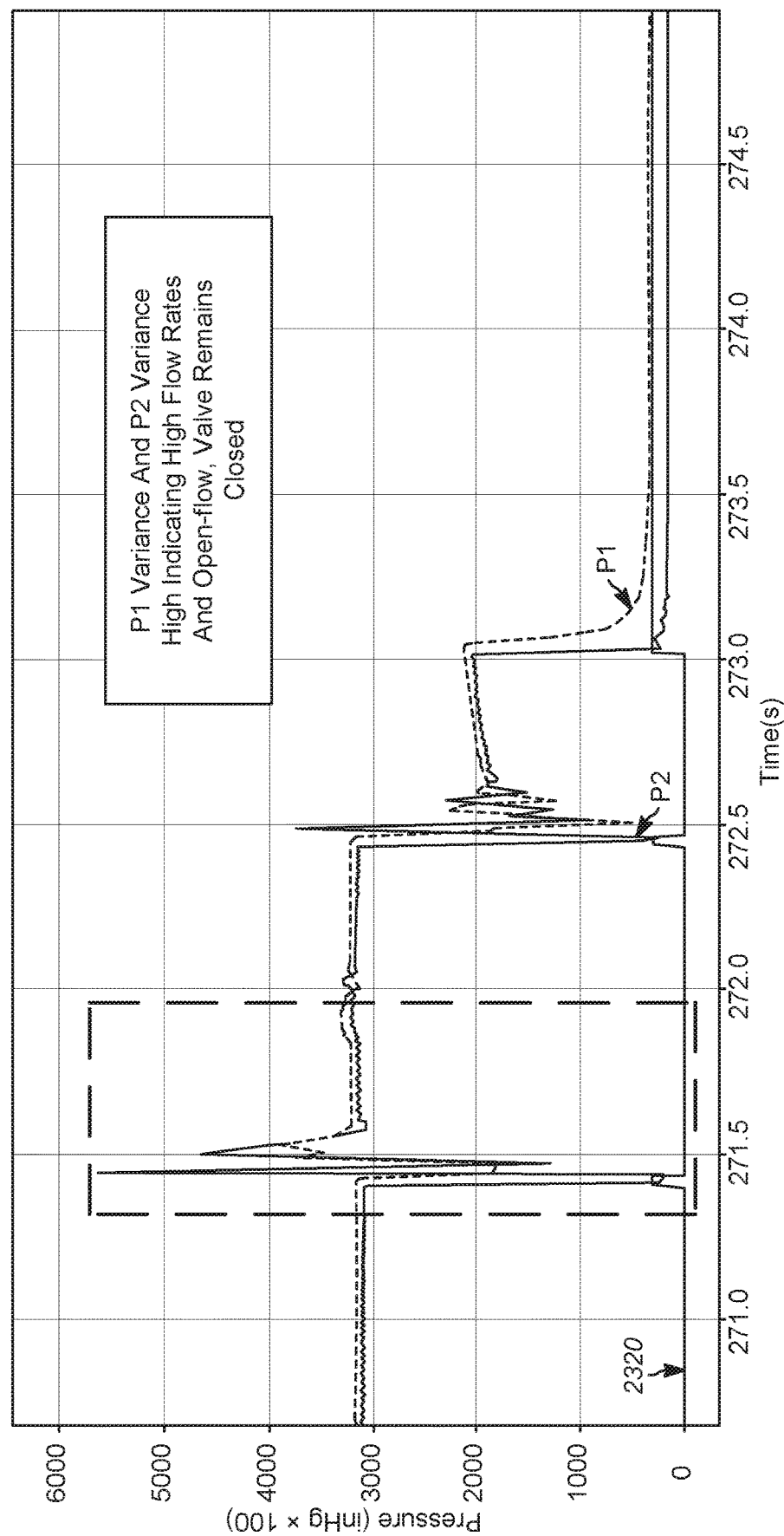
FIGS. 66-70 illustrate pressure profiles of particular embodiments detected using multiple pressure sensors used for dynamic system state detection.

FIG. 66 illustrates detection of open flow conditions using P1 and P2 pressure profiles, in particular embodiments. For instance, for the starting time interval window of FIG. 66 corresponding to a first valve cycling event, both P1 and P2 pressure variances are large based on cycling the valve, which may indicate open flow conditions. Based on that determination, the valve may be kept closed. Separate or additional determinations of open flow may be made, for instance, based on comparing median pressure levels at the start and the end, and/or based on comparing median pressure levels at the end relative to the ambient pressure. In particular embodiments, if P1 variance multiplied by the P2 variance is large, and P1 median pressure at the start is less than the P1 median pressure at the end, and if P1 median pressure at the end is approximately equal to ambient pressure, a determination of open flow may be made. In particular embodiments, if P1 variance multiplied by the P2 variance is large, and P2 median pressure at the start is less than the P2 median pressure at the end, and if P2 median pressure at the end is approximately equal to ambient pressure, a determination of open flow may be made.

Figure 67:
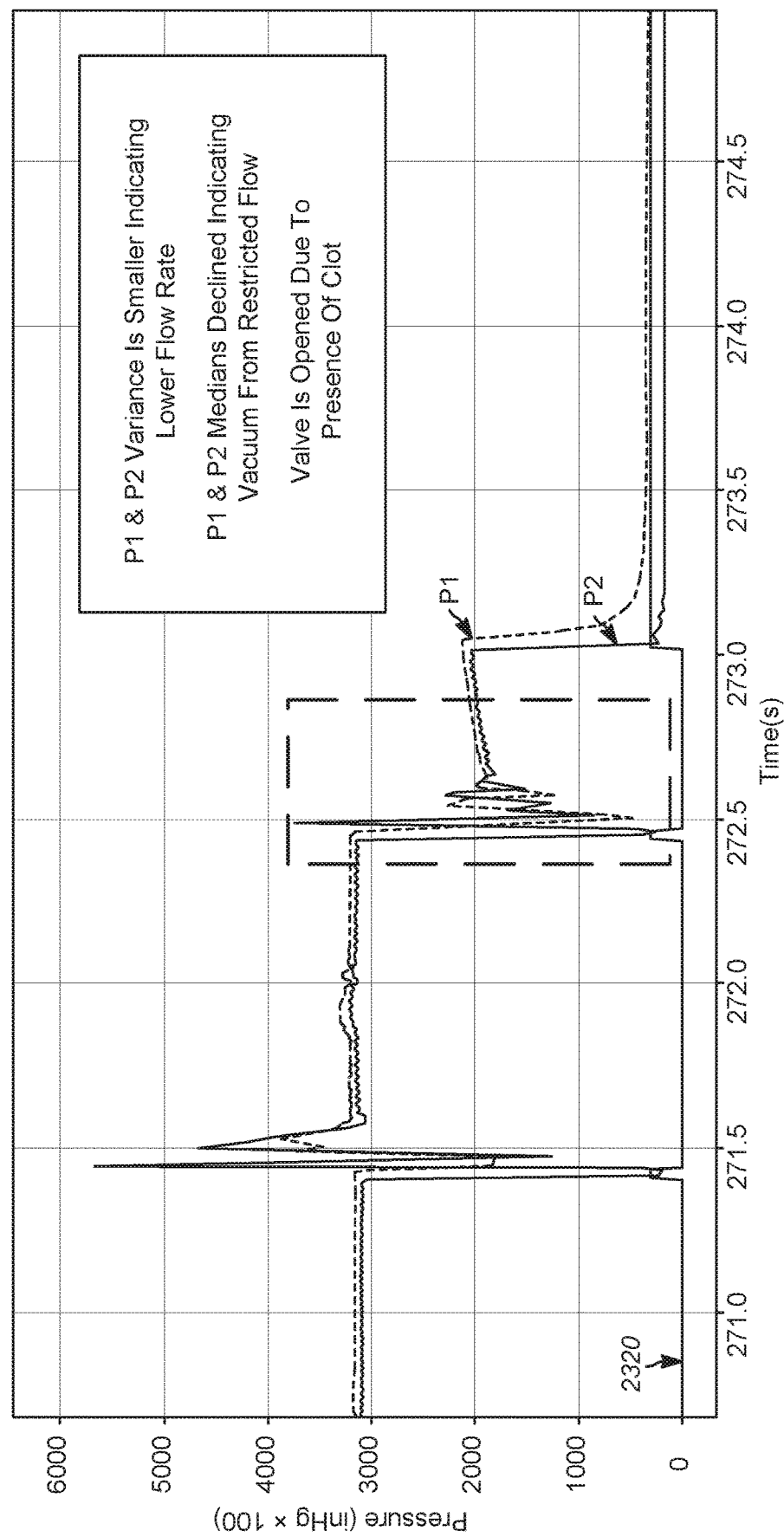

For the middle time interval window of FIG. 67 corresponding, in particular embodiments, to a second valve cycling event, both P1 and P2 pressure variances are relatively reduced, which may indicate lower flow rates. Additionally, the median values of P1 and P2 pressure levels taken during this middle time interval window are also reduced, which may indicate restricted flow due to the presence of a clot. Based on that determination, the valve may be opened. In particular embodiments, if the P1 variance multiplied by the P2 variance were small, lower flow rates may be indicated. In particular embodiments, if the P1 variance multiplied by the P2 variance were large and the system was determined to not be in free flow, lower flow rates and/or restricted flow may be indicated, and the valve may be opened due to presence of a clot.

Figure 68:
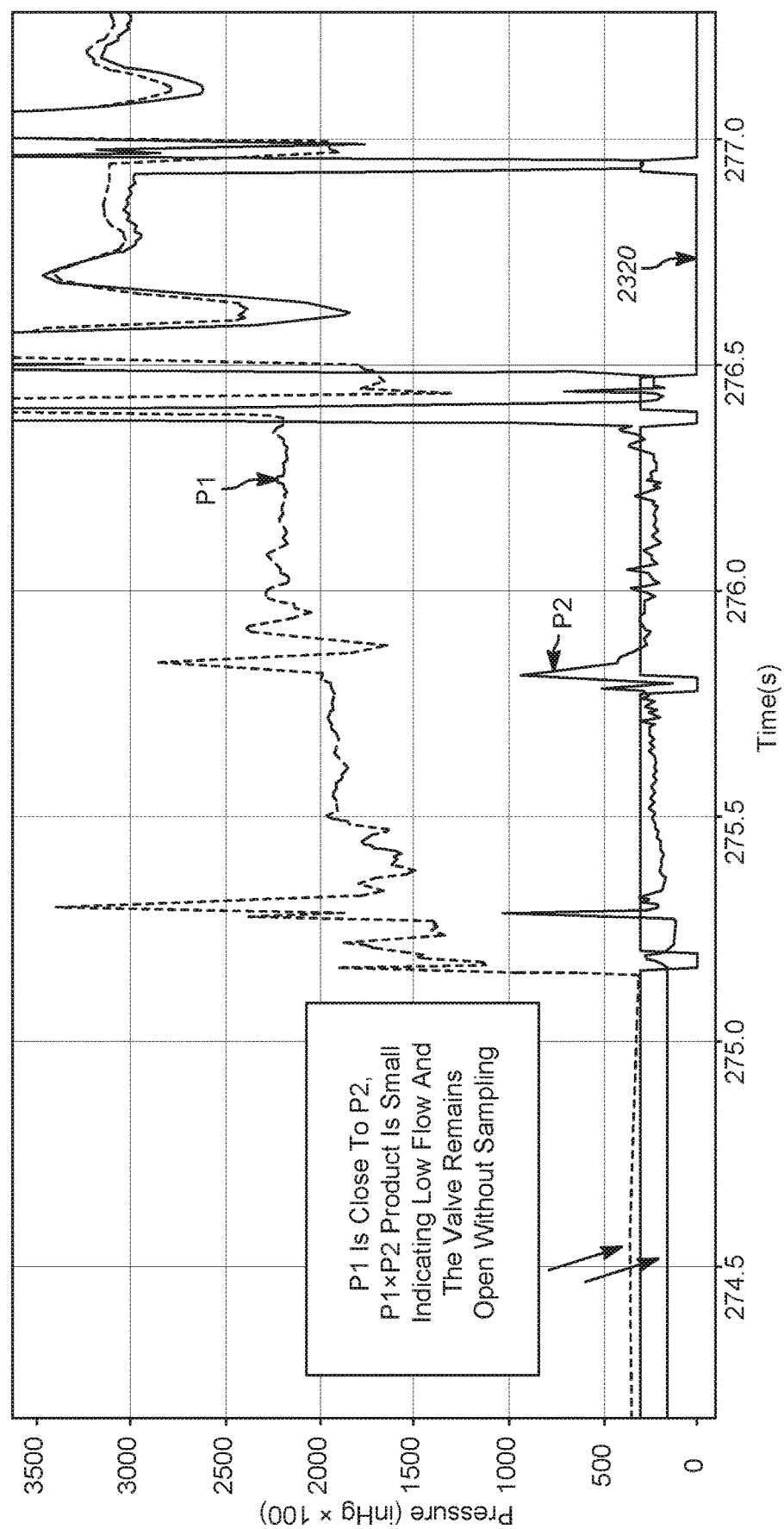
Figure 69:
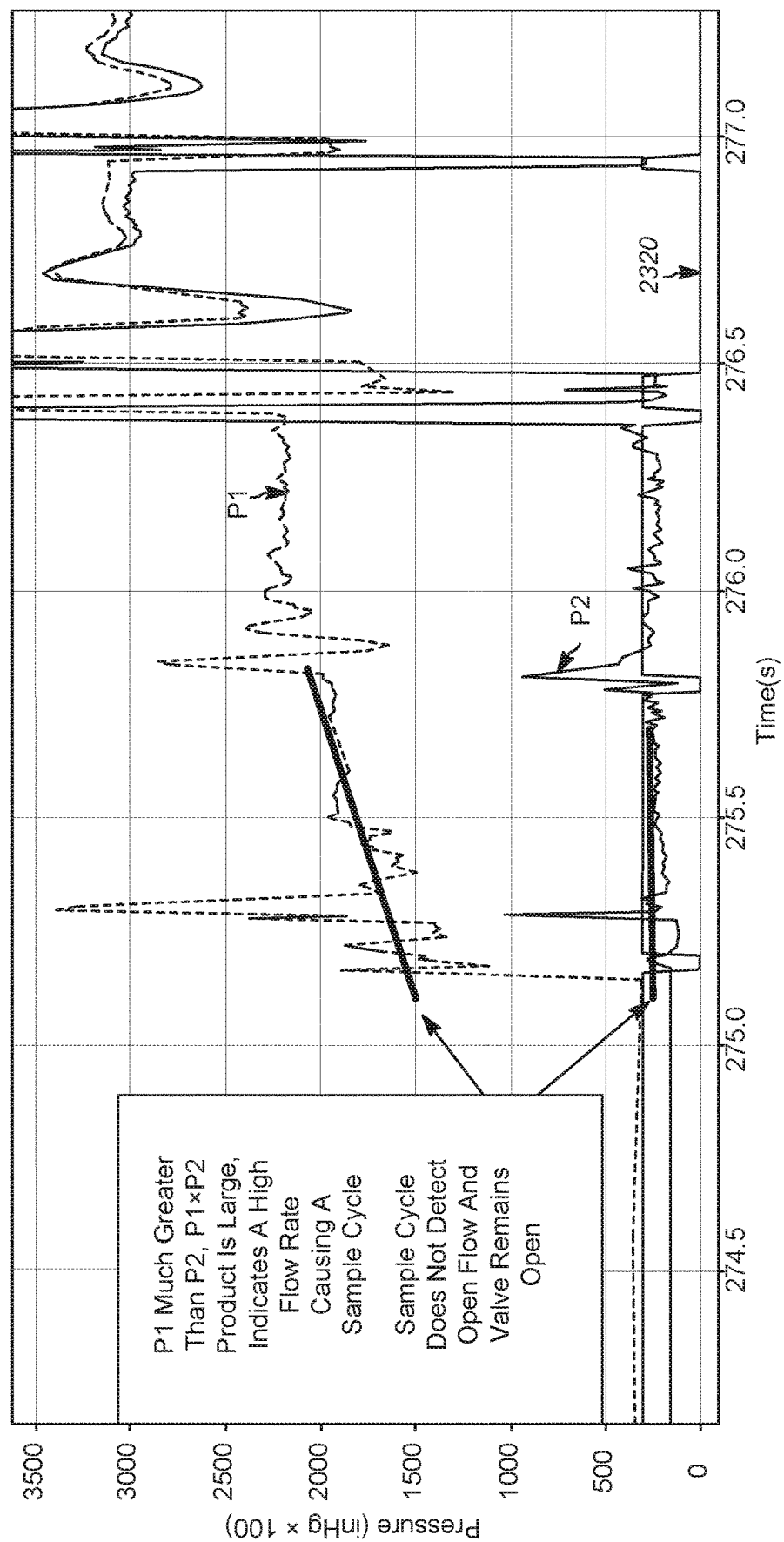
Figure 70:
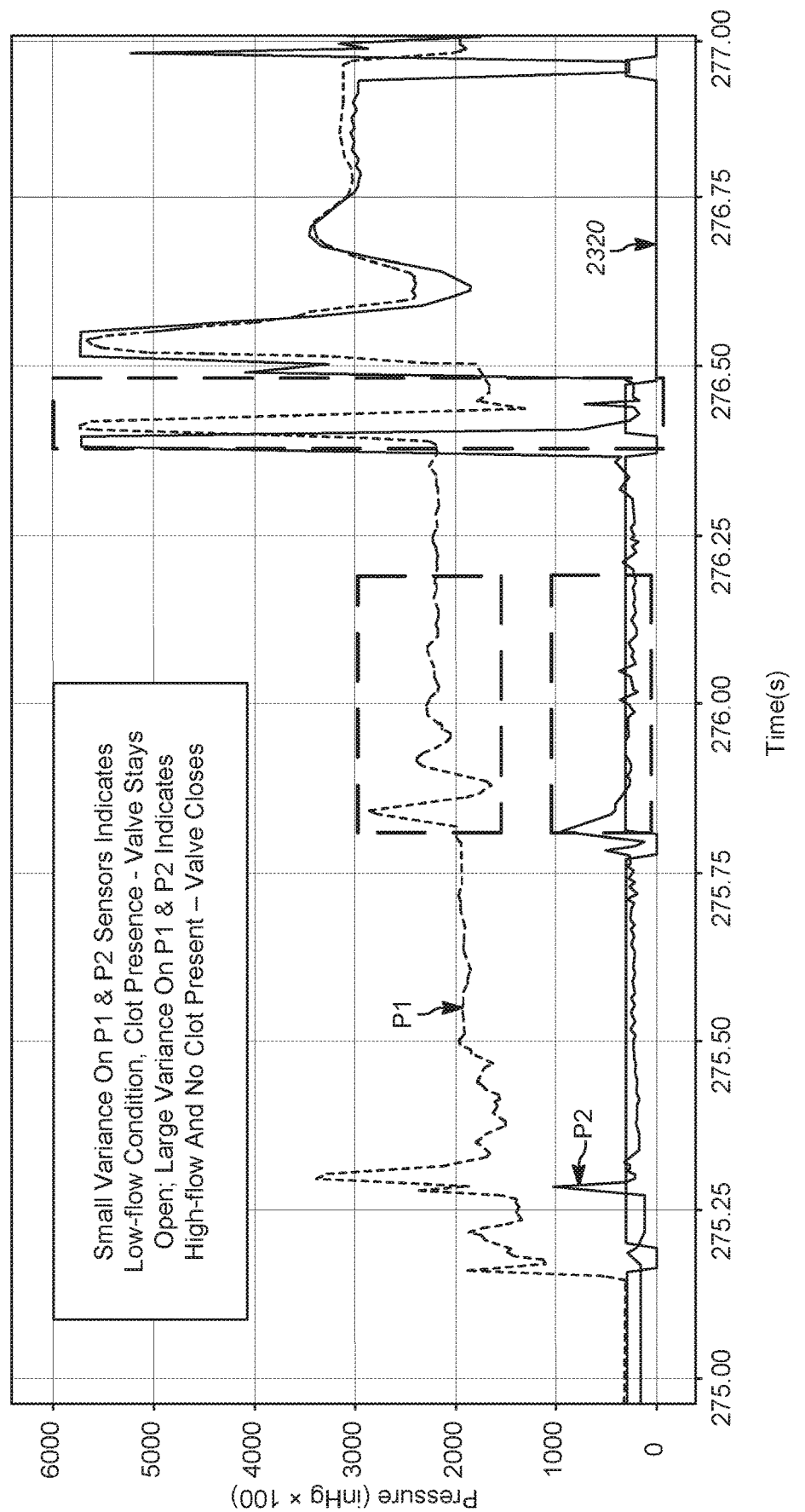

FIG. 68-70 illustrate system state detection using P1 and P2 in an open-valve state without valve cycling, in particular embodiments. As illustrated in FIG. 68, in particular embodiments at the beginning of the open-valve state, P1 pressure is close to P2 pressure, and the product of P1 and P2 is small, which may indicate low flow rates. In particular embodiments, if P1 pressure is approximately equal to P2 pressure, and if P1 pressure is approximately equal to ambient pressure, and if P2 pressure is approximately equal to ambient pressure, and if P1 pressure multiplied by P2 pressure is small, low flow may be indicated. Based on that determination of low flow, the valve may remain open without sampling. FIG. 69 illustrates an increase in flow in particular embodiments. As illustrated in the figure, P1 increases to a value much greater than P2, producing a large product of P1 and P2, which may indicate a high flow rate that may cause a sample cycle, and may cause the valve to operate. As the sample cycle may not detect open flow, the valve may remain open. In particular embodiments, if P1 pressure is greater than P2 pressure, and if P1 pressure multiplied by P2 pressure is large, and if P1 and P2 ambients are usable, a high flow rate may be indicated, causing a sample cycle. As the sample cycle may not detect open flow, the valve may remain open. In particular embodiments, if P1 pressure is much greater than P2 pressure, and if P1 and P2 ambients are not usable, a high flow rate may be indicated, causing a sample cycle. As the sample cycle may not detect open flow, the valve may remain open. In particular embodiments, if P1 pressure multiplied by P2 pressure is large, and if P1 and P2 ambients are not usable, a high flow rate may be indicated, causing a sample cycle. As the sample cycle may not detect open flow, the valve may remain open.

FIG. 70 illustrates a comparison of variances of P1 and P2 pressures observed during time interval windows in the middle and toward the end of the profiles illustrated, in particular embodiments. Small variances in P1 and P2 pressures, such as those observed approximately during the middle of the profile sequence illustrated in this figure, may indicate low flow conditions and possible presence of clot(s). In such cases, the valve may stay open. Conversely, such as observed toward the end of the pressure profile sequence illustrated in this figure, large variances in P1 and P2 pressures may indicate high flow rates and the absence of clots. In such cases, the valve may close. In particular embodiments, if P1 variance squared (i.e., P1 variance multiplied by itself) multiplied by P2 variance is large, a high flow rate may be determined, indicating the absence of clots. Based on this determination, the valve may close.

In particular embodiments, physical parameters may be extracted from sensor data. Specific features and pressure parameters detected during dynamic system state detection may be dependent on, differently dependent on, or independent of, particular physical parameters. For example, as previously discussed, Starting Distal Pressures and/or Maximum Absolute Rebound Pressures may be correlated with blood viscosity in particular embodiments. Differential Starting Distal Pressures, in contrast, may be stable with changes in blood viscosity in particular embodiments. Based on other known parameters, in particular embodiments, on comparison to known databases and/or selectively generating pressure changes in the system, physical parameters such as blood viscosity, clot or thrombus characteristics such as elasticity or deformability, catheter and/or connection tubing dimensions, geometries, configurations and other characteristics may be determined from detecting sensor profiles, such as pressure profiles. In particular embodiments, parameters such as clot or thrombus characteristics determined from detecting sensor profiles may be used to determine the selective application of particular operational modes, such as extraction, modulation, and/or maceration modes.

As has been discussed, system state determination may be based on determining one or more system state scores. Algorithms and thresholds for determining and interpreting system state scores may be adapted, in particular embodiments, based on physical conditions, such as ambient and other temperatures and pressures; based on material parameters, such as elasticity of the connection tubing, or viscosity of the blood; based on geometry and configuration parameters, such as the length or diameter of the aspiration catheter; based on characteristics of the thrombus, such as elasticity or deformability; and/or based on other detected parameters, such as pressure parameters.

MISCELLANEOUS

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. An aspiration thrombectomy system, comprising:
an aspiration catheter configured to accommodate fluid;
connection tubing coupled to the aspiration catheter, wherein the connection tubing is configured to act as a common conduit for fluid communication between the aspiration catheter and a vacuum source;
one or more controllable valves, wherein each valve is configured to operate in a plurality of operational states, and wherein each valve is operable to selectively open and close to control fluid flow in the aspiration thrombectomy system;
one or more pressure sensors, wherein each pressure sensor is associated with the aspiration catheter or the connection tubing; and
an automated controller configured to:
operate one or more of the valves in a respective first operational state of the plurality of operational states to generate one or more changes in one or more pressure levels of fluid in the aspiration catheter or the connection tubing;
detect, via one or more of the pressure sensors, one or more pressure levels, wherein changes in the detected pressure levels are correlated with the one or more generated changes in pressure levels;
determine one or more system states in the aspiration catheter or the connection tubing based on one or more system state scores, wherein at least one system state score is determined based on the detected pressure levels and is indicative of a measure of occlusion in the aspiration catheter or the connection tubing; and
operate, based on the determined system states, one or more of the valves in a respective second operational state of the plurality of operational states.

2. The aspiration thrombectomy system of claim 1, wherein the second operational state is the same as the first operational state.

3. The aspiration thrombectomy system of claim 1, wherein at least one of the system state scores is determined to have decreased below a threshold score, and wherein the second operational state is an intermittent aspiration operational state based on the determination that at least one of the system state scores has decreased below the threshold score.

4. The aspiration thrombectomy system of claim 1, wherein at least one of the system state scores is determined to have increased above a threshold score, and wherein the second operational state is a modulated aspiration operational state based on the determination that at least one of the system state scores has increased above the threshold score.

5. The aspiration thrombectomy system of claim 1, wherein one or more of the system state scores are further based on one or more geometric characteristics of the aspiration catheter, and wherein at least one of the one or more geometric characteristics of the aspiration catheter is determined based on the one or more detected pressure levels.

6. The aspiration thrombectomy system of claim 1, wherein one or more of the system state scores are further based on one or more ambient environmental parameters of the aspiration thrombectomy system.

7. The aspiration thrombectomy system of claim 1, wherein one or more of the system state scores are further based on one or more material parameters associated with the aspiration thrombectomy system, and wherein at least one of the one or more material parameters is determined based on the one or more detected pressure levels.

8. The aspiration thrombectomy system of claim 1, wherein one or more of the system state scores are further based on one or more thrombi parameters associated with one or more thrombi in the aspiration catheter or the connection tubing, and wherein at least one of the one or more thrombi parameters is determined based on the one or more detected pressure levels.

9. The aspiration thrombectomy system of claim 1, wherein one or more of the system state scores are further based on one or more fluid parameters associated with one or more fluids in the aspiration catheter or the connection tubing, and wherein at least one of the one or more fluid parameters is determined based on the one or more detected pressure levels.

10. The aspiration thrombectomy system of claim 1, wherein one or more of the system scores are further based on one or more pressure parameters, and wherein at least one of the one or more pressure parameters is determined based on the one or more detected pressure levels.

11. The aspiration thrombectomy system of claim 10, wherein the pressure parameters comprise one or more of a starting pressure level, a differential in starting pressure levels, an ending pressure level, a differential in ending pressure levels, a peak pressure level, and a variance in pressure levels.

12. The aspiration thrombectomy system of claim 1, wherein at least one of the one or more controllable valves is a controllable pressure valve, and wherein the aspiration thrombectomy system further comprises a pressure source in fluid communication with the connection tubing via the controllable pressure valve.

13. The aspiration thrombectomy system of claim 1, wherein at least one of the system states is determined to be an open flow state, and wherein the second operational state is an intermittent aspiration operational state based on the determination of the open flow state.

14. The aspiration thrombectomy system of claim 1, wherein at least one of the system states is determined to be an open flow state, wherein at least one of the one or more controllable valves is a vacuum valve, and wherein the second operational state comprises closing the vacuum valve based on the determination of the open flow state.

15. The aspiration thrombectomy system of claim 1, wherein at least one of the system states is determined to be a partially occluded flow state, and wherein the second operational state is a continuous aspiration operational state based on the determination of the partially occluded flow state.

16. The aspiration thrombectomy system of claim 1, wherein at least one of the system states is determined to be an occluded flow state, and wherein the second operational state is a modulated aspiration operational state based on the determination of the occluded flow state.

17. The aspiration thrombectomy system of claim 1, wherein at least one of the system states is determined to be an occluded flow state, wherein at least one of the one or more controllable valves is a vacuum valve, and wherein the second operational state comprises opening the vacuum valve based on the determination of the occluded flow state.

18. The aspiration thrombectomy system of claim 1, wherein the automated controller is further configured to:

determine, for each determined system state, whether the system state is the same as a previously determined system state; and determine whether a number of consecutive system states that are the same exceeds a threshold number.

19. The aspiration thrombectomy system of claim 18, wherein the second operational state is selected based on the determination that the number of consecutive system states that are the same exceeds the threshold number.

20. A method for aspiration thrombectomy, comprising:

operating, by an automated controller, one or more controllable valves in a respective first operational state of a plurality of operational states to generate one or more changes in one or more pressure levels of fluid in an aspiration catheter or connection tubing, wherein each of the one or more valves is operable to selectively open and close to control fluid flow;

detecting, via one or more pressure sensors, one or more pressure levels associated with the aspiration catheter or the connection tubing, wherein changes in the detected pressure levels are correlated with the one or more generated changes in pressure levels;

determining one or more system states in the aspiration catheter or the connection tubing based on one or more system state scores, wherein at least one system state score is determined based on the detected pressure levels and is indicative of a measure of occlusion in the aspiration catheter or the connection tubing; and operating, based on the determined system states, one or more of the valves in a respective second operational state of the plurality of operational states.

* * * * *